(12) United States Patent
Leonard et al.

(10) Patent No.: US 8,956,519 B2
(45) Date of Patent: Feb. 17, 2015

(54) DEVICE FOR DETECTING AN ANALYTE

(75) Inventors: Lee Leonard, Sunnyvale, CA (US); Joseph A. Duimstra, Sunnyvale, CA (US); Eric Lee, Sunnyvale, CA (US); Mark Micklatcher, Hayward, CA (US); Victor Simonyi, Sunnyvale, CA (US); Gregory G. Wildgoose, Sunnyvale, CA (US); Joseph I. Keto, Sunnyvale, CA (US); Anton Seidl, Sunnyvale, CA (US)

(73) Assignee: Senova Systems, Inc., Mill Valley, CA (US)

( * ) Notice: Subject to any disclaimer, the term of this patent is extended or adjusted under 35 U.S.C. 154(b) by 312 days.

(21) Appl. No.: 13/258,647

(22) PCT Filed: Mar. 25, 2010

(86) PCT No.: PCT/US2010/028726
§ 371 (c)(1),
(2), (4) Date: Nov. 17, 2011

(87) PCT Pub. No.: WO2010/111531
PCT Pub. Date: Sep. 30, 2010

(65) Prior Publication Data
US 2012/0090995 A1    Apr. 19, 2012

Related U.S. Application Data

(60) Provisional application No. 61/163,139, filed on Mar. 25, 2009, provisional application No. 61/225,855, filed on Jul. 15, 2009, provisional application No. 61/289,318, filed on Dec. 22, 2009, provisional application No. 61/308,244, filed on Feb. 25, 2010, provisional application No. 61/309,182, filed on Mar. 1, 2010.

(51) Int. Cl.
*G01N 27/30* (2006.01)
*G01N 27/26* (2006.01)
(Continued)

(52) U.S. Cl.
CPC .......... *G01N 27/4166* (2013.01); *G01N 27/302* (2013.01)
USPC .......... 204/416; 204/406; 73/1.02; 73/53.01; 422/82.03

(58) Field of Classification Search
CPC .......... G01N 27/4166; G01N 27/4167; G01N 27/301; G01N 27/302; G01N 27/333; G01N 27/4117; G01N 27/4035
USPC ................ 204/406, 416; 422/82.03; 73/1.05, 73/53.01
See application file for complete search history.

(56) References Cited

U.S. PATENT DOCUMENTS 4,083,754 A    4/1978  Outsuka et al.
5,223,117 A *  6/1993  Wrighton et al. ............. 204/415
(Continued)

FOREIGN PATENT DOCUMENTS

EP    0 228 969    7/1987
JP    53-55069     10/1951
(Continued)

OTHER PUBLICATIONS

Wildgoose, Gregory G. et al., "Anthraquinone-Derivatised Carbon Powder: Reagentless Voltammetric pH Electrodes," Talanta 60, pp. 887-893, 2003.
(Continued)

*Primary Examiner* — Jennifer Dieterle
(74) *Attorney, Agent, or Firm* — David R. Conklin; Kirton McConkie

(57) ABSTRACT

Devices for detecting an analyte comprising a redox active analyte sensitive material on a working electrode and computer assisted signal acquisition and processing.

8 Claims, 37 Drawing Sheets

(51) Int. Cl.
*G01N 33/18* (2006.01)
*G01N 27/416* (2006.01)

(56) References Cited

U.S. PATENT DOCUMENTS

| | | | |
|---|---|---|---|
| 5,569,845 A * | 10/1996 | Butcher et al. | 73/64.44 |
| 6,353,323 B1 | 3/2002 | Fuggle | |
| 6,395,158 B1 * | 5/2002 | King et al. | 204/420 |
| 2003/0015423 A1 * | 1/2003 | LaGreca et al. | 204/416 |
| 2003/0217919 A1 * | 11/2003 | Yajima et al. | 204/412 |
| 2004/0185568 A1 | 9/2004 | Matsumoto | |
| 2005/0093556 A1 | 5/2005 | Mueller et al. | |
| 2005/0115833 A1 | 6/2005 | Wolf et al. | |
| 2007/0272552 A1 * | 11/2007 | Jiang et al. | 204/422 |
| 2008/0023328 A1 * | 1/2008 | Jiang et al. | 204/407 |
| 2008/0182136 A1 | 7/2008 | Arnold et al. | |
| 2008/0302660 A1 | 12/2008 | Kahn et al. | |
| 2009/0242399 A1 * | 10/2009 | Kamath et al. | 204/403.1 |
| 2010/0126850 A1 * | 5/2010 | Franzheld et al. | 204/283 |
| 2011/0125412 A1 * | 5/2011 | Salzer et al. | 702/22 |

FOREIGN PATENT DOCUMENTS

| | | |
|---|---|---|
| JP | 63-153164 | 10/1988 |
| JP | 63-236953 | 10/1988 |
| JP | 64-50 | 1/1989 |
| JP | 1-136453 | 9/1989 |
| JP | 04-361152 | 12/1992 |
| JP | 05-026840 | 2/1993 |
| JP | 05-209856 | 8/1993 |
| WO | 99/13325 | 3/1999 |
| WO | 2005085825 A1 | 9/2005 |
| WO | 2008154409 A1 | 12/2008 |

OTHER PUBLICATIONS

Riering, Helmut et al., "Synthesis of Substituted Benzoquinones and Their Use for Mediated Electrochemical Conversions," Electroorganic Synthesis, 58, pp. 859-873, 1994.

* cited by examiner

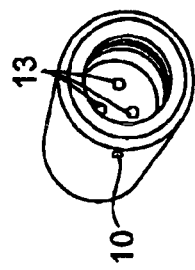
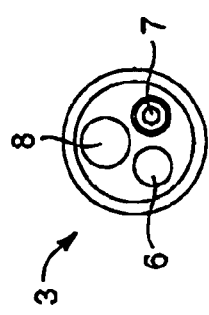
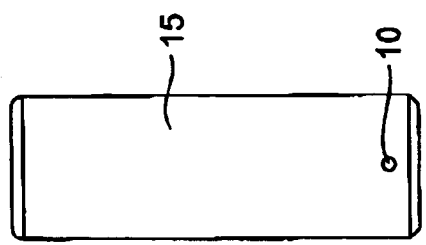
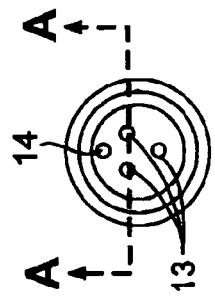
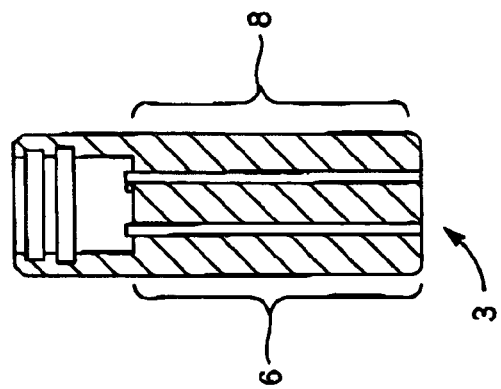

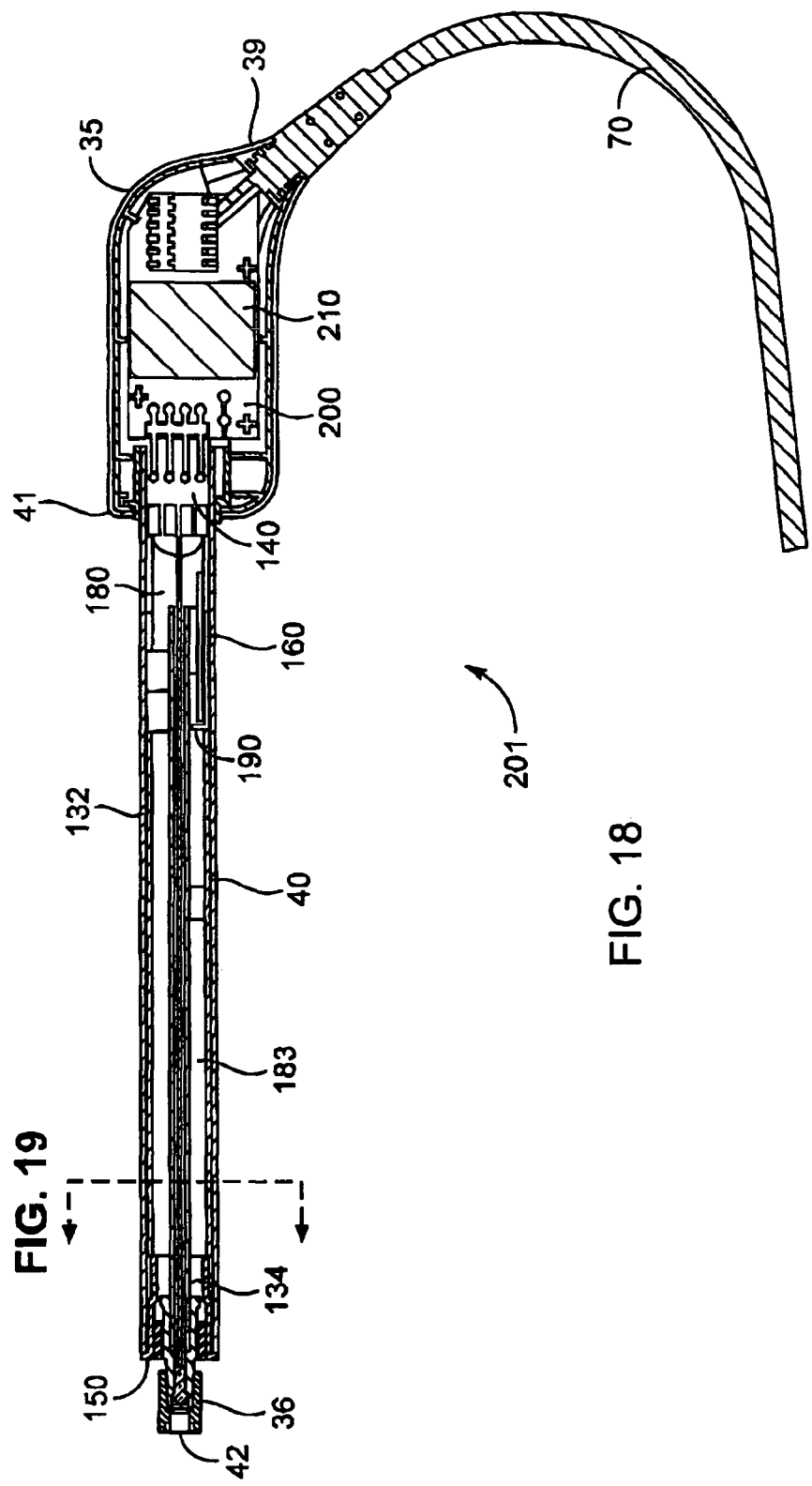

DEVICE FOR DETECTING AN ANALYTE

This application is a National Stage of International Application No. PCT/US2010/028726, filed Mar. 10, 2010, and entitled DEVICE FOR DETECTING AN ANALYTE, which claims the benefit of U.S. Provisional Application Nos. 61/163,139, filed Mar. 25, 2009; 61/225,855, filed Jul. 15, 2009; 61/289,318, filed Dec. 22, 2009; 61/308,244, filed Feb. 25, 2010; and 61/309,182, filed Mar. 1, 2010. This application claims priority to and incorporates herein by reference the above-referenced applications in their entirety.

BACKGROUND OF THE INVENTION

The present invention relates generally to technology for detecting an analyte. In various embodiments, the invention relates to devices for measuring pH.

pH, or potential of hydrogen, is a measure of the acidity or alkalinity of a solution. The pH of a solution is determined by the concentration, or more rigorously speaking the activity of hydrogen ions ($H^+$), also referred to as protons, within the solution. As the concentration of protons increases, the solution becomes more acidic. Conversely, the solution becomes more basic as the concentration of protons within the solution decreases. The concentration of protons within a solution has traditionally been measured with a glass electrode probe connected to an electronic meter that displays the pH reading.

A traditional pH probe or glass electrode is a type of ion-selective electrode made of a fragile, doped glass membrane that is sensitive to protons. This pH-responsive glass membrane is the primary sensing element in this type of probe. Protons within the sample solution bind to the outside of the glass membrane thereby causing a change in potential on the interior surface of the membrane. This change in potential is measured against the constant potential of a reference electrode such as the silver/silver chloride reference electrode. The difference in potential is then correlated to a pH value by plotting the difference on a calibration curve. The calibration curve is created through a tedious, multistep process whereby the user plots changes in potential for various known buffer standards. Most traditional pH sensors are based on variations of this principle.

The accuracy and reliability of traditional pH glass electrodes are unstable and therefore require careful, regular calibration and care involving tedious, time-consuming processes requiring multiple reagents and a well trained technician. The special properties and construction of the glass electrodes further require that the glass membrane be kept wet at all times. Thus, routine care of the glass probe requires regular performance of cumbersome and costly storage, rinsing, cleaning and calibration protocols by a well trained technician to ensure proper maintenance and working condition of the probe.

In addition to tedious maintenance, traditional glass electrodes are fragile thereby limiting field applicability of the glass electrode. In particular, the fragile nature of the glass electrode is unsuitable for use in food and beverage applications, as well as use in unattended, harsh or hazardous environments. Accordingly, there is a need in the art for a pH probe that addresses and overcomes the limitations of the traditional pH glass electrode. Such a pH probe device is disclosed herein.

SUMMARY OF THE INVENTION

The present invention provides solid state analyte sensors superior to those currently known in the art. The sensors described herein provide analyte-dependent signals demonstrating higher peak position stability, intensity, and longevity and are facile and inexpensive to construct. While this detailed description illustrates the invention with reference to pH sensors (i.e., pH meters and pH probe assemblies), the methods, materials and devices of the invention are generally applicable to the detection of any analyte of interest.

In some implementations, the present invention relates to a solid-state pH probe assembly and metering device that replaces the costly, fragile glass electrodes of traditional pH meters. In particular, the present invention relates to a pH metering system that utilizes a sensor chip that is calibration free. In some implementations, the present invention further provides a pH probe assembly demonstrating the first combined use of an analyte sensitive material with a conventional reference electrode. Thus, some embodiments of the present invention provide a pH probe assembly having a working electrode incorporating an analyte sensitive material, the working electrode being used in combination with a conventional reference electrode.

In some implementations of the present invention, a pH metering system is provided having a pH probe that is electrically coupled to a pH metering unit. The metering unit includes a display screen where the pH is displayed to a user. The pH metering system further includes a storage base for properly maintaining and storing the probe assembly when not in use.

A metering unit in accordance with the present invention generally performs dual functions of providing a voltage sweep to a sample solution, and of receiving and processing signals from the various electrodes of the probe assembly. A probe assembly in accordance with the present invention includes a counter electrode (CE), a working electrode (WE) and a reference electrode (RE). Each of these electrodes performs essential functions to assist the metering unit in determining the pH of a sample solution.

The CE includes an electro-conductive carbon-fiber tube that is electrically coupled to the metering unit. In some embodiments, CE may further include non-carbon based conductive materials, such as gold, platinum, and others known in the art. A voltage sweep from the metering unit is applied to the CE which is in turn applied to a sample solution in which the probe assembly is inserted. The RE is coaxially positioned within the CE and is configured to accurately sense and determine the voltage being applied by the CE. The WE is centrally positioned on the end of a sensor tip, said sensor tip being coaxially positioned central to the RE, and is optionally disposable. Thus, in some embodiments, the RE is interposedly disposed between the externally positioned CE and the centrally positioned WE.

The WE is further modified to include an analyte sensitive material (ASM) coating. The ASM includes a chemical compound that is sensitive to voltage and undergoes a reversible electrochemical redox reaction that is dependent upon the concentration of analyte in a sample solution. For example, where there is a high concentration of protons present in a sample solution, the redox reaction occurs at a more positive voltage. Conversely, where there is a low concentration of protons present in a sample solution, the redox reaction occurs at a more negative voltage. When the redox reaction occurs, electrons flow to or from the ASM via the WE. This current flow permits a signal to be sent to the metering unit. The signal is recorded and then compared to the voltage reading of the RE. The voltage reading of the RE is then compared to a standardized voltage for a known pH buffer. A comparison between the voltage reading and the standardized voltage produces a pH value for the sample solution.

In some implementations of the present invention, the probe assembly includes on-board electronics and processing circuitry whereby analog signals from the probe assembly are amplified prior to being sent to the metering unit. Thus, electromagnetic interferences that are commonly experienced due to sending low amplitude analog signals over an electrical cord are avoided.

The coaxial configuration of the probe assembly provides the RE with an oversized annular frit. One benefit of the annular frit is the increased surface area provided. The increased surface area increases the longevity of the probe assembly due to the increased tolerance for contamination. As compared to a frit having a smaller surface area, the annular frit of the present invention will last longer before having to be replaced.

In some implementations of the present invention, a storage base is provided for the probe assembly. The RE of the present invention is optimally maintained when it is prevented from drying out. A storage base in accordance with the present invention provides a weighted base having an opening configured to receive and support a shaft portion of the probe assembly. Storage base generally includes an internal space configured to hold a bottle of wetting solution that is accessible by the probe assembly via the opening. The bottle of wetting solution further includes a modified cap having a plurality of flaps that act to wipe the outer surface of the probe assembly upon insertion and removal of the assembly from the storage base. The flaps further prevent an unwanted buildup of pressure within the bottle upon insertion of the probe assembly in the wetting solution bottle. A seal is further interposed between the bottle cap and the storage base to prevent leakage of the wetting solution within the interior space of the storage base.

Some implementations of the present invention further include a packaging system for storing and protecting WE tips prior to use. The packaging system generally includes a disposable polymer base having a plurality of wells for holding disposable WE tips. Each well is sealed with a foil lid to protect the tip from the surrounding environment. The WE tips are removed from the packaging by simply forcing a contact point of the probe through the foil lid to engage the tip. In some implementations, a storage tray is further provided to securely hold the packaging system. The storage tray includes a well for securely holding the disposable base and may further include a tapered slot for assisting the user in removing a used WE tip from the probe assembly.

Some implementations of the present invention further include a clip configured to secure the probe assembly for use with a beaker or similar open top container. In some embodiments a clip is provided having a first feature for securing the clip to a container and a second feature for securing the probe assembly to the clip. In other embodiments a clip is provided having a first feature for securing the clip to a container and a second feature for securing a cable of the probe assembly to the clip.

BRIEF DESCRIPTION OF THE DRAWINGS

FIG. 7, in parts A to E, provides detailed views of various aspects of the sensor tip of the first exemplary embodiment of the invention shown in FIGS. 5 and 6.

FIG. 18 is a cross-section view of an implementation of a solid-state pH probe assembly in accordance with a representative embodiment of the present invention.

DETAILED DESCRIPTION

Figure 1:
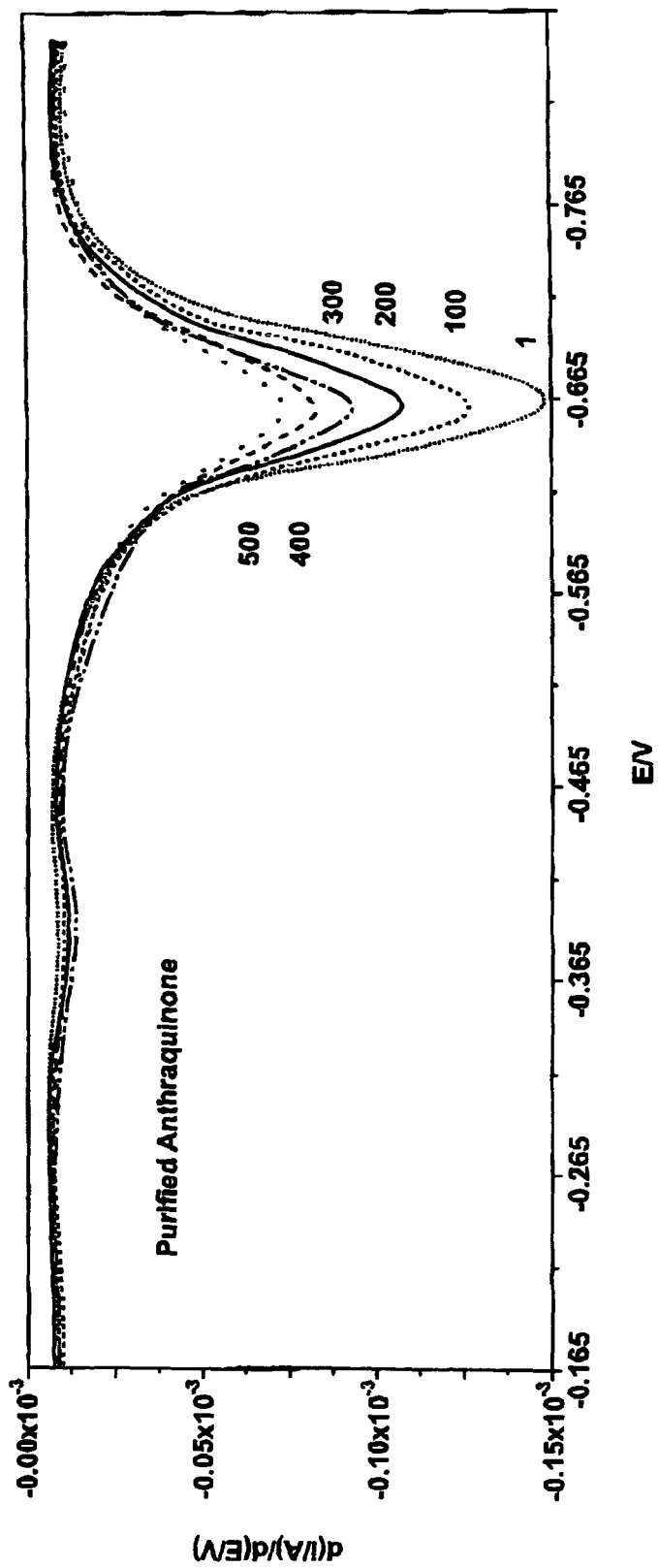
FIG. 1 shows a series of voltammograms obtained using a sensor comprising anthraquinone (AQ) in pH 7 phosphate buffer (see Example 1 below) over the course of 4 hours. The bottom trace represents the first voltammogram with each subsequent line showing the 100th, 200th, 300th, 400th, and 500th voltammograms. As each voltammogram takes approximately 30 seconds to perform and the voltammograms were run consecutively, the time at which the voltammograms were obtained was 50 minutes, 100 minutes, 150 minutes, 200 minutes and 250 minutes for the $100^{th}$, $200^{th}$, $300^{th}$, $400^{th}$, and $500^{th}$ voltammogram respectively.

The present invention provides solid state analyte sensors superior to those currently known in the art. Specifically, the present invention provides a solid state analyte sensor system that provides improved analyte-dependent signals exhibiting more well-defined peaks, greater peak position stability, higher peak intensity, and increased peak longevity, and is simpler and not as costly to construct, relative to currently available analyte sensor systems. Some embodiments of the sensor components, as well as configurations and compositions of those components, are described in detail below, following definitions provided for the convenience of the reader.

Definitions

As used in the specification and the appended claims, the singular forms "a," "an" and "the" include plural referents unless the context dictates otherwise. Thus, for example, reference to "a binder" includes mixtures of binders, and a reference to a conductive material may include more than one such material.

An "analyte" is a chemical species of interest present in a sample, the presence of which is detectable or the concentration of which is measurable by using an analyte sensor system that incorporates the working electrode of the present invention.

A "redox-active material" is one that may be oxidized and/or reduced. "Redox activity" refers to either or both of those processes.

An "analyte-sensitive material" or "ASM" is a redox-active material that is sensitive or substantially sensitive to the presence or concentration of an analyte in a sample within those user-defined application-specific tolerances. "Substantially sensitive" to an analyte is used to mean sensitive within the tolerances required for a given application, as those tolerances are defined by an end user.

An "analyte-insensitive material" or "AIM" is a redox-active material that is insensitive or substantially insensitive to the presence or the concentration of an analyte in a sample. "Substantially insensitive" to an analyte is used to mean insensitive within the tolerances required for a given application, as those tolerances are defined by an end user.

"Dispersed" or "associated" in reference to a material, means that it is dissolved in a solution or colloidally suspended in a gas, liquid or solid. The term also encompasses embodiments in which the material is abrasively immobilized, adsorbed, electrostatically bound or covalently bound to the surface of a solid or to a component of the solid. The term also encompasses embodiments in which the material is incorporated as a dopant in a crystal lattice. The term also encompasses materials intercalated within a solid.

An "electrochemical sensing system" includes a controller/processor unit (CPU) and at least one electrode.

"Sensor" refers collectively to the component electrodes of an electrochemical sensing system. A typical sensor includes a working electrode, a counter-electrode and a reference electrode (either a conventional reference electrode or a pseudo reference electrode), but may further include an analyte-insensitive electrode.

The "surface" of an electrode refers to the functional surface, i.e., that portion of the surface that is in contact with the analyte sample and serves an electrical or electrochemical purpose. It would not, for example, include the insulating WE housing through which no current or voltage passes. Similarly, the surface of an RE is the portion of the electrode surface in contact with the sample that detects current or electrical potential. The surface of a CE refers to the portion in contact with the sample which serves to deliver or accept current to or from the sample.

A "working electrode" or "WE" is the electrode at which the electrochemical process for detecting the analyte of interest occurs. In a sensor, the working electrode may be sensitive to one or more analyte(s) in the test sample, or it may be chemically modified with analyte sensitive species/materials. The electrochemical response of the working electrode is measured after some perturbation to the system under study has been applied. For example, the perturbation may be the application of a potential difference to the WE which induces electron transfer to occur, and the resulting current at the working electrode is then recorded as a function of the applied potential (voltammetric mode). This example of mode of operation is illustrative and not exhaustive, as many other modes are known in the art.

An "analyte insensitive electrode" (AIE) is a special case of a working electrode where the current flow depends in part on redox processes that are independent of the presence or concentration of species (apart from a minimum threshold of supporting electrolyte) in the sample composition including but not limited to the analyte. The AIE serves to provide a response that does not vary across time or sample composition and therefore can be used as an internal standard or 'zero point' to which the WE response may be compared. AIEs are defined in more detail in Patent Cooperation Treaty application No. PCT/US10/26842, incorporated herein in its entirety.

A "reference electrode" (RE) is an electrode used to monitor the potential difference applied to the WE. "Conventional reference electrodes" (CREs) have a certain fixed chemical composition and therefore a fixed electrochemical potential, thus allowing measurement of the potential difference applied to the WE in a known, controlled manner. A CRE typically comprises two halves of a redox couple in contact with an electrolyte of fixed ionic composition and ionic strength. Because both halves of the redox couple are present and the composition of all the species involved is fixed, the system is maintained at equilibrium, and the potential drop (i.e. the measured voltage) across the electrode-electrolyte interface of the CRE is then thermodynamically fixed and constant. For example a commonly used CRE system is the Ag|AgCl|KCl system with a defined and constant concentration of KCl. The two half-cell reactions are therefore: $Ag^+ + e^- \rightarrow Ag$; and $AgCl + e^- \rightarrow Ag + Cl^-$. The overall cell reaction is therefore: $AgCl \rightarrow Ag^+ + Cl^-$ for which the Nernst equilibrium potential is given as: $E = E^0 - (RT/F)*\ln [Cl^-]$ where E is the measured RE potential, $E^0$ is the standard potential of the Ag|AgCl couple vs. the standard hydrogen electrode with all species at unit activity (by convention this is defined as having a potential of 0.0V), R, T and F are the universal gas constant, temperature and Faraday constant respectively in appropriate units. Hence the potential of this system depends only on the concentration (more strictly speaking the activity) of $Cl^-$ ion present, which, if this is fixed, provides a stable, fixed potential. Many other CRE systems are known in the art. It is imperative that the composition of the CRE remains constant, and hence almost no current should be passed through the CRE (otherwise electrolysis will occur and the composition of the CRE will change), which necessitates the use of a third electrode, the counter electrode (CE) to complete the circuit. However, two-electrode configurations can be used in the special case where the WE is a microelectrode, having at least one dimension typically smaller than 100 microns. In this case, the currents passed at the WE are small, and therefore a two-electrode cell can be used with a CRE, but without the need for a CE.

The term "pseudo-reference electrode" (PRE) refers to a type of reference electrode which is sometimes used, particularly in non-aqueous electrolytes. These electrodes typically do not comprise both halves of a well-defined redox potential and are therefore not thermodynamic reference electrodes of fixed composition and potential. However, they provide a reasonably constant potential over the timescale of an electrochemical experiment (on the order of minutes), and the absolute potential of the PRE can then be calibrated back to a CRE if required. One example of a PRE is a silver wire (used commonly in non-aqueous electrochemistry).

To pass current through the cell, one further electrode may be required to complete the circuit. In some embodiments, this additional electrode is a "counter-electrode" or "CE" or sometimes an "auxiliary electrode." This electrode simply serves as a source or sink of electrons and allows current to flow through the cell. To avoid unwanted electrochemical redox processes occurring at the CE, which may interfere with the signal measured at the WE, CEs are typically made using relatively chemically inert materials, commonly platinum (Pt), but carbon (graphite) is also commonly employed.

As used herein, the term "coaxial" refers to a common axis about which various components, for example, electrodes, are positioned. In some embodiments, "coaxial" refers to a radial symmetry of concentrically or approximately concentrically positioned components. In some embodiments, the term "coaxial" refers to one or more electrodes being concentrically positioned within an outer or externally positioned electrode component; for example and without limitation, a WE, CE, and RE are coaxially positioned when the CE is the outer ring of a sensor tip that is immersed in the analyte solution, the WE is in the middle of the tip, and the RE is interposedly positioned between CE and the WE.

The terms "isolated compound" and "purified compound" mean a compound which has been substantially separated from, or enriched relative to, other compounds with which it occurs in nature. Isolated compounds are usually at least about 80%, at least 90% pure, at least 98% pure, or at least about 99% pure, by weight. The present disclosure is meant to include diastereomers as well as their racemic and resolved, enantiomerically pure forms and pharmaceutically acceptable salts thereof.

As used herein, the term "chemical moiety" refers to either a functional group of a molecule, or any part of a molecule including a functional group as a substructure. Non-limiting examples of chemical moiety groups include hydrogen, alkyl, aryl, heteroaryl, amino, amido, carboxyl, hydroxyl methyl, carbonyl, ether, alkoxy ether, and substituted or unsubstituted aryl or heteroaryl rings resulting therefrom.

As used herein, the term "chemical linker" refers to a chemical structure responsible for covalently binding an analyte sensitive material to a desired substrate. In some embodiments, the chemical linker comprises a chemical bond. In other embodiments, the chemical linker comprises one or more atoms interposed between two distinct chemical molecules. Further, in some embodiments the chemical linker comprises one or more molecules interposed between two distinct chemical molecules, for example, a chemical linker is interposed between an analyte sensitive material and a substrate of a working electrode.

The terms "alk" or "alkyl" refers to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, n-octyl, dodecyl, octadecyl, amyl, 2-ethylhexyl, and the like. An alkyl group is optionally substituted, unless stated otherwise, with one or more groups, selected from aryl (optionally substituted), heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted) amino, protected amino, amido, lactam, urea, urethane, sulfonyl, and the like.

The terms "ar", aryl" or "aryl ring" refer to aromatic homocyclic (i.e., hydrocarbon) mono-, bi- or tricyclic ring-containing groups preferably having 6 to 12 members such as phenyl, naphthyl and biphenyl. An aryl group is optionally substituted, unless stated otherwise, with one or more groups, selected from alkyl (optionally substituted alkyl), alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and the like. Optionally, adjacent substituents, together with the atoms to which they are bonded, form a 3- to 7-member ring.

The terms "heteroaryl" or "heteroaryl ring" refer to optionally substituted five-membered or six-membered rings that have 1 to 4 heteroatoms, such as oxygen, sulfur and/or nitrogen atoms, either alone or in conjunction with, additional nitrogen, sulfur or oxygen ring atoms. Furthermore, the above optionally substituted five-membered or six-membered rings can optionally be fused to an aromatic 5-membered or 6-membered ring system. For example, the rings can be optionally fused to an aromatic 5-membered or 6-membered ring system such as a benzene, pyridine or a triazole system.

The following ring systems are non-limiting examples of the heterocyclic (whether substituted or unsubstituted) radicals denoted by the term "heteroaryl": thienyl, furyl, pyrrolyl, imidazolyl, pyrazolyl, oxazolyl, isoxazolyl, thiazolyl, isothiazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b] pyridazinyl and purinyl, as well as benzo-fused derivatives, for example, benzoxazolyl, benzthiazolyl, benzimidazolyl and indolyl.

A heteroaryl group is optionally substituted, unless stated otherwise, with one or more groups, selected from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl (optionally, substituted), cycloalkyl (optionally substituted), (cycloalkyl)alkyl (optionally substituted), phenyl (optionally substituted), phenylalkyl (optionally substituted phenylalkyl). Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The terms "heterocycle", "heterocyclic", "heterocyclic group" or "heterocyclo" refer to fully saturated or partially unsaturated or completely unsaturated, including aromatic ("heteroaryl") or nonaromatic cyclic groups (for example, 3- to 13-member monocyclic, 7- to 17-member bicyclic, or 10- to 20-member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl, or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

A heterocyclo group is optionally substituted, unless stated otherwise, with one or more groups, selected from alkyl (including substituted alkyl), alkenyl, oxo, aryl (including substituted aryl), heterocyclo (including substituted heterocyclo), carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like, where optionally one or more pair of substituents together with the atoms to which they are bonded form a 3- to 7-member ring.

With this introduction and the above definitions in mind, the reader can better appreciate the various aspects and embodiments of the invention described below. For the convenience of the reader, this description is divided into various sections and subsections. In Section I, the Analyte Sensing Devices ("Meters") of the invention are described in terms of their various components. Part A focuses on the "Probe", describing in subsections 1 through 4, the electrodes on the probe (part 1, subparts a (WE), b (RE), c (CE), and d (IE)), the disposition of the electrodes on the probe (part 2, subparts a (coaxial), and b (other configurations)), and various probe related devices (part 4, subparts a (the probe clip), b (the "inkwell") and c (sealed packaging). Part B focuses on signal acquisition and processing. In Section II, related devices that can make the meters of the invention easier to use for various applications are described.

Section I: Analyte Sensing Devices

A(1)(a): Working Electrode (WE)

In some aspects, the working electrode (WE) of the present invention comprises at least one ASM and a substrate material. Suitable ASMs and substrate materials are discussed below. In some exemplary embodiments, a WE comprising anthraquinone (AQ) is prepared as described in Example 1, below. In some embodiments, the WE comprises two ASMs sensitive to the same analyte species, which are selected so as to provide a more sensitive measurement than is provided by a single ASM while minimizing the possibility of introducing additional overlapping peaks which must be resolved to determine analyte concentration. In some examples of this embodiment, the WE comprises both phenanthrenequinone (PAQ) and anthraquinone (AQ), also described in Example 1.

In other aspects, the WE may further comprise an AIM as an internal standard, as described in U.S. Patent Application Publication Nos. 20080023328, 20070272552, and 20080035481, each of which is incorporated herein by reference. Still further, in some embodiments the WE comprises two or more ASMs, each ASM being selected for sensitivity to a diverse analyte species.

In other aspects of the invention, the WE comprises highly purified ASM. In some embodiments, the WE comprises a redox-active material that is first purified prior to association with the surface of the substrate, as described below. In other embodiments, the ASM is AQ that is first purified and then covalently bound to a carbon-epoxy electrode as described in Example 1, below. In further embodiments, the WE comprises both purified AQ and purified PAQ, again as described in Example 1.

In some embodiments, the WE substrate is treated prior to ASM attachment to remove impurities, as discussed below.

In other embodiments, the ASM material present on the electrode surface is subject to further purification subsequent to association of the ASM with the substrate, yielding further improvement in the sensor signal shape. Suitable methods include but are not limited to rinsing with a suitable solvent, exposure of the electrode to an electric potential, sonication in a suitable solvent, or continuous extraction, for example, using a Soxhlet apparatus, or combinations of these procedures.

In some embodiments, ASM loading is further improved by subjecting the WE substrate to multiple cycles of ASM attachment and purification, as described below. In accordance with the present invention, the ordinarily skilled artisan can control the amount of pure ASM loaded onto the substrate, thereby permitting the manufacture of WEs having a size and shape appropriate to a given application to achieve the benefits of the invention.

In further embodiments, the WE comprises ASM present in a sufficient amount to result in a pH-dependent signal of between 10 and 300 microamps.

In some embodiments, the size and shape of the WE are chosen so as to minimize deleterious electrochemical effects among the WE, RE and CE while maintaining WE performance sufficient to allow a user to distinguish the analyte-dependent signal over background noise while maintaining signal quality.

WEs comprising a highly purified ASM offer several advantages over currently available WEs. Such electrodes have superior ASM loading per unit of electrode surface area, resulting in higher signal strength and greater signal longevity and a decreased load of non-ASM contaminants that adversely affect performance, as can be detected by observation of the shape of the signal peak. Their improved performance makes them amenable to miniaturization while maintaining the minimum signal strength and quality necessary to distinguish the analyte-dependent signal from background noise.

The WEs of the present invention may be configured so as to be removable from the sensor, allowing them to be easily interchanged.

Some embodiments of the present invention further provide improved analyte sensors having one or more WEs, each comprising one or more ASMs disposed on a substrate and in electrical connection with that substrate. Such ASMs may be adsorbed to the substrate surface or may be covalently attached to it.

In some aspects, the sensor comprises an AQ derivative as an ASM. In other aspects, the present invention comprises phenanthrenequinone (PAQ) or a derivative thereof as an ASM. Further, in other aspects the present invention comprises ortho-benzoquinone (OQ) or a derivative thereof as an ASM. Still further, in other aspects, the present invention comprises N,N'diphenyl para-phenylene diamine (DPPD) or a derivative thereof as an ASM.

In some aspects, the present invention comprises anthracene (AC) or a derivative thereof as an ASM. In other aspects, the present invention comprises naphthaquinone (NQ) or a derivative thereof as an ASM. Further, in other aspects the present invention comprises para-benzoquinone (PQ) or a derivative thereof as an ASM.

The present invention further provides a sensor construct comprising an ASM disposed on a substrate and in electrical connection with that substrate. This construct is known as the sensor. Various exemplary embodiments detailed below show improved peak intensity, longevity, and peak position shift at fixed pH over time compared to sensors currently known.

The sensors described herein comprise at least one ASM disposed on and in electrical connection with a substrate, wherein the ASMs interact more strongly with the substrate material and generate a more stable response to solutions of fixed pH during extended voltammetric cycles. The choice of ASM compound will depend upon the specific application for which the sensor will be used.

In some embodiments of the present invention, the WE sensor comprises derivatives of AQ. These sensors provide increased signal longevity and decreased peak positional drift with time at fixed pH as compared to sensors comprising AQ itself (compare FIGS. 1 and 2). Further, the response curve of these sensors is comparable to that of a conventional glass sensor (see e.g. FIGS. 3 and 4).

Suitable AQ derivatives include those that maintain the redox activity of the anthraquinone moiety but are substituted with polar groups with or without a spacer moiety between the polar group and the parent AQ molecule at one or more of the available sites for substitution, including but not limited to amino, amido, carboxyl, hydroxyl methyl, and carbonyl classes of functional groups to improve the signal longevity and peak stability using AQ derived WE constructs. Substituents such as beta-naphthol groups attached at one or more positions of the parent AQ molecule with or without a spacer moiety between the beta-naphthol and the parent AQ molecule may likewise be incorporated to improve the signal longevity and peak stability of the invention. Additionally, derivatives having extended aromatic structures such as 5,12-naphthacene quinone (3) display improved performance. Some embodiments of the AQ derivatives that may comprise this aspect of the invention include the compounds 2-carboxy AQ (1), 2-N-BOCethylene diamine AQ (2), 5,12-naphthacene quinone (3), 1-acetyl amido AQ (4), and 2-(beta-naphthol)methylanthraquinone (5), shown in Table 1.

TABLE 1

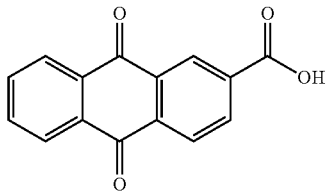 [SMILES: O=C(O)c1ccc2c(c1)C(=O)c1ccccc1C2=O]

TABLE 1-continued

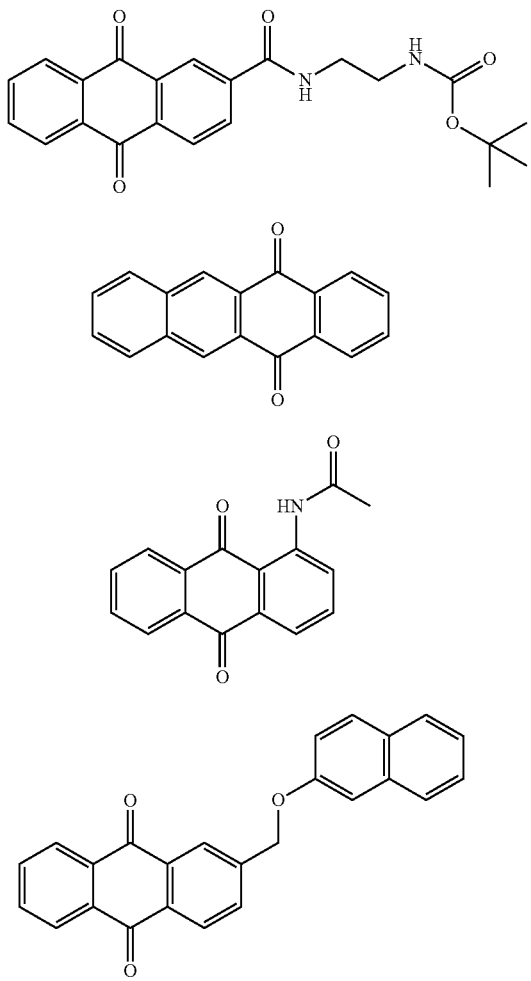

In some embodiments, the present invention provides 2-N-BOCethylene diamine AQ as an isolated or purified novel compound. In other embodiments, a WE is provided comprising the compound 2-N-BOCethylene diamine AQ. In some embodiments, the compound 2-N-BOCethylene diamine AQ is covalently bound to a substrate of the WE. In other embodiments, the compound 2-N-BOCethylene diamine AQ is physisorbed into a substrate of the WE.

In some embodiments, the present invention provides 2-(beta-napthol) methyl-anthraquinone as an isolated or purified novel compound. In other embodiments, a WE is provided comprising the compound 2-(beta-naphthol) methyl-anthraquinone. In some embodiments, the compound 2-(beta-napthol) methyl-anthraquinone is covalently bound to a substrate of the WE. In other embodiments, the compound 2-(beta-napthol) methyl-anthraquinone is physisorbed into a substrate of the WE.

The functionalities incorporated into the AQ molecules by derivatization have been shown to increase the useful lifetime of the WE construct. While not being bound by theory, one explanation for the observed longevity of these WE constructs is that the functionalities of the AQ derivatives contain moieties capable of participating in hydrogen bonding interactions with functionalities present on the graphite edge planes arising from oxidation during graphite production and/or subsequent processing. The hydrogen bonding interactions increase the affinity of the ASM molecule for the graphite surface and decrease the rate of any desorption processes that may be taking place.

In addition, the beta-naphthol derivatives of AQ have shown increased useful lifetimes of the WE construct when compared with WE constructs prepared from AQ. Possessing additional aromatic character, these AQ derivatives are predicted to have increased affinity for the basal planes of the graphite surface through pi-pi stacking interactions. Further, these AQ derivatives have shown enhanced peak position stability relative AQ over the same time frame of voltammetric analysis.

The substitutions to the AQ molecules detailed above may be applied to other classes of redox-active, analyte-sensing molecules to improve the longevity and accuracy versus time of these different classes of molecules provided the redox-active, analyte-sensitive behavior of the molecules remains intact. Various classes of ASM candidates are shown below:

In some embodiments of the invention, the WE sensor comprises AQ or an AQ derivative described by Formula I, shown in Table 2.

TABLE 2

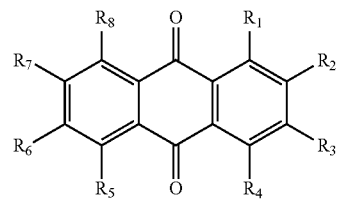

Formula I

Formula I demonstrates a chemical compound formula wherein R1, R2, R3, R4, R5, R6, R7, and R8 of the resultant compound are separately and independently chosen from the chemical moiety group consisting of hydrogen, alkyl, aryl, heteroaryl, amino, amido, carboxyl, hydroxyl methyl, carbonyl, ether and alkoxy ether, and wherein further any two adjacent groups (R1 and R2, or R2 and R3, or R3 and R4, or R5 and R6, or R6 and R7, or R7 and R8) may together form a substituted or unsubstituted aryl or heteroaryl ring.

In other embodiments, the sensor of the present invention comprises phenanthrenequinone (PAQ) or a PAQ derivative described by formula II, shown in Table 3.

TABLE 3

Phenanthrenequinone

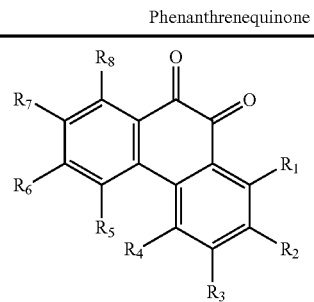

Formula II

Formula II demonstrates a chemical compound formula wherein R1, R2, R3, R4, R5, R6, R7, and R8 of the resultant compound are separately and independently chosen from the chemical moiety group consisting of hydrogen, alkyl, aryl, heteroaryl, amino, amido, carboxyl, hydroxyl methyl, carbonyl, ether and alkoxy ether, and wherein further any two adjacent groups (R1 and R2, or R2 and R3, or R3 and R4, or R5 and R6, or R6 and R7, or R7 and R8) may together form a substituted or unsubstituted aryl or heteroaryl ring.

In another aspect, the sensor of the present invention comprises ortho-benzoquinone or ortho-benzoquinone derivative described by formula III, shown in Table 4.

TABLE 4 ortho-benzoquinone

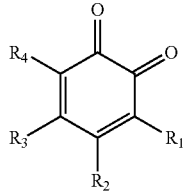

Formula III

Formula III demonstrates a chemical compound formula wherein R1, R2, R3, and R4 of the resultant compound are separately and independently chosen from the chemical moiety group consisting of hydrogen, alkyl, aryl, heteroaryl, amino, amido, carboxyl, hydroxyl methyl, carbonyl, ether and alkoxy ether, and wherein further any two adjacent groups (R1 and R2, or R2 and R3, or R3 and R4) may together form a substituted or unsubstituted aryl or heteroaryl ring.

In another aspect, the sensor of the present invention comprises N,N'-diphenyl para-phenylene diamine (DPPD) or DPPD derivative described by formula IV, shown in Table 5.

TABLE 5

N,N'-diphenyl para-phenylene diamine

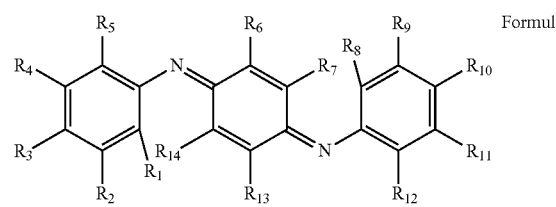

Formula IV

Formula IV demonstrates a chemical compound formula wherein R1, R2, R3, R4, R5, R6, R7, R8, R9, R10, R11, R12, R13 and R14 of the resultant compound are separately and independently chosen from the chemical moiety group consisting of hydrogen, alkyl, aryl, heteroaryl, amino, amido, carboxyl, hydroxyl methyl, carbonyl, ether and alkoxy ether, and wherein further any two adjacent groups (R1 and R2, or R2 and R3, or R3 and R4, or R4 and R5, or R6 and R7, or R8 and R9, or R9 and R10, or R10 and R11, or R11 and R12, or R13 and R14) may together form a substituted or unsubstituted aryl or heteroaryl ring.

In another aspect, the sensor of the present invention comprises anthracene or anthracene derivative described by formula V, shown in Table 6.

TABLE 6

Anthracene

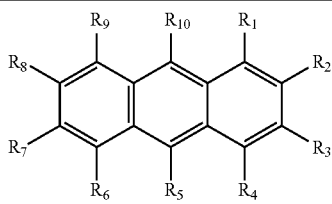

Formula V

Formula V demonstrates a chemical compound formula wherein R1, R2, R3, R4, R5, R6, R7, R8, R9 and R10 of the resultant compound are separately and independently chosen from the chemical moiety group consisting of hydrogen, alkyl, aryl, heteroaryl, amino, amido, carboxyl, hydroxyl methyl, carbonyl, ether and alkoxy ether, and wherein further any two adjacent groups (R1 and R2, or R2 and R3, or R3 and R4, or R6 and R7, or R7 and R8, or R8 and R9) may together form a substituted or unsubstituted aryl or heteroaryl ring.

In another aspect, the sensor of the present invention comprises naphthaquinone or napthaquinone derivative described by formula VI, shown in Table 7.

TABLE 7

Naphthaquinone

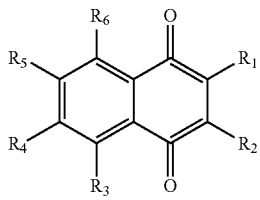

Fomula VI

Formula VI demonstrates a chemical compound formula wherein R1, R2, R3, R4, R5 and R6 of the resultant compound are separately and independently chosen from the chemical moiety group consisting of hydrogen, alkyl, aryl, heteroaryl, amino, amido, carboxyl, hydroxyl methyl, carbonyl, ether and alkoxy ether, and wherein further any two adjacent groups (R1 and R2, or R3 and R4, or R4 and R5, or R5 and R6) may together form a substituted or unsubstituted aryl or heteroaryl ring.

In another aspect, the sensor of the present invention comprises para-benzoquinone (PQ) or PQ derivative described by formula VII, shown in Table 8.

TABLE 8

Para-benzoquinone

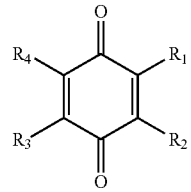

Formula VII

Formula VII demonstrates a chemical compound formula wherein R1, R2, R3, and R4 of the resultant compound are separately and independently chosen from the chemical moiety group consisting of hydrogen, alkyl, aryl, heteroaryl, amino, amido, carboxyl, hydroxyl methyl, carbonyl, ether and alkoxy ether, and wherein further any two adjacent groups (R1 and R2, or R3 and R4) may together form a substituted or unsubstituted aryl or heteroaryl ring.

In other aspects, the sensor of the present invention comprises azobenzene or azobenzene derivative described by formula VIII, shown in Table 9.

TABLE 9

Azobenzene

Formula VIII

[Structure of azobenzene with substituents $R_1$, $R_2$, $R_3$, $R_4$, $R_5$, $R_6$, $R_7$, $R_8$, $R_9$, $R_{10}$]

Formula VIII demonstrates a chemical compound formula wherein R1, R2, R3, R4, R5, R6, R7, R8, R9 and R10 of the resultant compound are separately and independently chosen from the chemical moiety group consisting of hydrogen, alkyl, aryl, heteroaryl, amino, amido, carboxyl, hydroxyl methyl, carbonyl, ether and alkoxy ether, and wherein further any two adjacent groups (R1 and R2, or R2 and R3, or R3 and R4, or R4 and R5, or R6 and R7, or R7 and R8, or R8 and R9, or R9 and R10) may together form a substituted or unsubstituted aryl or heteroaryl ring.

In another aspect, the sensor of the present invention comprises one or more redox-active molecules or derivatives thereof whose sensing ability may be enhanced by using the same derivatization strategy described for the enhancement of the pH sensing performance of AQ. Therefore, substitution of the parent molecule with polar groups with or without a spacer moiety between the polar group and the parent molecule at one or more of the available sites for substitution, including but not limited to amino, amido, carboxyl, hydroxyl methyl, and carbonyl classes of functional groups may be incorporated to improve the signal longevity and peak stability using redox-active molecule derived WE constructs. Substituents such as beta-naphthol groups attached at one or more positions of the parent redox-active molecule with or without a spacer moiety between the beta-naphthol and the parent redox-active molecule may likewise be incorporated to improve the signal longevity and peak stability of the invention.

In some embodiments, the sensors of the present invention comprises a single ASM. For example, some embodiments of single ASM pH sensors comprise sensors in which the ASM is selected from the group of compounds consisting of 2-carboxy AQ (1), 2-N-BOCethylene diamine AQ (2), 5,12-naphthacene quinone (3), and 1-acetyl amido AQ (4). In other embodiments, a single ASM sensor comprises a sensor in which the ASM is 2-(beta-naphthol)methylanthraquinone.

In other embodiments, the sensors of the present invention comprise at least two or more ASM compounds.

Some embodiments of the present invention comprise a sensor having at least one redox-active ASM and may further comprise one or more additional ASMs and/or an AIM. Both the ASMs and AIMs may include redox-active materials exhibiting reversible redox activity with well-defined cyclic voltammetry oxidation and/or reduction peaks.

Generally, the redox potential of an ASM is sensitive to a desired analyte. Suitable materials may include, for example and without limitation: pH sensitive ASMs: anthraquinone (AQ), phenanthrenequinone (PAQ), N,N'-diphenyl-p-phenylenediamine (DPPD), anthracene, diazo-containing compounds, porphyrins, nicotinamides, including NADH, NAD and N-methylnicotinamide, quinone thiol, monoquaternized N-alkyl-4,4'-bipyridinium, RuO, and $Ni(OH)_2$, and derivatives of those compounds; CO-sensitive ASMs: ferrocenyl ferraazetine disulfide; alkaline metal cation sensitive ASMs: 1,1'-(1,4,10,13-tetraoxa-7,1-diazacyclooctadecane-7,16-diyl dimethyl), ferrocenyl thiol, and other ferrocene derivatives containing covalently attached cryptands. Suitable ASMs are described, for example, in Hammond, et al., J. Chem. Soc. Perkin. Trans. 707 (1983); Medina, et al., J. Chem. Soc. Chem. Commun. 290 (1991); and Shu and Wrighton, J. Phys. Chem. 92, 5221 (1988), each of which is incorporated herein by reference. Illustrative examples include the above ferrocenyl ferraazetine and ferrocenyl crypt, in which an ordinarily chemically insensitive redox center (ferrocene) is covalently linked to a chemical recognition site in such a way as to make its redox potential chemically sensitive. Also suitable are molecules or polymers in which the sensor and reference functionalities are covalently linked such as 1-hydro-1'-(6(pyrrol-1-yl)hexyl-4,4'-bipyridinium bis (hexafluoro-phosphate), as described by Shu and Wrighton, J. Phys. Chem. 92, 5221 (1988), incorporated herein by reference.

Some embodiments of the present invention may further include AIMs having a redox potential that is substantially insensitive to the chemical medium to which they are introduced. Such AIMs may include, for example and without limitation AIMs selected from the group comprising ferrocene, n-butyl ferrocene, $K_4Fe(CN)_6$, polyvinyl ferrocene, nickel hexacyanoferrate, ferrocene polymers and co-polymers, including ferrocene styrene copolymer and ferrocene styrene cross-linked copolymer, nickel cyclam, Ag nanoparticles dispersed on carbon, and others. Further, non-limiting examples include ferrocenyl thiol, polyvinyl-ferrocene, viologen, polyviologen and polythiophene. Other embodiments may include AIMs comprising ordinarily chemically sensitive materials which are chemically isolated, yet in electrical contact with the chemical medium or analyte sample.

In general, the teachings herein that concern ASMs are also useful for AIMs.

In some embodiments, substrate materials suitable for use in WEs of the present invention include but are not limited to carbon allotropes and derivatives thereof, transition metals, conductive metal alloys, conductive polymeric compounds and derivatives thereof, semiconductive materials and derivatives thereof, including silicon and derivatives thereof, including doped silicon and doped semiconductive materials, and additional suitable materials known to those of skill in the art.

In some aspects, the substrate comprises carbon. In some embodiments, the substrate comprises a composite material comprising graphite and a binder, such as an epoxy, as described in the examples below.

In some aspects of the invention, the surface of the substrate is purified prior to attachment of the redox-active materials to improve association with the substrate, and in particular, to improve the amount and purity of material that becomes associated with the substrate, as well as the strength of association. Suitable methods for graphite/epoxy substrates and other substrates include but are not limited to sanding the surface of the substrate, which may be formed into a plug, followed by directing a stream of pressurized air or other gas onto the substrate surface, and optionally sonicating in a suitable solvent or treating the substrate surface with Aqua Regia. The resulting WE produces an analyte-dependent signal having superior signal intensity and longevity as compared to the signals produced by WEs made using a substrate that is not purified prior to ASM attachment.

A substrate acts as a self-contained entity that serves as a physical and electrical bridging unit between one or more ASMs and an electrical conduit, such as a wire. The physical function of the substrate is to provide a support for the ASMs such that the substrate/ASM construct may be immersed in a sample of interest, typically a liquid. The substrate thereby allows the ASMs to interact with the sample of interest. The electrical function of the substrate is to propagate charge carriers such as electrons from the electrical conduit to the ASM and subsequently deliver (or remove) the electrons to the ASM such that the ASM undergoes a redox reaction. In some embodiments, a substrate material is selected to include an electrical inertness towards direct reaction with the sample of interest and an ability to conduct charge carriers of various energies with a minimal loss of energy.

A variety of substrates are suitable for use in the sensors of the invention. Such substrates include but are not limited to noble metals such as gold and platinum, semiconductive materials such as silicon, and various carbon-based materials.

A variety of carbon substrates are suitable for use in the sensors of the present invention, including but not limited to carbon allotropes such as pyrolytic graphite (PG), graphite, amorphous carbon, carbon black, single- or multi-walled carbon nanotubes, glassy carbon, boron-doped diamond, pyrolyzed photoresist films (PPFs), and others known in the art. Additionally, all of the above carbon allotropes may be dispersed in powder form in a suitable binder. Such binders include organic or inorganic polymers, and adhesive materials. In some embodiments, the substrate is graphite powder and the binder is epoxy resin. In other embodiments, the substrate is a graphite rod.

In various embodiments, the substrate surface may be unpolished or polished. In one embodiment, the substrate surface is polished as described in the examples below. In other embodiments, the substrate is derivatized to facilitate adsorption or covalent attachment of the ASM to the substrate surface. Examples of suitable techniques for derivatizing the carbon substrate surface include but are not limited to oxidation, reduction, introduction of heteroatoms such as nitrogen, oxygen, or sulfur, and passivation via reaction with electrophilic or nucleophilic reagents such as methyl iodide or methyl Grignard reagents.

Several methods are available to bring the ASM into contact with the substrate in such a way that an electrical signal will be generated during the voltammetric measurement provided by the device described in this invention. The ASM may be physisorbed onto the surface by deposition, either neat (i.e. by abrasive immobilization of a solid ASM onto the substrate surface) or as a solution of the ASM in a solvent followed by evaporation of the solvent. The ASM may also be attached covalently to the surface of the substrate using covalent attachment chemistries. Examples of covalent attachment chemistries include but are not limited to, direct alkylation of nucleophilic functionalities inherent to the substrate, reactive radical addition of an ASM derivative to the substrate, reactive nitrene addition of an ASM derivative to the substrate, reactive carbene addition of an ASM derivative to the substrate and Huisgen 1,3-dipolar cycloaddition of an ASM derivative with a functionalized substrate.

When, at least in part, the substrate surface is comprised of nucleophilic functionalities, it is possible to covalently attach the ASM by direct alkylation of the surface. A non-limiting example, shown in Table 10, includes alkylation of surface hydroxyl functionality by treatment of the substrate with an ASM derivatized with a suitable leaving group (e.g. halogen or pseudohalogen) in the presence of a suitable base (e.g. Hünig's base).

TABLE 10

Direct Alkylation of Substrate

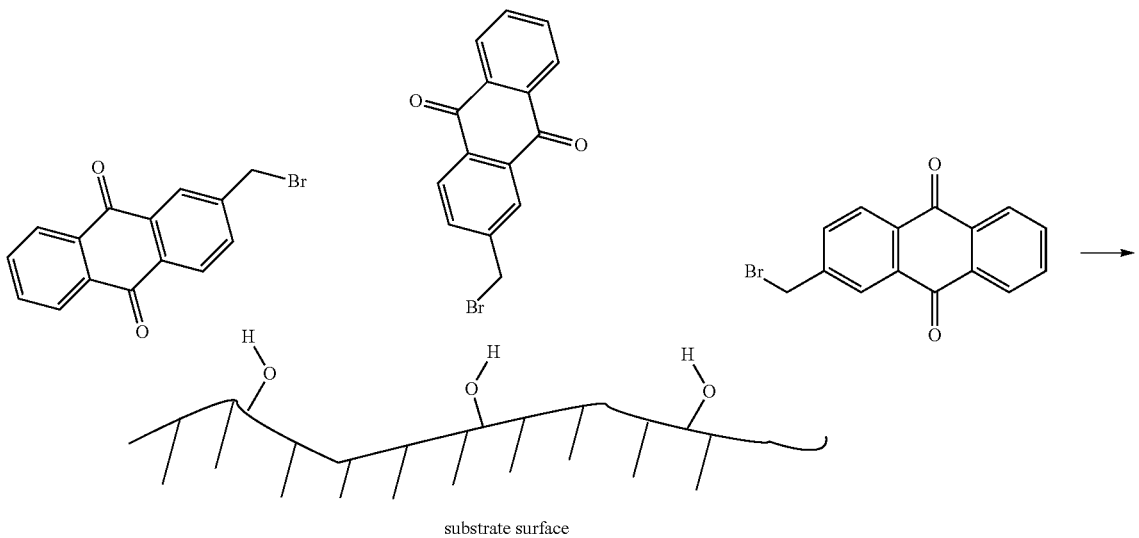

TABLE 10-continued

Direct Alkylation of Substrate

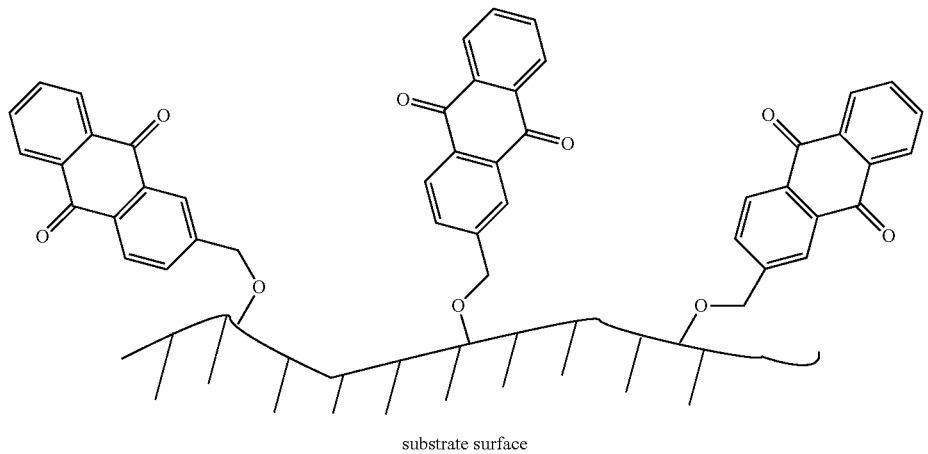 [SMILES: COCc1ccc2c(c1)C(=O)c1ccccc1C2=O ; COCc1ccc2c(c1)C(=O)c1ccccc1C2=O ; COCc1ccc2c(c1)C(=O)c1ccccc1C2=O]

substrate surface

Certain substrates are covalently modified by attachment via reaction with a reactive radical. A non-limiting example, shown in Table 11, includes generating an aryl radical electrochemically from an ASM diazonium derivative.

TABLE 11

Reactive Radical Addition to Substrate

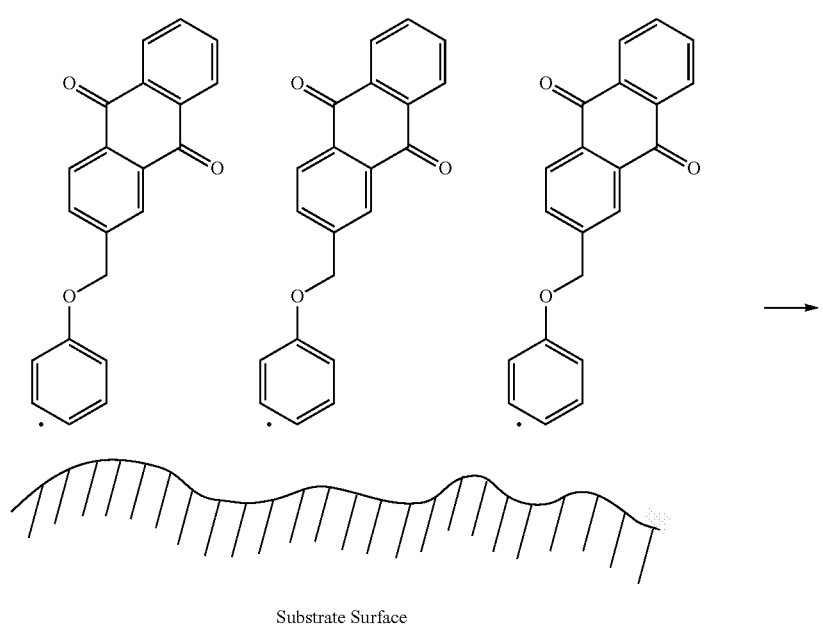 [SMILES: O=C1c2ccccc2C(=O)c2cc(COc3ccccc3)ccc21 ; O=C1c2ccccc2C(=O)c2cc(COc3ccccc3)ccc21 ; O=C1c2ccccc2C(=O)c2cc(COc3ccccc3)ccc21]

Substrate Surface

TABLE 11-continued

Reactive Radical Addition to Substrate

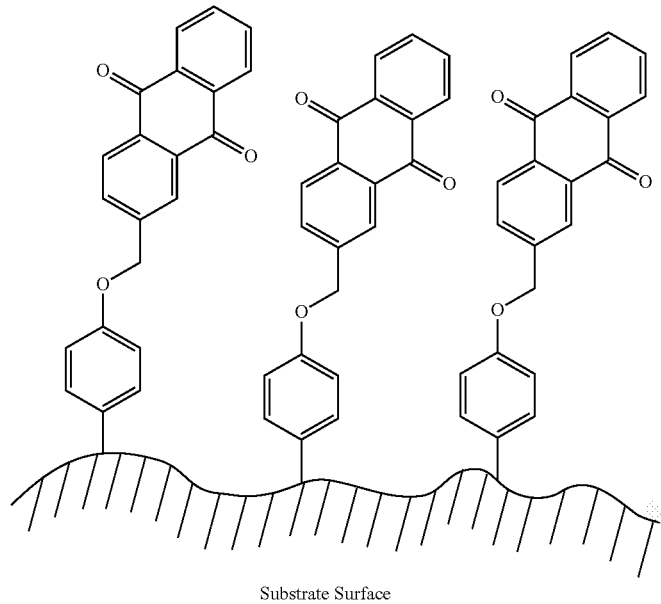

Substrate Surface

Certain substrates can be covalently modified by attachment via reaction with a reactive nitrene. A non-limiting example, shown in Table 12, includes generating a reactive nitrene thermally (i.e. by heating the substrate/nitrene precursor mixture to a suitable temperature) from an ASM azide derivative.

TABLE 12

Reactive Nitrene Addition to Substrate

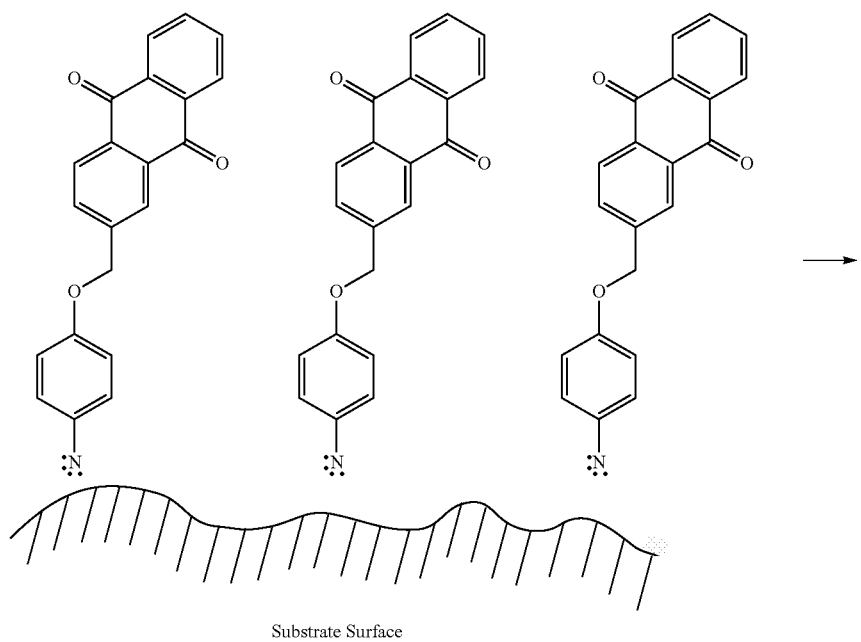 [SMILES: Nc1ccc(OCc2ccc3c(c2)C(=O)c2ccccc2C3=O)cc1 ; Nc1ccc(OCc2ccc3c(c2)C(=O)c2ccccc2C3=O)cc1 ; Nc1ccc(OCc2ccc3c(c2)C(=O)c2ccccc2C3=O)cc1]

Substrate Surface

TABLE 12-continued

Reactive Nitrene Addition to Substrate

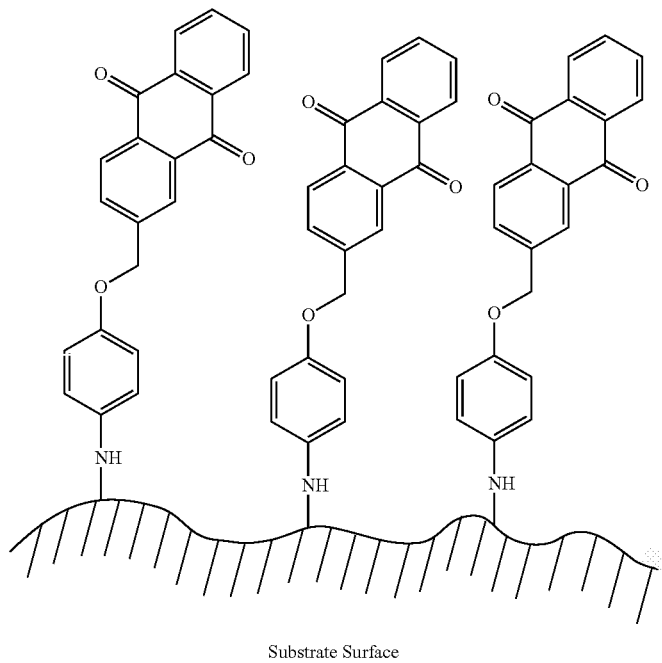

Substrate Surface

Certain substrates can be covalently modified by attachment via reaction with a reactive carbene. A non-limiting example, shown in Table 13, includes generating a reactive carbene thermally (i.e. by heating the substrate/carbene precursor mixture to a suitable temperature) from an ASM diazirine derivative.

TABLE 13

Reactive Carbene Addition to Substrate

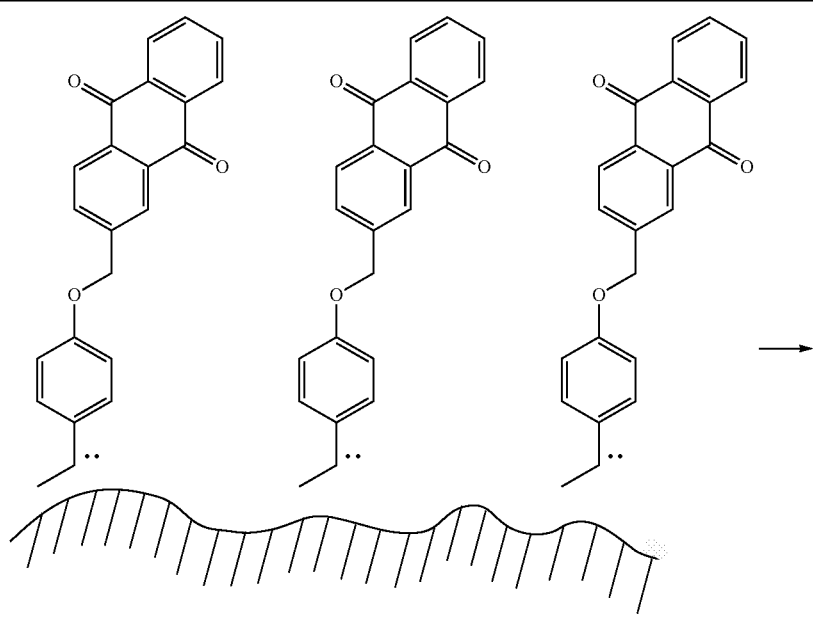

Substrate Surface

TABLE 13-continued

Reactive Carbene Addition to Substrate

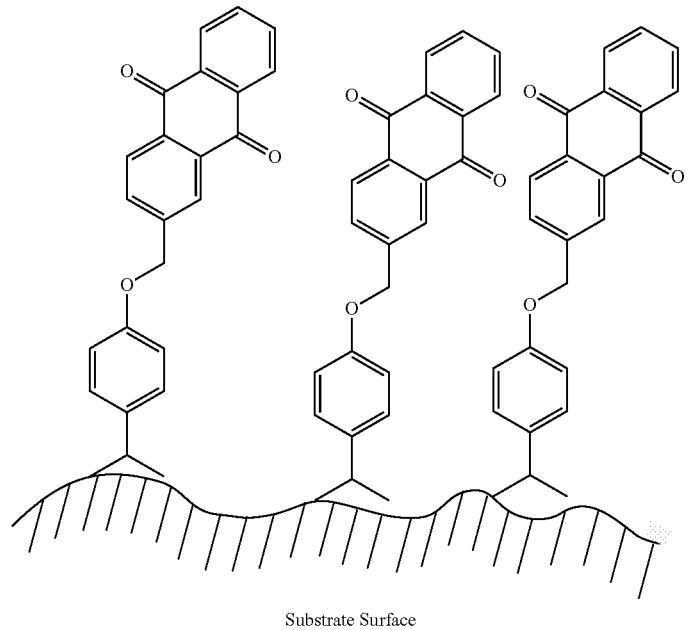

Substrate Surface

Furthermore, certain substrates can be covalently modified by attachment via Huisgen 1,3-dipolar cycloaddition. A non-limiting example, shown in Table 14, includes functionalization of the substrate surface with azides followed by Huisgen 1,3-dipolar cycloaddition with an ASM alkyne derivative.

TABLE 14

Huisgen 1,3-Dipolar Cycloaddition to Functionalized Substrate

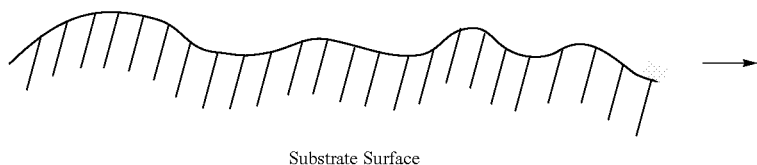

Substrate Surface

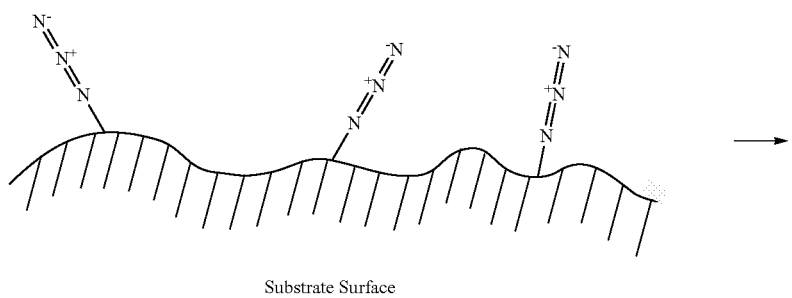

Substrate Surface

TABLE 14-continued
Huisgen 1,3-Dipolar Cycloaddition to Functionalized Substrate
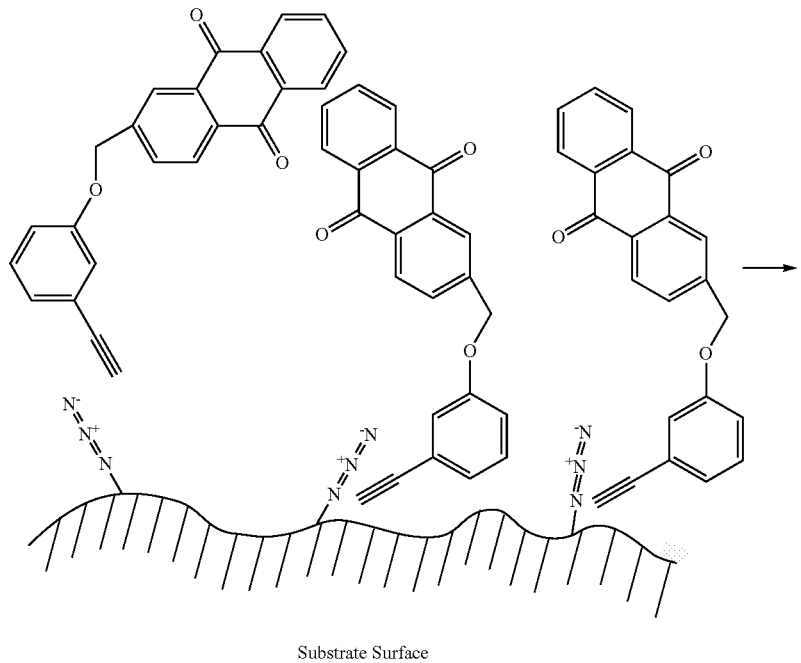
Substrate Surface
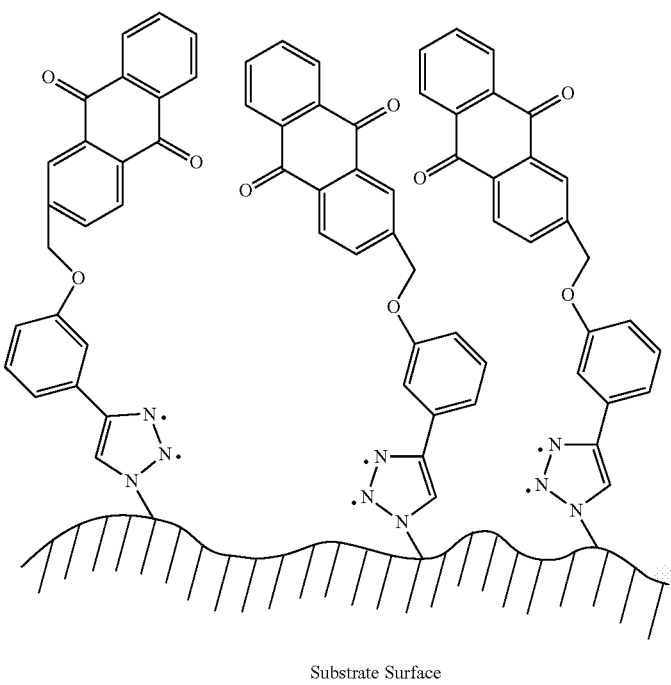
Substrate Surface Thus, the ASMs of the present invention are disposed on a desired substrate so as to be in electrical contact with it. Attachment may be accomplished by any one or a combination of means which include but are not limited to physical adsorption or covalent bonding. The ASM may be attached directly to the substrate, which may be in either a native or activated state, or may be attached by means of an intermediate material which facilitates it, such as a chemical linker. In some embodiments, the ASM is physically adsorbed to the polished surface of a graphitic rod substrate, as illustrated in the examples below.

Examples

WE ASM Example 1

Assessment of Sensor Lifetime and Accuracy as a Function of Sensor Lifetime Via a Comparative Study of Signal Intensity Decay and Signal Peak Position Stability among AQ and Selected AQ Derivatives In order to determine the improvement in lifetime and accuracy during the sensor lifetime of a series of sensor constructs, a study of the rate of signal decay and change in signal peak position as a function of time was performed using pH sensors constructed as described below having a WE comprising either AQ or one of the following compounds: 2-carboxy AQ, 2-BOCethylene diammine AQ, 5,12-Napthacene quinone, 1-acetyl amido AQ, and 2-(beta-naphthol)methylanthraquinone.

Synthesis of 2-(beta-naphthol)methylanthraquinone 2-(Bromomethyl)anthraquinone (0.225 g, 0.747 mmol) and 2-hydroxynaphthalene (0.118 g, 0.822 mmol) were taken up in acetone (10 mL). K2CO3 (0.134 g, 0.971 mmol) was added in one portion and the reaction vial was sealed. The reaction mixture was heated in a heating block (65° C.) while stirring overnight. The following morning, the reaction mixture was cooled to ambient temperature. The solution was diluted to a total volume of 40 mL by addition of DI water. The resulting precipitate was collected on a Büchner funnel. The solid was dissolved in dichloromethane (80 mL). The organic solution was washed with 1N NaOH solution (40 mL) and brine (40 mL). The organic layer was separated and dried (Na2SO4). The solution was filtered and adsorbed onto silica gel for loading onto an Isco cartridge (40 mL, silica gel). The material was purified on a CombiFlash Retrieve using a stepped gradient of hexane (300 mL), 2% EtOAc in hexane (300 mL), 4% EtOAc in hexane (300 mL), 6% EtOAc in hexane (300 mL), 8% EtOAc in hexane (300 mL) and 10% EtOAc in hexane (300 mL). The material eluted in the 8% EtOAc solvent strength fractions. The last few fractions containing the product also contained an impurity that was noticed by its yellow crystals which seemed to crystallize independently from the product crystals. These fractions were combined and evaporated, adsorbed onto silica gel and resubjected to the chromatographic separation described above. The eluent solvent strength in this case was only taken in steps to 8% EtOAc in hexanes which remained isocratic until the product was completely eluted from the column. The fractions containing the purified product were combined and condensed using a rotary evaporator. The product was obtained as a yellow solid (0.139 g, 51% yield).

WE Fabrication

A WE of the present invention was fabricated as follows. A portion of graphite rod (0.120" or 0.093" diameter, Alfa Aesar) was inserted into a plastic housing machined to accommodate less than the length, but the entire diameter of the rod with a friction fit at all points except near one end of the housing. At this end a counter bore was machined into the plastic such that there was a gap between the rod and the housing of 0.025 inches. This gap was filled with epoxy (Epotek, Billerica, Mass.) and cured according to the epoxy manufacturer's instructions. Upon curing, a 16 gauge hole was drilled in the rod on the end of the WE construct that did not contain epoxy and a 16 gauge copper wire was inserted into the hole to provide electrical contact to the carbon. The opposite end of the rod was then sanded sufficiently to give a flush plastic-epoxy-graphite surface.

The freshly sanded rod was dusted with a stream of nitrogen to remove particles and then immersed in a solution of the appropriate ASM in acetonitrile (BDH) for 3 minutes at which point it was removed, washed with acetonitrile and placed in a 150 C oven for 30 or 60 minutes. Upon cooling the WE sensor was ready for use.

Signal Acquisition Protocol

To measure the current flow to the ASM over time as a function of the applied voltage, square-wave voltammetry was performed with the WE manufactured as above using an ECHOCHEMIE AUTOLAB potentiostat/galvanometer (model PGSTAT12). A scan step size of 2 mV, an amplitude of 25 mV and a scan period of 40 ms were used. A graphite rod and saturated calomel electrode were used as the counter and reference electrodes respectively in a traditional three electrode configuration. Alternately, the measurement may be performed using the SENOVASTAT Controller processor (Senova Systems Inc., Sunnyvale, Calif.) described in U.S. Provisional Patent Application No. 61/161,139. The sensors were subjected to continuous, repetitive voltammetric scanning for approximately 4 hours in a pH 7 phosphate buffer. Each voltammetric scan represents an individual pH measurement. As each scan takes roughly 30 seconds, 500 scans were acquired in the 4 hour period. The results are tabulated in Table 15.

TABLE 15

| Results | Molecule | Peak intensity (uA) | Peak intensity signal loss over 4 hours | Peak position change over 4 hours (mV) | Peak position change over 4 h (pH) |
|---|---|---|---|---|---|
| [structure: anthraquinone-2-carboxylic acid] | 2-carboxy AQ | 126 | 13.50% | 2 | 0.033 |
| [structure: 2-BOCethylene diammine AQ] | 2-BOCethylene diammine AQ | 225 | 35.10% | 6 | 0.1 |
| [structure: 5,12-naphthacene quinone] | 5,12-naphthacene quinone | 172 | 36.00% | 2 | 0.033 |
| [structure: 1-acetyl amido AQ] | 1-acetyl amido AQ | 170 | 11.80% | 2 | 0.033 |
| [structure: anthraquinone] | Anthraquinone (AQ) | 137 | 51.80% | 4 | 0.067 |
| [structure: 2-(beta-naphthol)methylanthraquinone] | 2-(beta-naphthol)methylanthraquinone | 49 | 2.50% | 0 | 0 |

Sensor Lifetime

Figure 2:
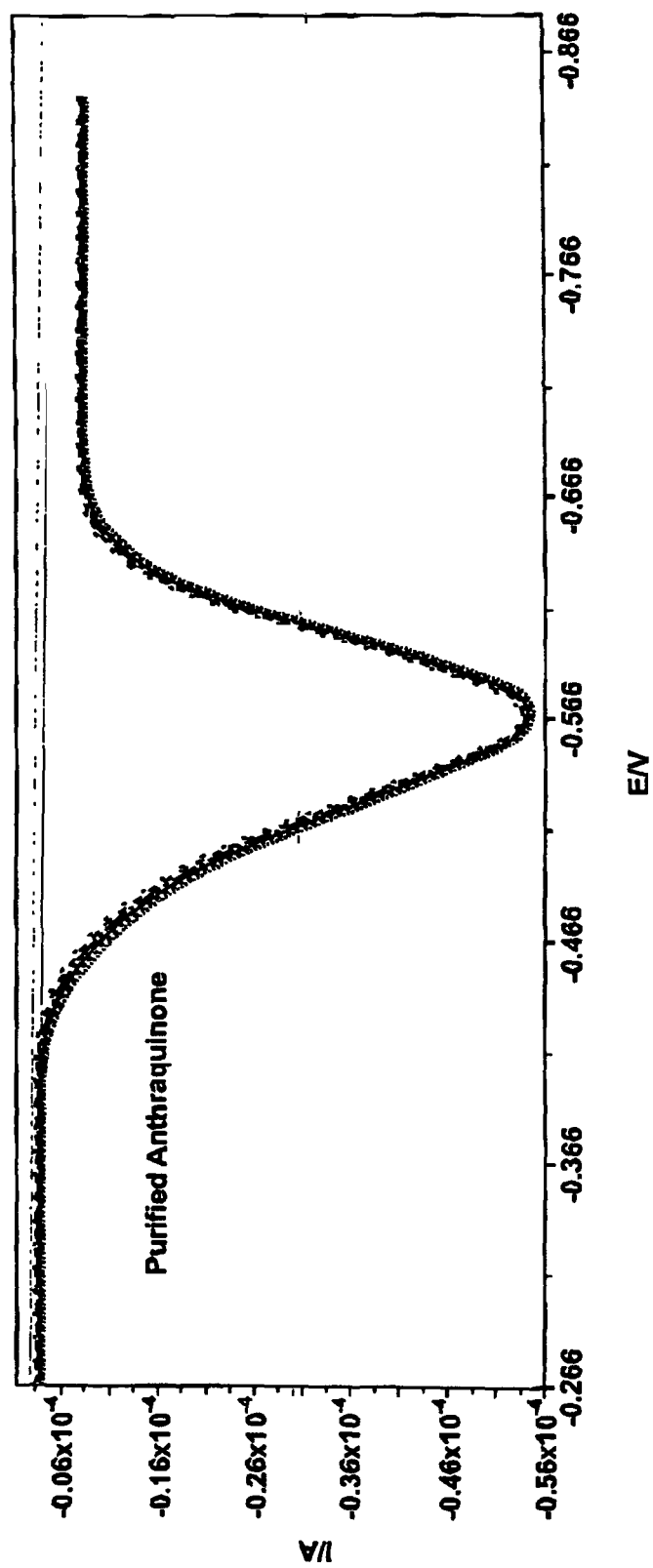
FIG. 2 shows a series of voltammograms obtained using a sensor comprising 2-(beta-naphthol)methylanthraquinone in pH 7 phosphate buffer (see Example 1 below) over the course of 4 hours. The bottom trace represents the first voltammogram with each subsequent line showing the 100th, 200th, 300th, 400th, and 500th voltammograms. As each voltammogram takes approximately 30 seconds to perform and the voltammograms were run consecutively, the time at which the voltammograms were obtained was 50 minutes, 100 minutes, 150 minutes, 200 minutes and 250 minutes for the $100^{th}$, $200^{th}$, $300^{th}$, $400^{th}$, and $500^{th}$ voltammogram respectively.

For a sensor system as described above to achieve maximal longevity, the peak intensity (the magnitude of the current at its maximum) should decrease minimally over time. The results shown in FIGS. 1 and 2 and in the column entitled "peak intensity signal loss over 4 hours" show that sensors comprising the AQ derivatives described above display less signal loss over 4 hours than does AQ. These results are significant because a decrease in signal loss results in a longer functional lifetime for the WE sensor. For example, 2-(beta-naphthol)methylanthraquinone shows a 20× improvement in signal longevity compared to AQ. This can readily be seen in a comparison of FIGS. 1 and 2 where FIG. 1 shows a marked loss in signal intensity over the course of the 500 scans for AQ while FIG. 2 shows a barely perceptible change in signal intensity over the same time period for 2-(beta-naphthol)methylanthraquinone.

Sensor Accuracy Over 4 Hours

As described above, maximal sensor accuracy throughout the sensor lifetime may be assessed by monitoring the peak position (the voltage at which the ASM current flow is maximal) as a function of time. For maximal accuracy the peak position in solutions of fixed pH should not vary. The results, shown in FIGS. 1 and 2 and tabulated in the "peak position change over 4 hours" columns, demonstrate that sensors comprising the AQ derivatives described above exhibit comparable or better peak stability than AQ over 4 hours. Importantly, sensors comprising 2-(beta-naphthol)methylanthraquinone show no peak position change over 4 hours. This means that these sensors display no loss of accuracy over the course of 4 hours compared to a change in accuracy of approximately 0.07 pH units for sensors comprised of AQ.

WE ASM Example 2

Comparison of a 2-(beta-naphthol)methylanthraquinone Sensor with a Conventional Glass Probe Some embodiments of the current invention provide the ability to measure pH for an extended period across a wide range of pH values with minimal loss in accuracy without the need for calibration of the solid state pH meter. To assess the performance of a 2-(beta-naphthol)methylanthraquinone sensor constructed as described above against that of a conventional glass pH sensor (Thermo model 9157BNMD), the pH of a series of stock buffers were measured simultaneously with both meters. While the conventional glass pH meter required calibration prior to this experiment, the sensors of the present invention could be used without calibration due to their known redox response as a function of pH. The stock buffers included: pH 4.00 (BDH 5024), pH 5.00 (BDH 5034), pH 6.00 (BDH 5038), pH 6.86 (BDH 5040), pH 7.00 (BDH 5052), pH 7.38 (BDH 5058), pH 8 (BDH 5060), pH 9.18 (BDH 5066), pH 10.00 (BDH 5078), and in 4 millimoles of acetic acid titrated from pH 3.5 to pH 12 using 50 mM NaOH. The Thermo sensor was calibrated using stock pH 4.00 phthalate (BDH 5024), pH 7.00 phosphate (BDH 5052) and pH 10.00 carbonate (BDH 5078) buffers.

Figure 3:
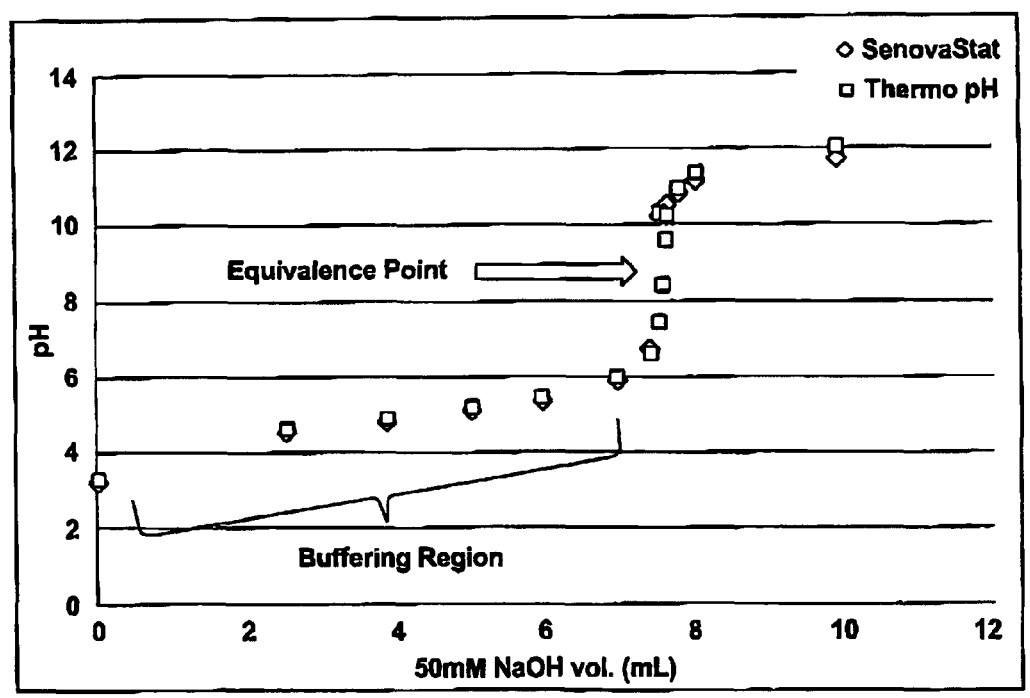
FIG. 3 compares the performance of a conventional glass pH probe with that of a sensor comprising 2-(beta-naphthol) methylanthraquinone in 4 millimoles of acetic acid titrated with 50 mM NaOH solution (see Example 2 below).
Figure 4:
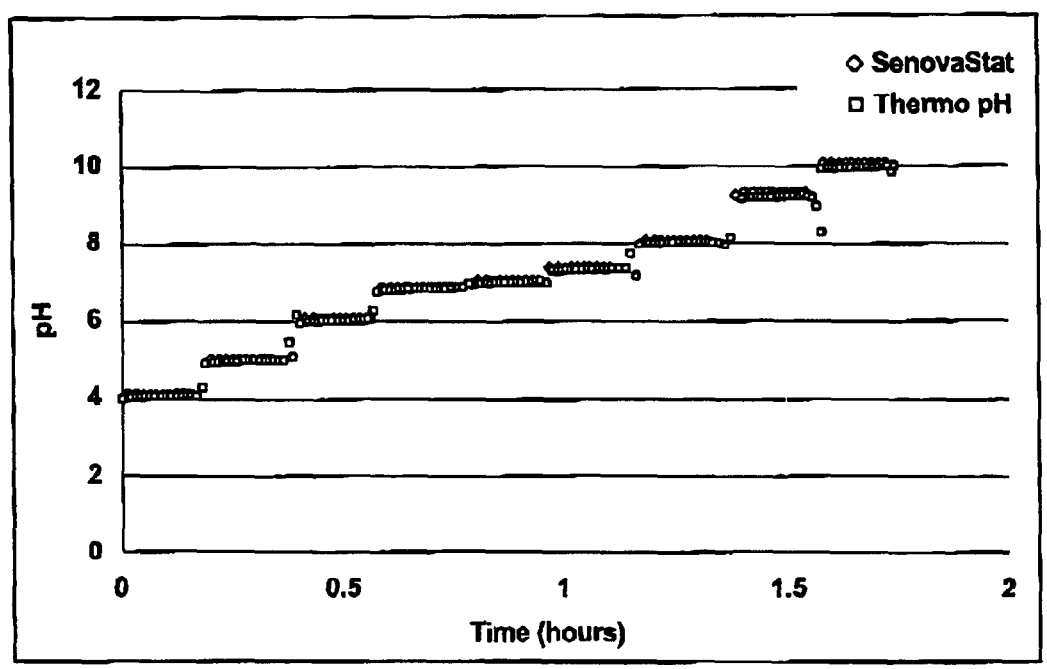
FIG. 4 compares the performance of a conventional glass pH probe with that of a sensor comprising 2-(beta-naphthol) methylanthraquinone in stock buffers over a range of pHs (see Example 2 below).

The results of this analysis, shown in FIGS. 3 and 4, demonstrate that performance of the 2-(beta-naphthol)methylanthraquinone sensor of the present invention is comparable to that of the conventional glass sensor without requiring external calibration.

Figure 11:
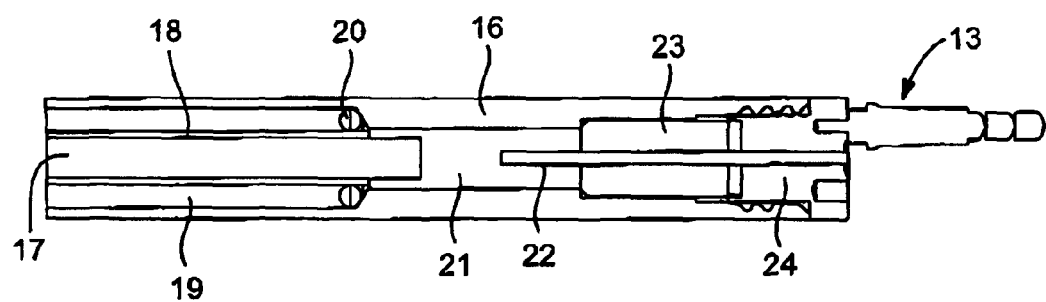
FIG. 11 is a detailed view of the exemplary embodiment of the reference electrode shown in FIG. 10.

Referring now to FIGS. 5-7 and 12, a WE 6 was formed by combining 300 mg graphite (Aldrich), 1.152 g Epoxy A and 173 mg of Epoxy B (Epotek) in a mortar and pestle and mixed till homogeneous (approximately 5 to 8 min). This material was then packed into a PEEK sensor tip housing cavity (3/16" by 5 mm deep) with a brass back plate connected to a copper wire that provides the electrical connection to the controller/processor 26, as shown in FIG. 11. The entire unit was then cured for 1 hour at 150 degrees C. in an oven. Upon removal and cooling, the surface was sanded first with 220 grit and then 1200 grit sandpaper to give a smooth, flush surface. This process provides a graphite/epoxy sensor.

Separately, $NOBF_4$ (1.1 mol eq) (Aldrich) was dissolved in DMF (BDH) at 0° C. and either 1-aminoanthraquinone (1-aminoAQ) (TCI America) or 2-aminoanthraquinone (2-aminoAQ) (Aldrich) was added (1.0 mol equivalent). The reaction was stirred at 0 degrees C. for 45 min., and then diethyl ether (5× volume equivalent relative to DMF) (BDH) was added. This afforded a pale brown precipitate (the diazonium salt of either 1-aminoAQ or 2-aminoAQ) that was collected by centrifugation, washed with diethyl ether until the washes were colorless, and then dried.

Alternatively, the diazonium salt of either 1-aminoAQ or 2-aminoAQ was formed by suspending NOBF4 (1.1 mol eq) (Aldrich) in methylene chloride (BDH) at 0° C. followed by addition of either 1-aminoanthraquinone (1-aminoAQ) (TCI America) or 2-aminoanthraquinone (2-aminoAQ) (Aldrich) (1.0 mol equivalent). The brown precipitate that resulted upon stirring was collected by filtration, washed with methylene chloride, and dried. This crude product was further purified by precipitation from DMF via the addition of diethyl ether. The precipitate was then collected by centrifugation, washed with diethyl ether until the washes were colorless, and dried.

The diazonium salt of either 1-aminoAQ or 2-aminoAQ (formed by either of the above methods) was then dissolved in DMF, and the graphite/epoxy sensor from above was immersed in this solution for 3 min. Alternatively, a drop of the diazonium-containing DMF solution was applied directly to the surface of the graphite/epoxy sensor and allowed to remain in contact with the surface for a period of time (i.e., 3 minutes). The AQ derivatized graphite/epoxy sensor was then washed with DMF and water. The resulting AQ derivatized graphite/epoxy electrode was then ready for use as a WE for pH sensing.

A suitable WE for pH sensing may also be formed by mixing epoxy with graphite or multi-walled carbon nanotubes (MWCNTs) that are derivatized with the diazonium salt of either 1-aminoAQ or 2-aminoAQ. This can be done by reacting 50 mg of graphite (Aldrich) or 50 mg of multi-walled carbon nanotubes (Nanolab) with 25 mg of the diazonium salt of either 1-aminoAQ or 2-aminoAQ (prepared as described above) in a suitable solvent. Such solvents include but are not limited to DMF, acetone, acetonitrile, water, and methylene chloride. After reaction for 1 h at room temperature, the AQ derivatized carbon materials are washed with DMF, acetonitrile, and diethyl ether and allowed to dry. The derivatized carbon materials are then mixed with epoxy, packed into a suitable PEEK housing, cured, and polished as described above.

WE ASM Example 3

Huisgen 1,3-Dipolar Cycloaddition to Functionalized Substrate Synthesis of 2-(3-ethynylphenol)methylanthraquinone 2-(Bromomethyl)anthraquinone (0.200 g, 0.664 mmol) and 3-hydroxyphenylacetylene (0.086 g, 0.731 mmol) and tetrabutylammonium iodide (0.020 g, 0.054 mmol) were taken up in acetone (20 mL). $K_2CO_3$ (0.119 g, 0.863 mmol) was added in one portion and the reaction vial was sealed. The reaction mixture was heated in a heating block (60° C.) while stirring over the weekend. The following Monday morning, the reaction mixture was cooled to ambient temperature. The solution was diluted to a total volume of 40 mL by addition of aqueous 0.1M NaOH solution. The resulting precipitate was collected on a Büchner funnel. The resulting solid was taken up in dichloromethane and was adsorbed onto silica gel for loading onto an Isco cartridge (40 g, silica gel). The material was eluted using 10% EtOAc in hexanes (500 mL) followed by 15% EtOAc in hexanes as the eluent. The fractions containing the product were combined and evaporated yielding the product as a slightly yellow solid (0.124 g, 55% yield).

Azide Functionalization of the Surface of Graphite Rod

This work follows the precedent of Devadoss and Chidsey (*J. Am. Chem. Soc.* 2007, 129, 5370-5371). $NaN_3$ (0.020 g, 0.31 mmol) was suspended in acetonitrile (10 mL). The solution was stirred at ambient temperature for 15 min. The resulting mixture (Note: $NaN_3$ is not very soluble in acetonitrile and undissolved solids were still present at this point.) was then cooled to 0° C. in an ice/water bath. After stirring in the cooling bath for 10 minutes, ICl (5 µL, 0.016 g, 0.099 mmol) was added to the vigorously stirring cooled mixture. Stirring was continued for an additional 15 minutes at 0° C. at which time the ice/water bath was removed. Four graphite rod tips, which were constructed according to the specification described herein, were suspended in the solution of $IN_3$ prepared as described above. The solution was stirred for 1 h at ambient temperature. (Note: the color of the solution went from yellow to amber over the course of this 1 h). The tips were removed from the solution and were rinsed with acetonitrile and were then used directly in the Huisgen cycloaddition without delay.

Huisgen Cycloaddition of 2-(3-ethynylphenol)methylanthraquinone with Azide Functionalized Graphite Rod A solution of $CuSO_4$ (12.8 mg, 0.08 mmol) in $DMSO/H_2O$ (3:1) (20 mL) was prepared. A solution of the tris[(1-benzyl-1H-1,2,3-triazol-4-yl)methyl]amine (2.1 mg, 0.004 mmol) in $DMSO/H_2O$ (3:1) (9 mL) was prepared. The solution of $CuSO_4$ (1 mL, 0.004 mmol) was added to the stirring ligand solution. Sodium ascorbate (15.8 mg, 0.08 mmol) was added, and the resulting solution was stirred at ambient temperature for 20 minutes. A solution (0.1 mL, 0.0002 mmol) of the 2-(3-ethynylphenol)methylanthraquinone (6.8 mg, 0.020 mmol) in $DMSO/H_2O$ (3:1) (10 mL) was added to the stirring Cu/ligand/sodium ascorbate solution. The azide functionalized graphite rod tips were suspended in the solution. The mixture was stirred for 1 h at ambient temperature. The tips were then removed and were rinsed with acetonitrile. The tips were then sonicated in acetonitrile to remove any physisorbed materials. The tips were used for electrochemical analyses without further manipulation.

Example 4

Fabrication of WE with Luer Connector

Figure 19:
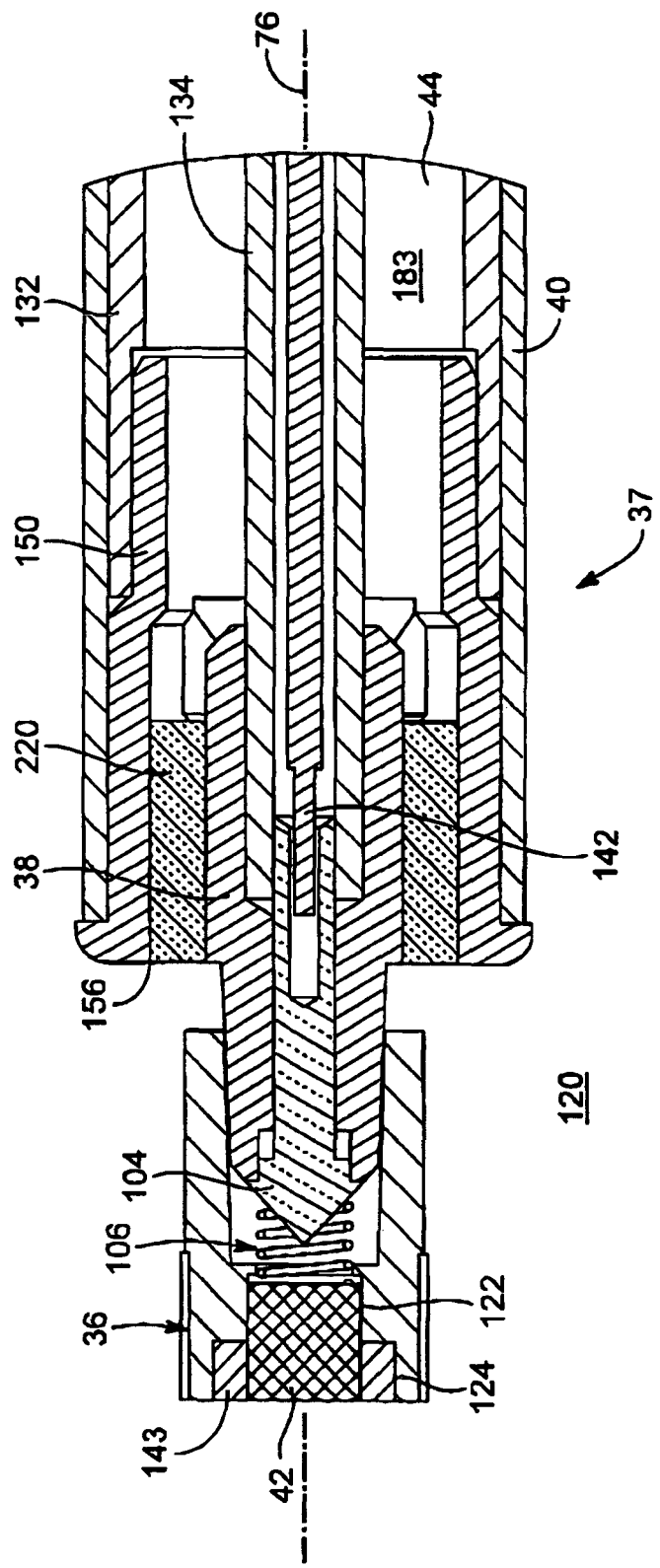
FIG. 19 is a cross-section view of an implementation of tip unit in accordance with a representative embodiment of the present invention.

A preferable WE of the present invention was fabricated as follows. Referring to FIG. 19, a gold-plated spring 106 was inserted into tip housing 36 and allowed to rest on a ledge in the tip housing. A portion of graphite rod 42 (0.120" diameter, Graphite Sales, Inc.) was then inserted into plastic housing 36 machined to accommodate less than the length, but the entire diameter of the rod with a friction fit at all points except near one end of the housing. In this arrangement the rod 42 makes direct electrical contact with spring 106. Annular gap 124 was filled with epoxy (Epotek, Billerica, Mass.) and cured according to the epoxy manufacturer's instructions. The protruding portion of the rod-epoxy construct was then sanded flat using first 220 grit and then 1200 grit sandpaper yielding a flush plastic-epoxy-graphite surface.

The freshly sanded tip was dusted with a stream of nitrogen to remove particles, immersed in acetonitrile (BDH), and sonicated for one minute to further clean the tip surface. The sonication step was repeated and the tip was then immersed into a 1 mM solution of 2-(beta-naphthol)methylanthraquinone in acetonitrile (BDH) for 3 minutes at which point it was removed, washed with acetonitrile and placed in a 150 C oven for 30 minutes. Upon cooling the WE sensor was ready for use.

The above approaches yield electrodes having better signal intensity, higher longevity, and lower levels of leaching of the AQ compound, and are simpler and cheaper to construct than those obtained by methods that involve agglomeration or physical adsorption of AQ onto carbon substrates. The above methods are also superior to methods using the commercially available, zinc chloride stabilized diazonium salt of AQ for carbon derivatization due to the larger signal intensity, higher peak position stability, and decreased reaction time.

A(1)(b): Reference Electrode (RE)

In some embodiments, the pH sensor further includes a reference electrode (RE). A number of reference electrodes suitable for use in the sensor of the present invention are known in the art. See, for example, Bard and Faulkner, "Electrochemical Methods: Fundamentals and Applications" (Wiley 2001), incorporated herein by reference.

In some embodiments of the invention, the reference electrode comprises a chloridized silver wire surrounded by an electrolytic solution, as described in the examples below. In other embodiments, the RE comprises only a chloridized silver wire. In other embodiments, the RE comprises an iodide/tri-iodide system as described in U.S. Pat. No. 4,495,050, incorporated herein by reference.

Optionally, "pseudo-reference" (PRE) (sometimes referred to as "quasi-reference") electrodes are used, particularly in non-aqueous electrolytes. An illustrative but non-limiting example of a PRE is a silver wire, commonly used in non-aqueous electrochemistry; other PREs may be used according to the particular application.

In some embodiments, the surface area of the RE exposed to the analyte sample is selected so as to minimize or eliminate intra-electrode electrochemical effects that adversely affect analyte-dependent signal quality, as described herein.

The present invention represents the first instance in which a solid-state working electrode featuring a redox-active analyte-sensitive material is operated in conjunction with a conventional reference electrode in the same pH metering system. This hybrid approach combines the robustness inherent in solid-state devices and the accepted reference standard upon which much of electrochemistry science is based.

Thus, one of ordinary skill in the art will appreciate the unique hybrid configuration of the present invention. In particular, one of ordinary skill in the art will appreciate the present combination of a solid-state WE with a traditional-based RE. This hybrid configuration provides a pH probe assembly having the reliability of a traditional-based RE without the unwanted and cumbersome calibration requirements of a traditional glass electrodes. Thus, the present invention provides a new and useful combination that overcomes the limitations of traditional pH metering systems.

In some embodiments RE is modified to include a j-hook configured, mini reference assembly, as illustrated in the examples below. A mini reference electrode is alternatively placed at the proximal end of a traditional RE such that the chloridized silver wire of the mini reference assembly is positioned adjacent or proximal to the WE of the pH sensor. The j-hook configuration of mini reference ensures that at least a portion of the RE chloridized silver wire is exposed to the temperature of the sample solution. Thus, the temperature of the wire is substantially similar to the WE, meaning that upon equilibration, the temperature of the wire varies less than 10% from the temperature of the WE. In some embodiments, the temperature of the wire varies less than 2 degrees from the temperature of the WE following equilibration of the probe assembly in the analyte-containing sample. In other embodiments, the temperature of the wire varies less than 1 degree from the temperature of the WE following equilibration of the system. Still further, in some embodiments the temperature of the wire varies less than 3 degrees from the temperature of the WE following equilibration. Subjecting the silver wire to substantially the same temperature as the WE and/or sample solution reduces the temperature sensitivity of the sensor thereby increasing the accuracy of the pH sensor.

A(1)(c): Counter Electrode (CE)

Some embodiments of the present invention further include a counter electrode (CE). In operation, the CE serves as an electron source or sink, thereby delivering current to the sample and allowing it to flow through the pH sensor system.

Suitable CEs are known in the art. See, for example, Bard and Faulkner, incorporated by reference, above. To avoid unwanted electrochemical redox processes occurring at the CE that can interfere with the signal measured at the WE, the CE is typically made of a relatively chemically inert material, commonly stainless steel, carbon (e.g., graphite) or Pt.

In some embodiments, described in the examples below, the CE is a graphite or carbon-based rod. In other embodiments the CE is a carbon-fiber tube. Still further, in some embodiments the CE is an electrically conductive material, as known in the art.

Various references describe the importance of the WE:CE surface area ratio to sensor performance. In various embodiments of the present invention, the surface area of the CE exposed to the analyte sample is selected so as to minimize or eliminate intra-electrode electrochemical effects that adversely affect analyte-dependent signal quality and longevity, as described herein. In some embodiments, the ratio of the surface area of the CE to that of the WE is from about 1:1 to about 1:10. In other embodiments this ratio is about 1:2, and in further embodiments the ratio is about 1:1.5.

In some embodiments, the CE comprises an electrically conductive carbon-fiber tube having a hollow inner lumen for housing various other components of the pH sensor. The carbon-fiber tube is electrically coupled to a preamplifier module whereby a voltage is applied to the sample solution via the CE. One skilled in the art will appreciate that, in addition to providing electrochemical cell driving potential, the electrically conductive, low-impedance CE serves as an electromagnetic shield to protect components housed within CE, especially the high-impedance RE, from external electromagnetic interference. In some embodiments, a coaxial configuration is implemented whereby an external position of the CE provides electromagnetic shielding to the RE and WE, which electrodes are concentrically or approximately concentrically positioned within the CE. One skilled in the art will further appreciate that the shielding function of the CE is not dependent upon the concentric positioning of the RE and WE. Rather, one skilled in the art will appreciate that the exact positions of the RE and WE may be internally altered relative to the external position of the CE and still receive the shielding protection as discussed above.

A(1)(d): Analyte-Insensitive Electrode (AIE)

In some embodiments of the invention, an analyte insensitive electrode (AIE) is used in conjunction with a pseudo reference electrode in lieu of the conventional reference electrode described above.

The AIE is capable of generating a substantially analyte insensitive signal in response to the application of an electrical stimulus applied to the sample being analyzed in the course of making voltammetric or amperometric measurements of analyte concentration in the sample. The AIE provides a predictable signal useful as an internal standard (in other words, a standard internal to the system) with which an analyte sensitive signal may be continuously compared, and therefore permit greater accuracy and reproducibility in determining analyte concentration.

Thus, in some embodiments of the present invention an AIE is used in the electrochemical analyte sensing device to generate a substantially analyte-insensitive electrical response when an electrical stimulus is applied to an analyte sample in the course of making voltammetric and/or amperometric measurements of analyte concentration.

A(2)(a): Coaxial Probe Assembly

Example 1 pH Sensor Assembly

Figure 14:
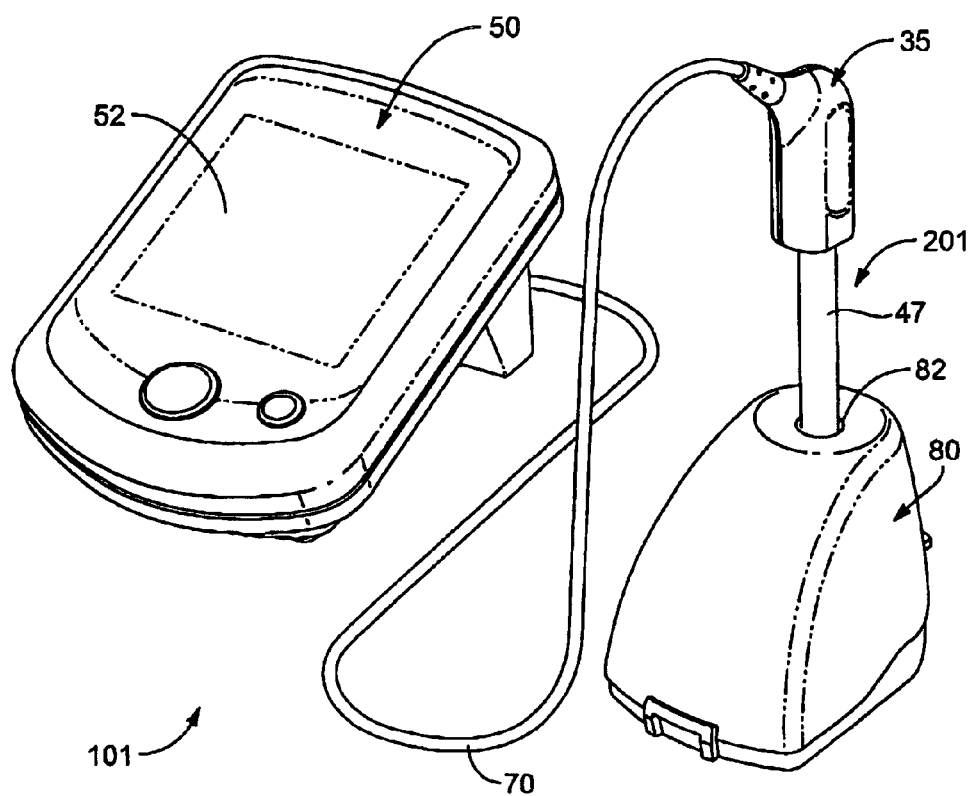
FIG. 14 is a perspective view of an implementation of a solid-state pH probe and metering device system in accordance with a representative embodiment of the present invention.
Figure 15:
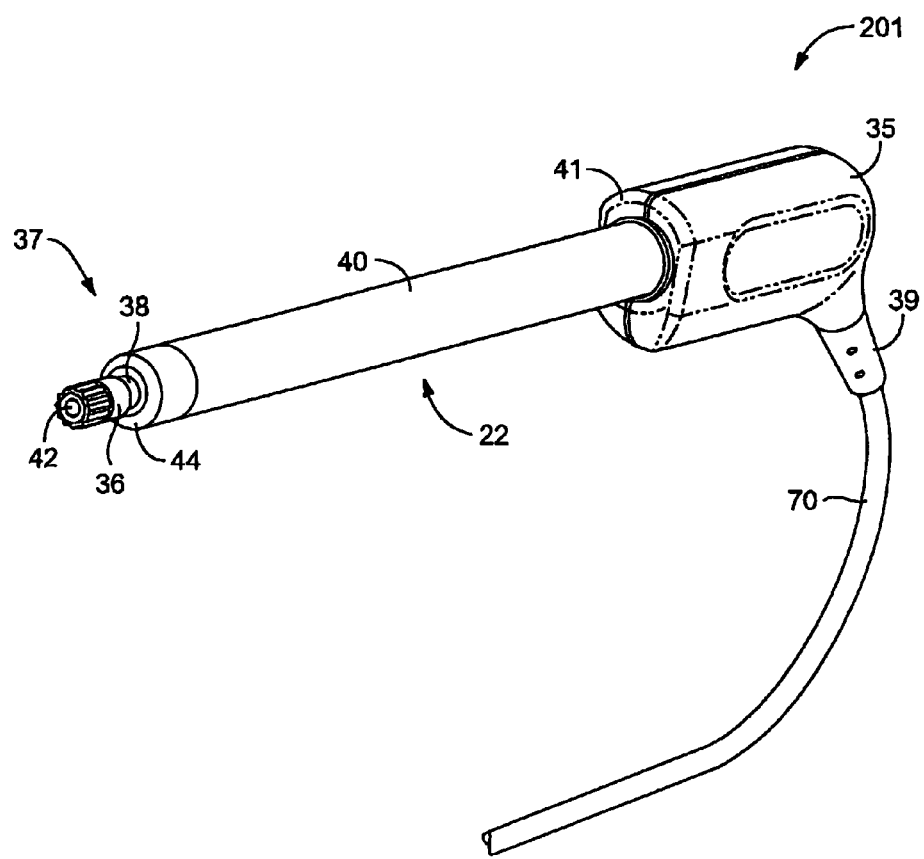
FIG. 15 is a perspective view of an implementation of a solid-state pH probe assembly in accordance with a representative embodiment of the present invention.

Referring now to FIGS. 14-19, a probe assembly 201 is provided incorporating various electrodes arranged in a coaxial configuration. In some embodiments, probe assembly 201 include a working electrode (WE) comprising a redox-active analyte sensitive material (ASM), a counter electrode (CE) comprising an electrically conductive carbon-fiber tube, and a reference electrode (RE) comprising a chloridized silver wire surrounded by an electrolytic solution, as shown in FIG. 15 and FIG. 18. The pH metering system 101 directly measures proton concentration within a sample solution by electrochemically inducing a reversible chemical reaction on the ASM of the WE. Once the WE, CE and RE are immersed in the sample solution, a voltage sweep is passed through the CE which causes the ASM of the WE to undergo a redox reaction thereby gaining or losing electrons. The resulting flow of electrons is recorded by the pH processor module.

In one aspect, the present invention provides an analyte detection device comprising at least a WE and RE in which the WE comprises an analyte sensitive, redox-active material, and the RE is a standard RE. The present invention represents the first instance in which a solid-state working electrode featuring a redox-active analyte-sensitive material is operated in conjunction with a conventional or traditional reference electrode in the same pH (or other analyte) metering system. This hybrid approach combines the robustness inherent in solid-state devices and the accepted reference electrode standard upon which much of electrochemistry science is based.

Referring now to FIG. 15, a perspective view of probe assembly 201 is shown. In some embodiments of the present invention, probe assembly 201 comprises a base enclosure 35. Base enclosure 35 generally comprises a pair of opposing halves coupled together to provide an interior space for housing various electronics to capture and amplify signals received from the tip portion 37 of the assembly 201. In some embodiments, base enclosure halves are sealed together to prevent egress of liquids in the case that the probe is accidentally submerged in liquid. In some embodiments, base enclosure 35 houses a high-gain, low-noise preamplifier where the analog signal of the probe assembly 201 is amplified for transmission to processor module 50 for further processing and display. In other embodiments, base enclosure 35 houses a high-gain, low-noise preamplifier and an analog-to-digital converter for transmission of the digital signal to processor module 50. By preamplifying the signals on-board, electromagnetic interference due to passing a high-impedance analog signal through electrical cable 70 is eliminated. Thus, the signal to noise ratio is increased in the processor module 50.

Base enclosure 35 further comprises a distal end 39 having an opening for receiving and supporting electrical cable 70. A proximal end 41 of base enclosure further includes an opening for receiving and supporting counter electrode (CE) 40. In some embodiments CE 40 is fixedly coupled to proximal end 41 via an adhesive component, such as an epoxy, wherein a portion of CE 40 maintains contact with the electronics housed within enclosure 35.

CE 40 comprises an electrically conductive carbon-fiber tube having a hollow inner lumen for housing various other components of the probe assembly 201. CE 40 is electrically coupled to processor module 50 via electric cable 70 and the various electronics housed within base enclosure 35. In some embodiments, the external cylindrical surface of CE 40 is coated with epoxy or paint except at two ends, the proximal and distal ends being exposed to approximately ⅜". By coating CE 40, the exposed proximal end electrical contact surface area is limited to the ⅜" length of exposed carbon fiber regardless of the depth to which CE 40 is submerged in liquid. At the distal end, the exposed electrical contact surface area makes contact with a connector on the printed circuit board 210. In addition, the coated surface of CE 40 electrically insulates the CE 40 to prevent interference caused by a user touching or holding the external surface of the CE 40. In addition to providing electrochemical cell driving potential, CE 40 represents a low-impedance, electrically conductive electromagnetic shield to protect components housed with CE 40 from external electromagnetic interference.

Tip portion 37 of probe assembly 201 comprises a reference electrode (RE) 44 coaxially housed within CE 40. Tip portion 37 further includes a working electrode (WE) 42 housed within a removable tip 36 mechanically coupled to a luer connector of RE 44.

Figure 16:
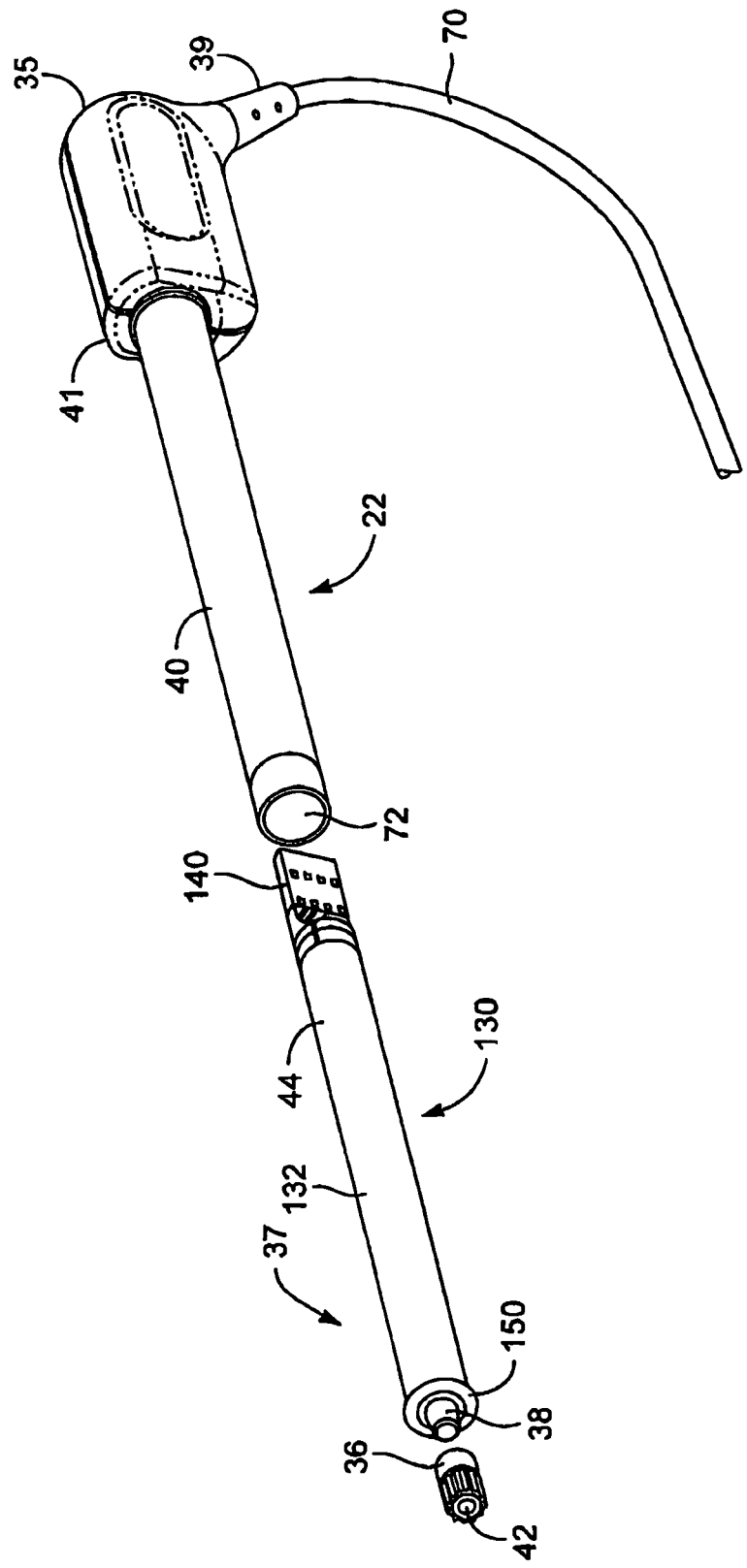
FIG. 16 is a perspective, exploded view of an implementation of a solid-state pH probe assembly in accordance with a representative embodiment of the present invention.

Referring now to FIG. 16, an exploded perspective view of probe assembly 201 is shown. As previously discussed, CE 40 comprises a hollow lumen 72 configured to house additional components of the probe assembly 201. In some embodiments lumen 72 is configured to house RE 44. RE 44 comprises a cartridge assembly 130 having a variety of structural features to receive and send signals to the electrical components housed within base enclosure 35. In some embodiments, cartridge assembly 130 comprises a tubular member 132 having an inner lumen for housing various key components of RE 44. Tubular member 132 is capped on a distal end by an electrical connector 140 configured to compatibly connect to the electrical components housed within base enclosure 35. A proximal end of tubular member 132 is sealed with a cartridge luer assembly 150 which includes a luer connector 38 for mechanically and electrically coupling removable tip 36. Removable tip 36 is reversibly pressure fitted or wedged onto the tapered outer surface of luer connector 38, such that tip 36 may be easily removed and replaced with a new tip when needed.

Figure 17A:
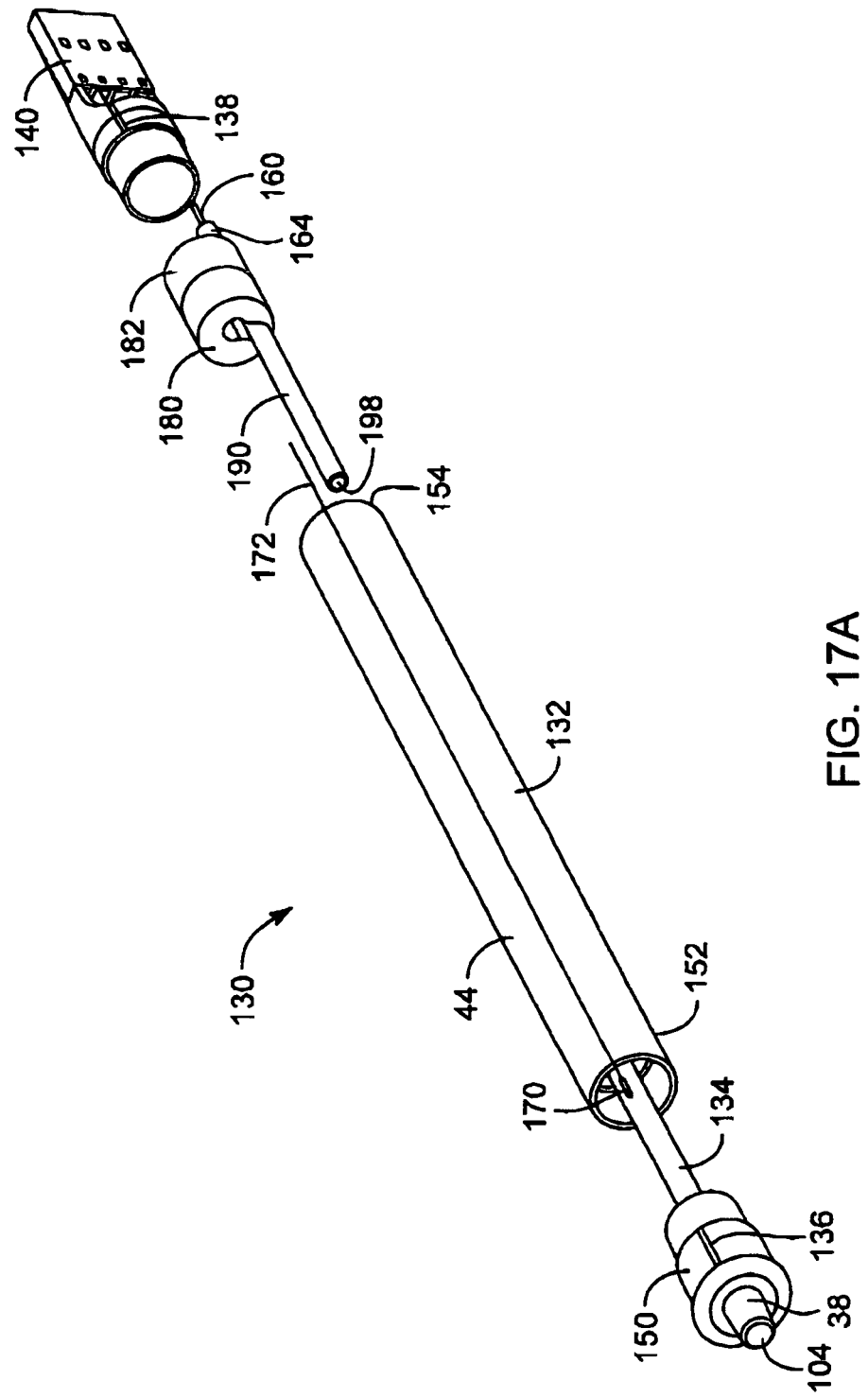
FIG. 17A is a perspective, exploded view of an implementation of a cartridge assembly in accordance with a representative embodiment of the present invention.

Referring now to FIG. 17A, an exploded perspective view of cartridge assembly 130 is shown. In general, RE 44 is based on traditional or conventional reference electrode technologies and understanding. In some embodiments, RE 44 comprises a chloridized silver wire 160 suspended within a 3M KCl gel solution, all of which is sealedly contained within an outer polysulfone tube 132. A proximal end 152 of outer tube 132 is fitted with a cartridge luer assembly 150 to form a fluid tight seal. Luer assembly 150 further includes a luer connector 38 electrically coupled to electrical connector 140 via a working electrode wire (not shown). The working electrode wire extends from contact point 104 to connector 140 through a working electrode conductor tube 134. Conductor tube 134 is fluidly sealed from the gel solution within tube 132 and is therefore isolated from any voltage applied to RE 44.

In some embodiments, luer assembly 150 is further modified to include a groove 136 to receive a thermistor 170. In some embodiments, thermistor 170 is tacked to groove 136 with an adhesive, such as with a methyl cyanoacrylate compound. During final assembly, cartridge 130 is inserted into CE 40 and sealed by means of a thermally conductive epoxy. The thermally conductive epoxy and carbon fiber tube CE 40 thermally link the thermistor to the external target solution allowing rapid and accurate temperature readings. Thermistor 170 further comprises a temperature sensor electrically coupled to connector 140 via a wire 172. One of skill in the art will appreciate that the proton activity varies with temperature and therefore the temperature of a sample solution must be taken into account when determining an accurate pH reading. Wire 172 is placed external to outer tube 132 and is routed through a groove 138 located on the outer surface of electrical connector 140. In some embodiments, wire 172 is alternatively placed within outer tube 132 and is insulated to prevent exposure to the gel solution and any voltage applied to RE 44 (not shown). Still further, in some embodiments wire 172 exits groove 138 and is directly coupled to a printed circuit board housed within base encasement 35 of probe assembly 201.

In other embodiments, RE 44 is further modified to include a double junction whereby wire 160 is preserved from contaminations within the gel solution by isolating wire 160 in a mini reference assembly 190. Mini reference assembly 190 generally comprises a casing, such as a tubular member disposed within tubular member 132, wherein a non-insulated portion of a lead or wire 160 is inserted within mini reference assembly 190. Mini reference assembly 190 also contains a 3M KCl AgCl gel solution and includes a mini frit 198 that acts as a salt bridge between the gel solution of RE 44 and mini reference assembly 190. This double junction configuration provides additional barriers between the sample solution and wire 160 thereby increasing the accuracy of the RE voltage reading.

Figure 17B:
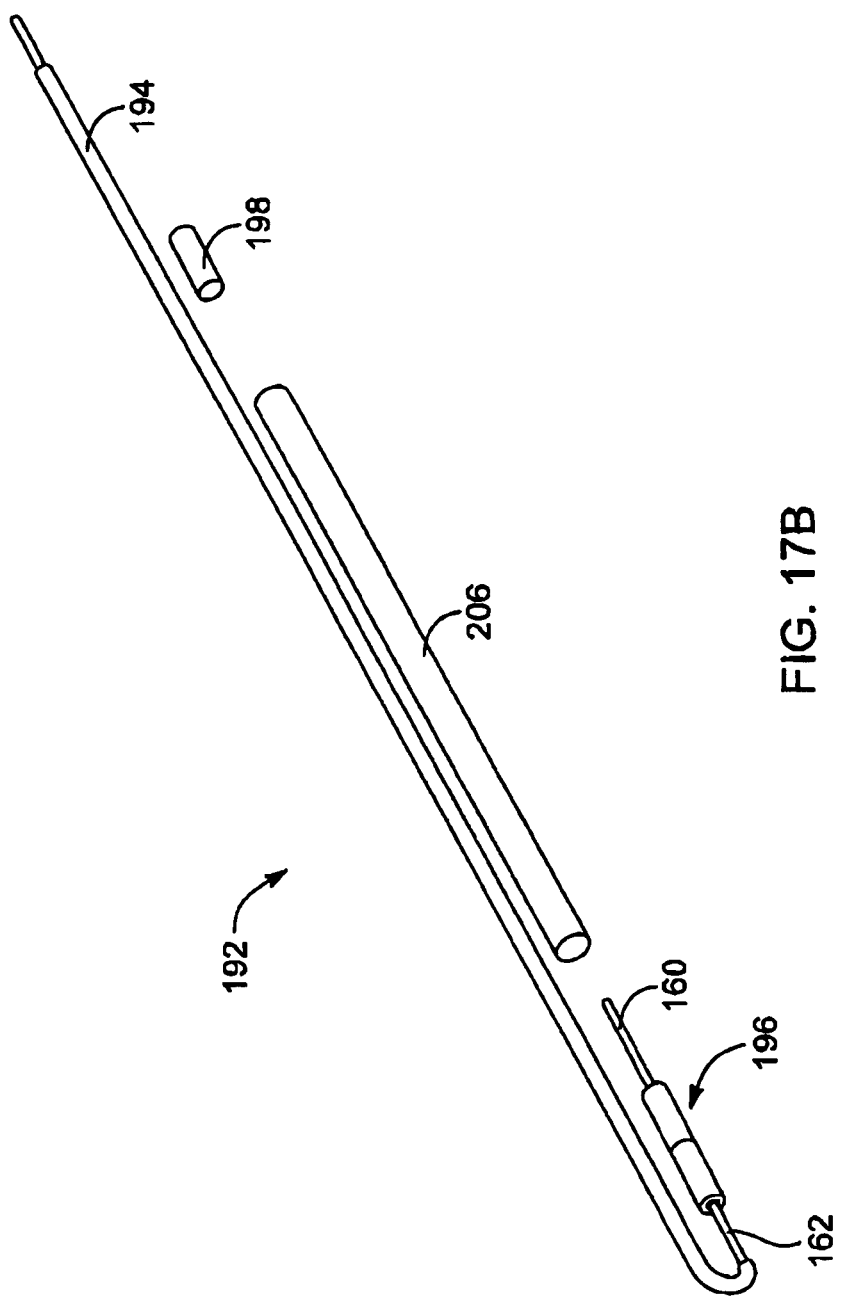
FIG. 17B is a perspective, exploded view of an implementation of a j-hook mini reference assembly in accordance with a representative embodiment of the present invention.

In some embodiments RE 44 is modified to include a j-hook configured, mini reference assembly 192, as shown in FIG. 17B. Mini reference 192 is alternatively placed at the proximal end 152 of RE 44 such that the chloridized silver wire 160 is positioned adjacent to cartridge luer assembly 150. An additional length of insulated wire 194 is attached to an exposed portion 162 of chloridized silver wire that protrudes from mini reference 192 to enable connection between mini reference 192 and electrical connector 140. The proximal end of tubular member 206 is plugged with a seal barrier 196 (which seal barrier also encapsulates exposed portion 162), while the distal end is fitted with a frit component 198, silver wire 160 being suspended in a 3M KCl AgCl gel solution within tubular member 206. The j-hook configuration of mini reference 192 ensures that at least a portion of wire 160 is exposed to the temperature of the sample solution and/or the temperature measured by thermistor 170. Subjecting the silver wire 160 to the same temperature as the sample solution reduces the temperature sensitivity of the sensor.

With continued reference to FIG. 17A, assembly of RE 44 is commenced by plugging distal end 154 of outer tube 132 with a seal barrier 180. In some embodiments, seal barrier 180 comprises foam or another material resistant to the KCl gel solution with which outer tube 132 is filled. Barrier 180 is positioned within distal end 154 so as to permit passage of conductor tube 134 and mini reference assembly 190. Distal end 154 is further sealed with a polymer sealant 182, such as a room temperature vulcanizing silicone. Finally, electrical connector 140 is fixedly coupled to distal end 154 via an epoxy or other suitable adhesive compound.

Referring now to FIG. 18, a cross-sectioned view of probe assembly 201 is shown. When assembled, electrical connector 140 is positioned within base enclosure 35 and coupled to printed circuit board 200, or a functionally equivalent electrical component. In some embodiments, printed circuit board 200 further includes circuitry 210 configured to receive, amplify and convert analog signals received from the remaining components of the assembly 201. One having skill in the art will appreciate that base enclosure 35 may be modified to accommodate any type or configuration of electronic circuitry within the spirit of the present invention.

A detailed cross-section view of the assembled tip portion 37 is shown in FIG. 19. As previously discussed, tip portion 37 is configured such that CE 40, RE 44 and WE 42 are coaxially positioned relative to one another along a common central axis 76. Specifically, CE 40 is placed at furthest from axis 76, WE 42 is centered on axis 76, and RE 44 is interposedly positioned between CE 40 and WE 42. This configuration establishes a precise spatial relationship among the three component electrodes and is inherently scalable. This configuration further establishes an equidistant spacing between the adjacent electrodes, such that a radial symmetry is maintained among the electrodes.

WE 42 is located on removable polymeric tip 36 that is mechanically connected to the end of contact point 104 via a standard taper or luer style connector 38. Tip 36 is further electrically connected to contact point 104 via a contact spring 106. Contact point 104 is fixedly and sealedly connected to conductor tube 134 and electrically coupled to electrical connector 140 via working electrode wire 142. Contact point 104 is further fixedly and sealedly connected to luer connector 38.

In some embodiments, cartridge luer assembly 150 comprises an annular recess 156 for receiving a frit member 220. In some embodiments, frit member 220 comprises a polymeric or ceramic frit having an annular shape that surrounds and is fixedly coupled to luer connector 38. Frit member 220 is positioned so as to have a proximal end in contact with a sample solution 120 and a distal end in contact with the gel solution 183 of RE 44. As such, frit member 220 acts as a salt-bridge to permit ion exchange between the sample 120 and gel solution 183 of the RE 44.

Cartridge luer assembly 150 is fixedly coupled to tubular member 132 and mechanically or reversibly coupled to CE 40. However, the mechanical connection between luer assembly 150 and CE 40 provides a fluid tight seal to prevent unwanted leakage of fluids between CE 40 and the outer surface of tubular member 132.

The connection between cartridge assembly 130 and CE 40 enables removal of cartridge assembly 130 CE 40 to permit inspection, cleaning or replacement of various components within the probe assembly 201. In some embodiments, an internal surface of base encasement 35 is modified to include directional channels (not shown) configured to compatibly align electrical connector 140 upon re-insertion of cartridge assembly into CE 40. This feature controls or assists the coupling of electrical connector 140 to the printed circuit board 200. This feature ensures proper alignment of the cartridge assembly 130 within CE 40 thereby preventing damage due to misalignment or crossed electrical connections.

In some embodiments, an annular gap 124 is provided between a proximal end of WE 42 and tip 36. In preparing WE 42, a carbon rod is positioned within opening 122 of tip 36 and then subsequently secured or fixed to tip 36 by filling gap 124 with a suitable adhesive material 143, such as an epoxy resin. WE 42 may further comprise alternative substrate materials, such as non-carbon based conductive materials, as well as those substrate materials discussed above and disclosed in U.S. Provisional Patent Application No. 61/225,855, filed Jul. 15, 2009 and entitled "METHODS AND DEVICES FOR MEASURING pH," incorporated herein by reference, in its entirety. Once the adhesive material 143 is cured, the carbon rod is sanded or otherwise shortened thereby eliminating exposure of any sidewall surfaces of the working electrode carbon material.

The carbon material is further prepared by coating the exposed surface of the carbon rod with an appropriate analyte sensitive material (ASM), as discussed above and as disclosed in U.S. Provisional Patent Application No. 61/289,318, filed Dec. 22, 2009 and entitled "IMPROVED ANALYTE SENSITIVE MATERIALS FOR USE IN A SOLID STATE ANALYTE MEASURING DEVICE," incorporated herein by reference, in its entirety. In particular, in some embodiments a 1 mM acetonitrile solution of the ASM (2-(beta-naphthol)methylanthraquinone) was dispensed onto the exposed carbon tip surface using an automated nanoliter dispenser (eVol by SGE Analytical Science) in 1 uL aliquots. Upon completion of dispensing, the coated tips were allowed to cure for 30 minutes in a 150° C. oven to provide the tips 36 in their final usable form.

One of ordinary skill in the art will appreciate the unique hybrid configuration of the present invention. In particular, one of ordinary skill in the art will appreciate the present combination of a solid-state WE 42 with a traditional-based RE 44. This hybrid configuration provides a pH probe assembly 201 having the reliability of a traditional-based RE 44 without the unwanted and cumbersome calibration requirements of a traditional glass electrodes. Thus, the present invention provides a new and useful combination that overcomes the limitations of traditional pH metering systems.

A(2)(b): Other Probe Configurations

Example 2 pH Sensor Wand Assembly

Referring now to FIGS. 5-11, in some embodiments a pH sensor is provided having a wand configuration that may be deployed into any remote vessel, for example, a bioreactor, affording the ability to constantly monitor the vessel contents for extended periods without the need for recalibration of the pH sensor. The wand was assembled as follows.

The wand assembly comprises a WE, a CE and a RE, in accordance with the teachings of the present invention. In particular, the wand assembly comprises a WE provided as described in ASM Example 2, above. A CE 8 in FIGS. 6, 7, and 9 was formed from a ¼ inch diameter graphite rod (Alfa Aesar) that was cut to 5 mm in length. The graphite rod 34 was glued to a brass backing plate in a close-fitting cylindrical cavity in a PEEK housing using silver epoxy (McMaster Carr). The dimensions of the cavity were the same as the rod. A copper wire attached to the brass backing plate provided an electrical connection to the controller/processor. Once the epoxy was cured, the graphite was sanded first with 220 grit and then 1200 grit sandpaper to give a smooth, flush surface.

This embodiment of the CE is less costly to construct than conventional platinum counter-electrodes without resulting in a sacrifice of performance, and shows less surface decomposition and hence better performance than conventional stainless steel counter-electrodes.

Further, a RE 7 as shown in FIGS. 6, 7, 10, and 11 was provided as follows. A 6 mm length of 0.5 mm silver wire (Aldrich) was placed in a silicone rubber grommet 23 and subjected to a chloridizing process that deposited a layer of silver chloride on the surface of the wire 22. The chloridizing process consisted of connecting the silver wire as a working electrode to a potentiostat (PGStat12, Ecochemie) configured to provide 250 microamps of constant current for 30 minutes in a solution of 0.1 molar hydrochloric acid (Aldrich). This provided a chloridized silver wire.

Separately, a 1/16" diameter bisque-fired porous ceramic rod 17 (CoorsTek) was retained in heat-shrink tubing 18 and fit into a housing 16 formed from a tube of Ultem plastic (McMaster Carr) that had been machined such that the inner diameter (ID) of the tube at one end was larger than the outer diameter (OD) of the heat-shrink/ceramic rod. The resulting cavity between the OD of the heat-shrink/ceramic rod and the ID of the tube was then potted with epoxy (Epoxies, Etc.) and allowed to cure. The outer surface of the ceramic rod was sanded flush to expose only a circle of ceramic. This procedure provided an Ultem housing for a porous ceramic rod wherein the rod acts as a channel through which liquid and ions may diffuse. The remaining open end of the Ultem tube was then filled with gel (saturated aqueous KCl and saturated aqueous AgCl containing high molecular weight hydroxyethylcellulose (Aldrich)) that contacted the internal terminus of the ceramic rod.

To complete the assembly of the RE, the chloridized silver wire and silicone grommet were pushed into the gel (while avoiding air bubble formation) and sealed in place using a brass screw that threaded into the Ultem housing. The brass screw also provides electrical contact between the RE and the controller/processor.

Figure 5:
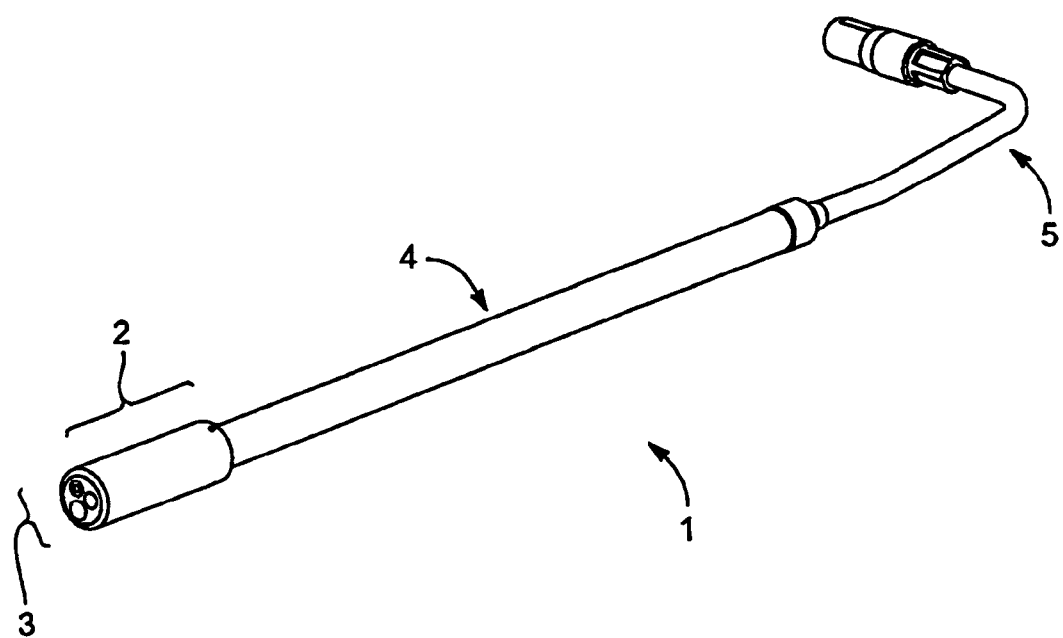
FIG. 5 shows, in fully assembled form, a first exemplary embodiment of the invention.
Figure 6:
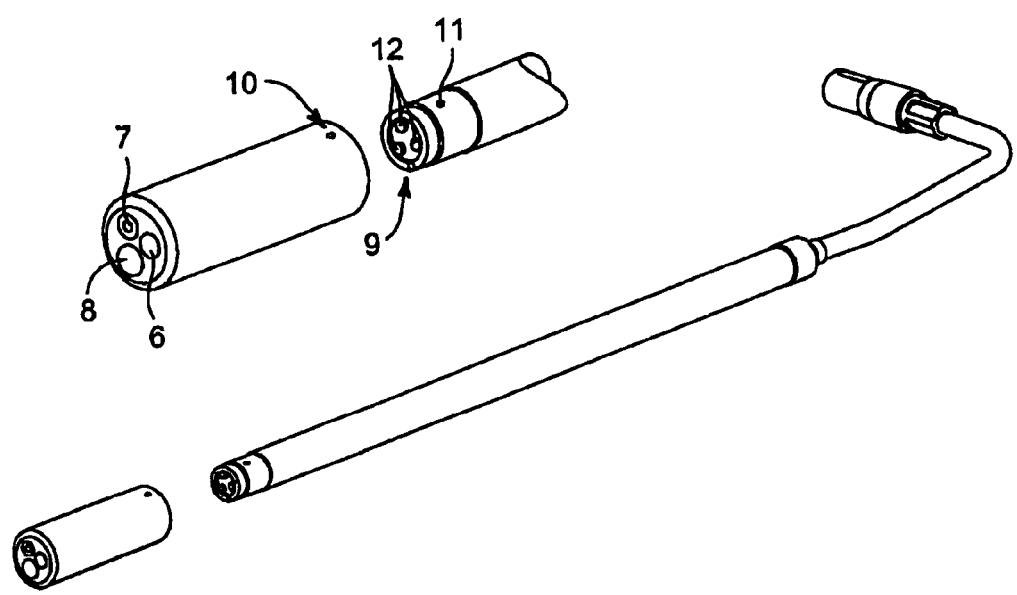
FIG. 6 shows an exploded view of the first exemplary embodiment.
Figure 8:
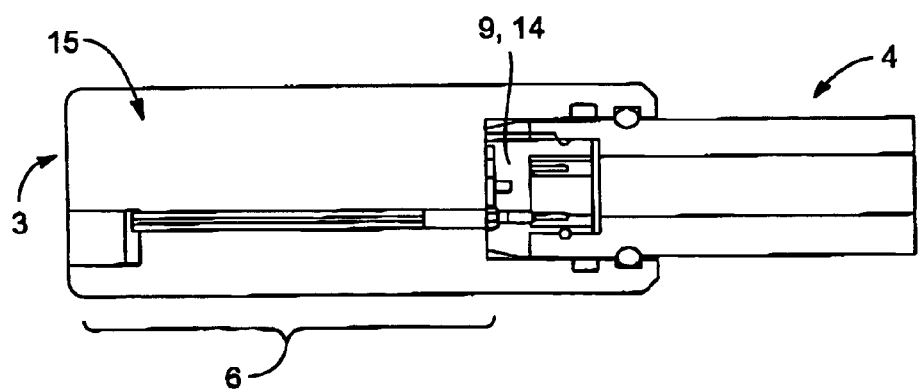
FIG. 8 is a view of an exemplary working electrode of the present invention disposed in the sensor tip of the first exemplary embodiment of the invention shown in FIGS. 5 through 7.
Figure 9:
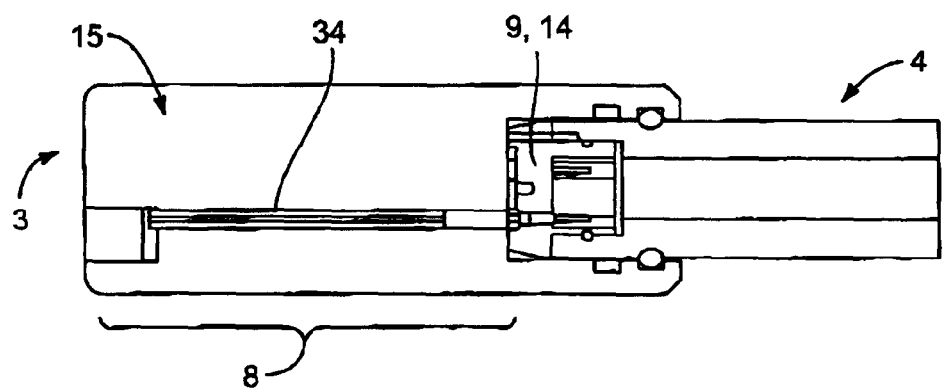
FIG. 9 is a cross-sectional view of an exemplary counter-electrode of the present invention disposed in the sensor tip of the first exemplary embodiment of the invention shown in FIGS. 5 through 7.
Figure 10:
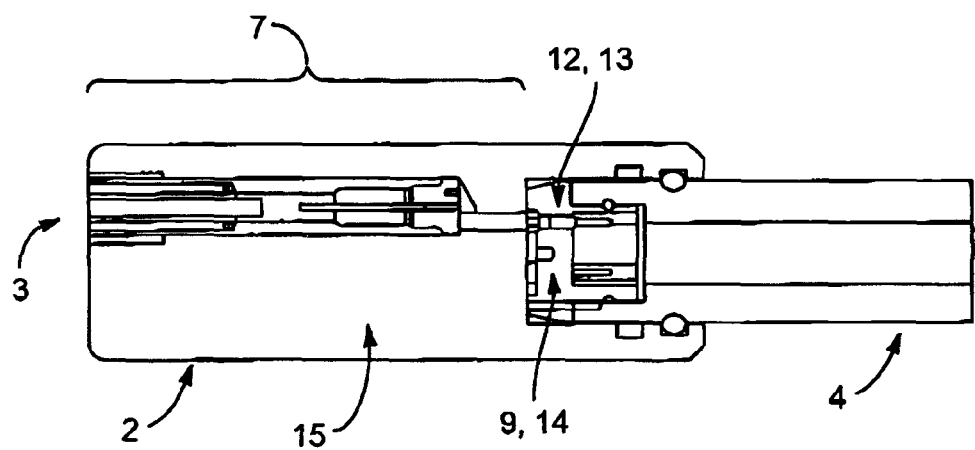
FIG. 10 is a cross-sectional view of an exemplary reference electrode of the present invention disposed in the sensor tip of the first exemplary embodiment of the invention shown in FIGS. 5 through 7.

This reference electrode has superior potential stability compared to pseudo reference electrodes, such as silver wire, and also does not require constant maintenance of electrolyte often required in conventional silver-silver chloride reference electrodes. Furthermore, the small size of this RE compared with conventional silver-silver chloride REs enables it to fit within the pH sensor tip 2, as shown in FIGS. 5, 6 and 7.

An alternative RE suitable for use in sample compositions whose chloride concentrations are constant within a range of 10% consists of a silver chloride coated silver wire wherein only the silver chloride coated portion is in contact with the sample. The remainder of the silver wire is isolated from the solution via an electrically insulating covering. Electrical contact between the RE and the controller/processor is then made via connection through the insulated silver wire. This silver chloride coated portion of the wire can be made according to the approach previously discussed for forming a chloridized silver wire. Further alternatives include replacing chloride with either bromide or iodide. These REs function effectively in sample compositions whose bromide or iodide concentrations, respectively, are constant within a range of 10%.

The alternative RE, being a coated wire, is quite easy to fabricate and as such provides a less costly and simpler reference electrode compared to those known in the art but is restricted to use in sample compositions whose halide concentrations are constant within a range of 10%.

The pH sensor tip 2 was constructed by drilling three longitudinal bores in the sensor tip housing 15 to form cavities configured to accommodate working, reference and counter-electrodes. A WE 6 was formed in the WE cavity as described above in ASM Example 2. Simultaneously, a CE 8 was assembled within the CE cavity as described above. Following formation of the WE and the CE, an RE 7 was constructed as described above and inserted in the RE cavity. This provided the sensor tip.

The pH sensor wand 1 was then assembled by fitting the sensor tip onto the sensor body 4 by first visually aligning the tip with the sensor body by means of alignment marks 10 and 11 and then sliding the tip onto the body such that the contact locator pin 9 engaged with the contact locator hole 14, thereby placing the electrode contacts 13 for the WE, CE and RE in the sensor tip in proper alignment with their corresponding contacts 12 on the sensor end of the sensor body.

In operation, the sensor wand assembly is inserted into the remote vessel and connected electrically to a controller/processor by inserting the connector/wire harness 5 into the sensor wand port of the controller/processor. The pH is then determined voltammetrically.

A(3)(a): Probe Clip

Figure 20:
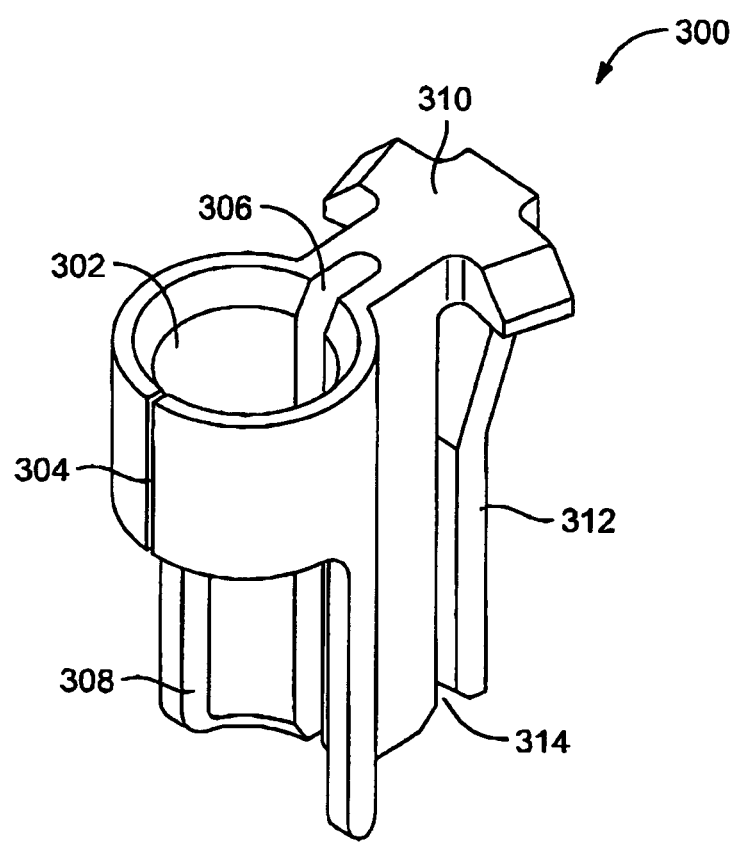
FIG. 20 is a perspective view of a probe assembly clip in accordance with a representative embodiment of the present invention.
Figure 21:
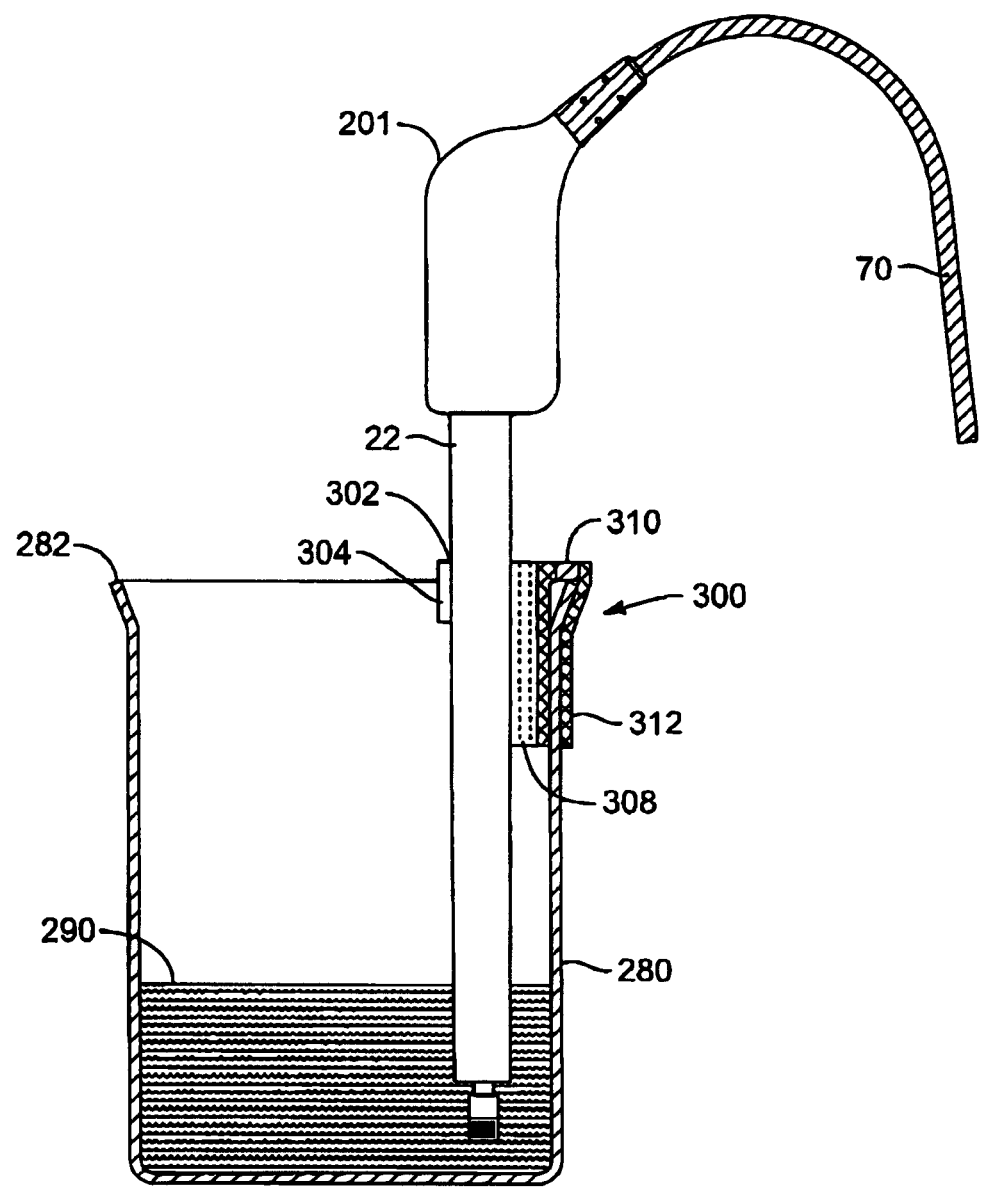
FIG. 21 is a perspective view of a probe assembly coupled to a container, shown in cross-section, via a probe clip assembly also shown in cross-section in accordance with a representative embodiment of the present invention.

Some embodiments of the present invention further include pH sensor accessories to facilitate in the storage and use of the pH sensor. For example, referring now to FIGS. 20 and 21, a probe clip 300 is shown. Probe clip 300 generally comprises a flexible or semi-rigid molded polymer material having an aperture 302 sized to compatibly receive shaft portion 47 of probe assembly 201. Probe clip 300 is provided as a means for coupling a pH probe 201 to a desired container 280 such that the tip of the probe 201 is suspended with a target solution 290.

In some embodiments aperture 302 further comprises an expansion gap 304 and/or a relief groove 306 to permit expansion of aperture 302, thereby accommodating various sizes and designs of pH probe assemblies. Probe assembly 201 is generally maintained within aperture 302 via a friction fit. In some embodiments, aperture 302 is further modified to include a texture or coating to increase friction between the two interfacing surfaces. Probe clip 300 may also include an elongate surface 308 to further stabilize the probe assembly during use. The suspended height of probe assembly 201 within clip 300 is adjusted by further insertion or retraction of probe assembly 201 within aperture 302.

Aperture 302 and elongate surface 308 are directly coupled to clip 312 via support base 310. Support base 310 and clip 312 are configured to straddle a rim 282 or exposed surface of a container 280 holding a target solution 290. In some embodiments a gap 314 is interposed between clip 312 and aperture 302 or elongate surface 308, to accommodate the wall thickness of a container. For example, gap 314 may include a width approximately equal to, or slightly narrower than the wall thickness of a container. Gap 314 may further include a contour or shape configured to compatibly receive a non-linear feature of the container's rim or lip. For example, in some embodiments gap 314 comprises a shape to receive a beveled lip of a container.

Figure 22:
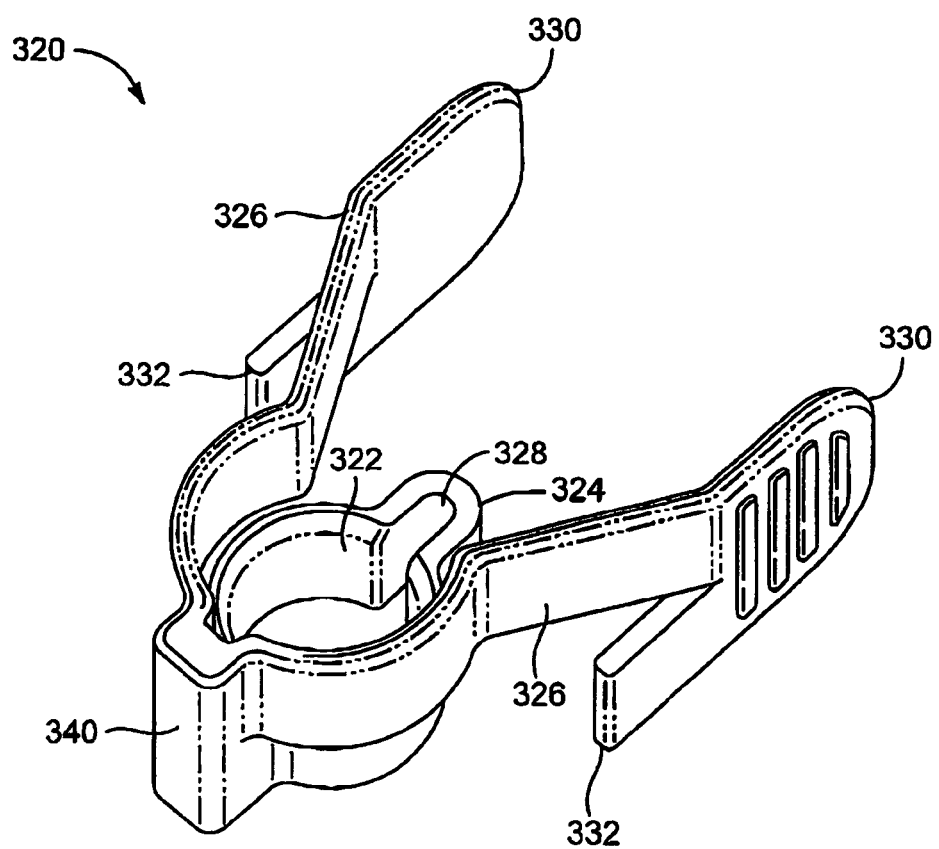
FIG. 22 is a perspective view of a probe assembly clip in accordance with a representative embodiment of the present invention.

Referring now to FIG. 22, a winged probe clip 320 is shown. Probe clip 320 comprises an aperture 322 having a relief groove 328 to permit expansion of aperture 322, thereby accommodating various sized and designs of pH probe assemblies. Probe clip 320 further includes a pair of oppositely positioned wings 330 having contact points 332 aligned generally within the same plane as aperture 322. Aperture 322 and wings 330 are coupled to one another via support base 340.

Probe clip 320 is fastened to a container by first inwardly compressing oppositely positioned wings 330 whereby contacts 332 are distracted outwardly relative to aperture 322. Upon compression of wings 330, a gap (not shown) is provided between contacts 332 and aperture contact 324. Probe clip 320 is then positioned over the rim of the container such that contacts 332 are located on an external surface of the container and aperture contact 324 is located against an interior surface of the container. Aperture contact 324 is generally positioned between contacts 332. Upon releasing wings 330, aperture contact 324 is pulled tightly against the inner surface of the container thereby securing the position of probe clip 320. Arms 326 transverse the rim of the container thereby maintaining the position of clip 320 proximal to the opening of the container.

Figure 23:
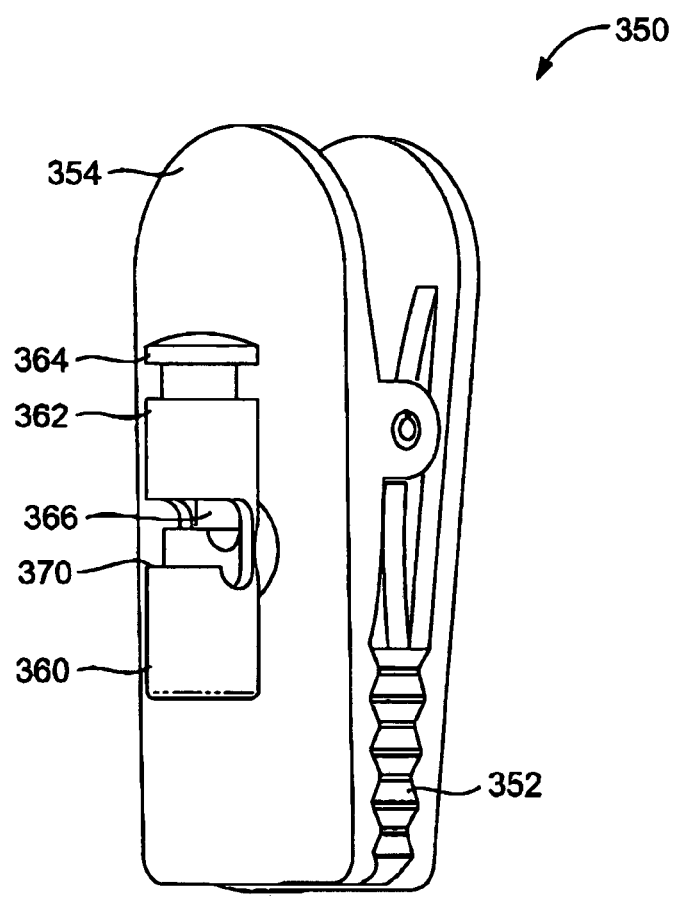
FIG. 23 is a perspective view of a probe cord clip in accordance with a representative embodiment of the present invention.
Figure 24:
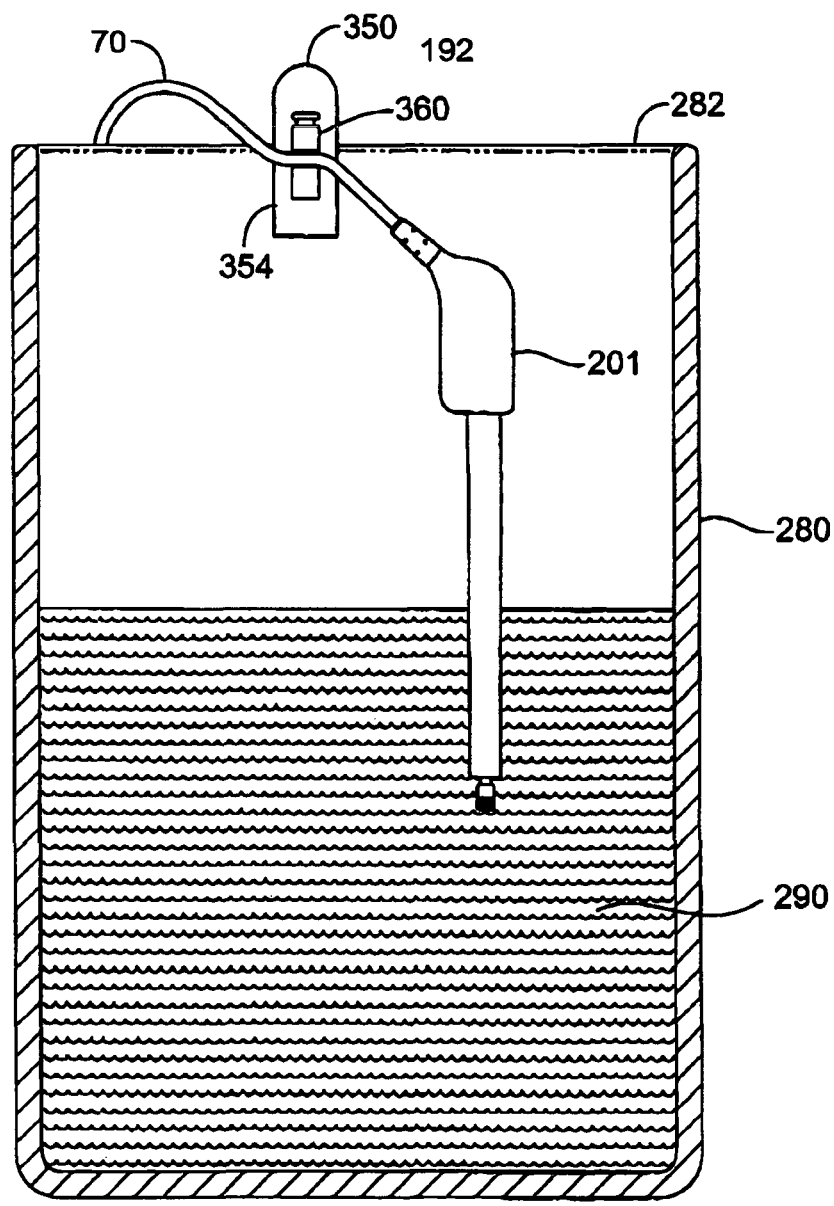
FIG. 24 is a perspective view of a probe cord coupled to a container, shown in cross-section, via a probe cord clip in accordance with a representative embodiment of the present invention.

Referring now to FIGS. 23 and 24, a cord clip 350 is shown. In some embodiments, cord clip 350 comprises a hinged clip having a mouth section 352 for receiving the edge or rim 282 of a container 280. Cord clip 350 further includes a cord catch 360 pivotally coupled to an inner arm 354 of the clip 350. Cord catch 360 is generally configured to securely maintain the position of cord 70 of probe assembly 10. In some embodiments, cord catch 360 comprises an outer barrel 362 fitted internally with a spring-loaded piston 364. Prior to activation, piston 364 is relaxed such that only a portion of the piston's cord slot 366 is exposed through barrel window 370. Upon activation of piston 364, cord slot 366 is fully exposed through barrel window 370. Once exposed, cord 70 of pH probe assembly 201 is inserted into cord slot 366 through window 370. Piston 364 is then released thereby returning piston 364 to a relaxed position, thereby causing cord 70 to be pinched or otherwise immobilized between window 370 and cord slot 366.

The suspended height of probe assembly 201 is adjusted by increasing or decreasing the distance between probe assembly 201 and clip 350. Changes to this distance are made by activating piston 364, thereby releasing the pinched or immobilized position of cord 70, followed thereafter by a readjustment of cord 70. When an appropriate suspended height is reached, piston 364 is released thereby resuming the pinched and/or immobilized position of cord 70. The pivot feature of clip 350 accommodates the hanging position of probe 201 to prevent unwanted kinking or crimping of cord 70. In some embodiments, cord catch 360 is fixedly attached to inner arm 354 at a desired angularity.

A(3)(b): Probe Inkwell

Figure 25:
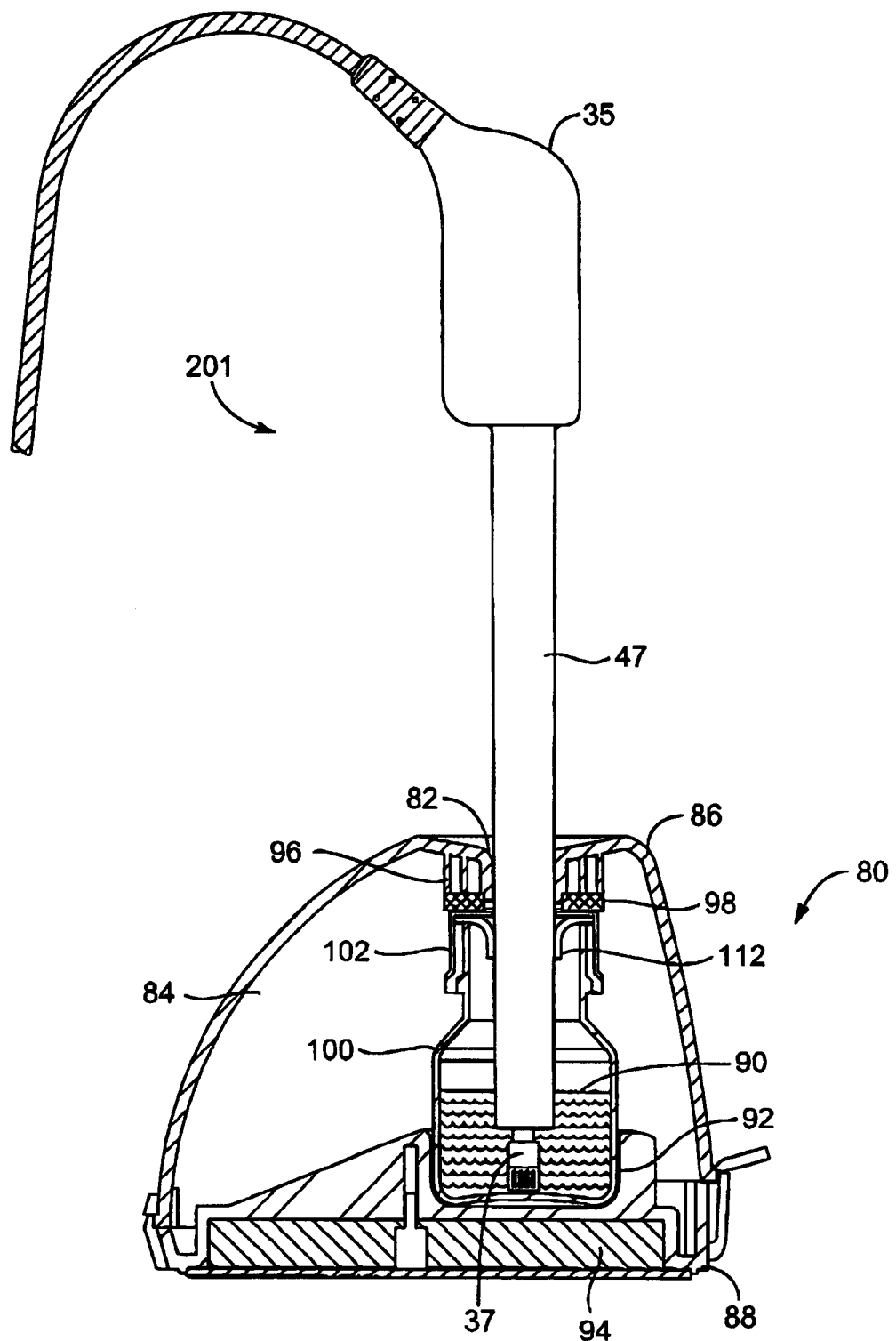
FIG. 25 is a cross-section view of an implementation of a storage base as accessed by a probe assembly, shown in perspective, in accordance with a representative embodiment of the present invention.

When not in use, the pH sensor of probe assembly 201 may be inserted into an opening 82 of a storage base 80, as shown in FIGS. 14 and 25. Storage base 80 is configured to securely hold probe assembly 201 such that base encasement 35 is held in a generally upright position. An interior space 84 of storage base 80 may be further modified to hold or otherwise retain a wetting solution 90, whereby tip portion 37 of probe assembly 201 is stored in the wetting solution 90 when inserted within opening 82, as shown in FIG. 25.

With continued reference to FIG. 25, a cross-section view of storage base 80 is shown. Some embodiments of storage base 80 comprise a clamshell configuration having an upper lid 86 hingedly coupled to bottom plate 88. Bottom plate 88 comprises a molded well 92 having a shape and diameter to compatibly receive a bottle 100 or other container for holding wetting solution 90. Bottom plate 88 further includes a base weight 94 to provide a low center of gravity thereby further stabilizing storage base 80.

Upper lid 86 further includes an inwardly molded extrusion 96 having a length calculated to firmly contact lid 102 of bottle 100. Protrusion 96 thus contacts lid 102 to maintain the position of bottle 100 within molded well 92. In some embodiments, a washer or spacer 98 is interposed between extrusion 96 and lid 102 to seal the interface and thereby prevent leakage of wetting solution 90 into interior space 84.

Figure 26:
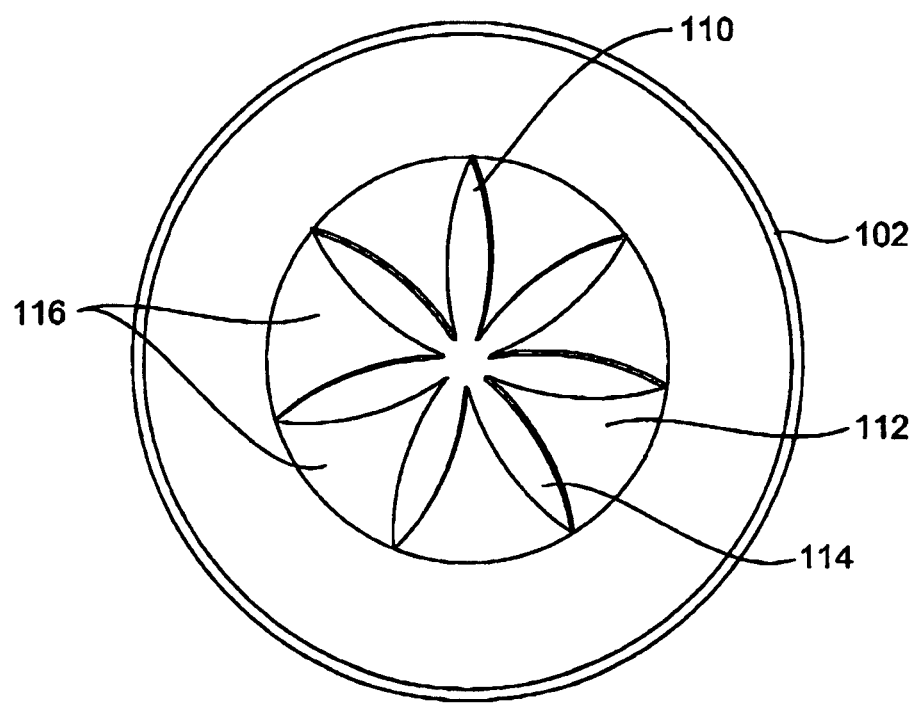
FIG. 26 is top plan view of a lid in accordance with a representative embodiment of the present invention.

Referring now to FIG. 26, a top perspective view of lid 102 is shown. An opening 110 is provided in lid 102 having a diameter slightly greater than the diameter of shaft portion 47 of probe assembly 201. Shaft portion 47 is thus permitted to access wetting solution 90 via opening 110, as shown in FIG. 25. In some embodiments, opening 110 further includes a membrane 112 having a plurality of slits 114 thereby providing a plurality of opposing flaps 116.

Membrane 112 generally comprises a resilient material that is resistant to various acidic and basic solutions for which a pH measurement would be obtained. For example, in some embodiments membrane 112 comprises a rubber or plastic polymer material. Membrane 112 further comprises a moderately elastic material such that upon removal of probe assembly 201 from opening 110, flaps 116 of membrane 112 recover their original shape or configuration to substantially close opening 110. Flaps 116 may also be configured to wipe or otherwise remove a solution from an outer surface of shaft portion 47 upon insertion or removal of probe assembly 201 from storage base 80.

The number of slits 114 and size of flaps 116 may vary as needed to accommodate probe assembly 201. In some embodiments, flaps 116 substantially close opening 110 to prevent evaporation of wetting solution 90. Flaps 116 further provide radial support to shaft portion 47 thereby centering shaft portion 47 within opening 110.

The size of flaps 116 may be further modified to prevent an airtight seal between lid 102 and shaft portion 47 during insertion of probe assembly 201 into bottle 100. An airtight seal is generally undesirable due to increased air pressure within bottle 100, which leads to positive air pressure within probe assembly 201. Positive air pressure within probe assembly 201 may lead to displacement of key components within the assembly, and should therefore be avoided. Thus, in some embodiments flaps 116 are configured to permit insertion of probe assembly 201, yet prevent an airtight seal between lid 102 and shaft portion 47.

The features of storage base 80 may generally be modified to accommodate any pH probe or glass electrode necessitating wetting of the probe's reference electrode. For example, in some embodiments opening 82 and membrane 112 are modified to accommodate a pH probe assembly having a size and configuration not taught by the present invention. It is further anticipated that embodiments of storage base 80 may further include multiple openings and multiple molded wells 92 to accommodate a plurality of probe assemblies 20 and/or wetting solutions.

A(3)(c): Sealed Packaging

Figure 27:
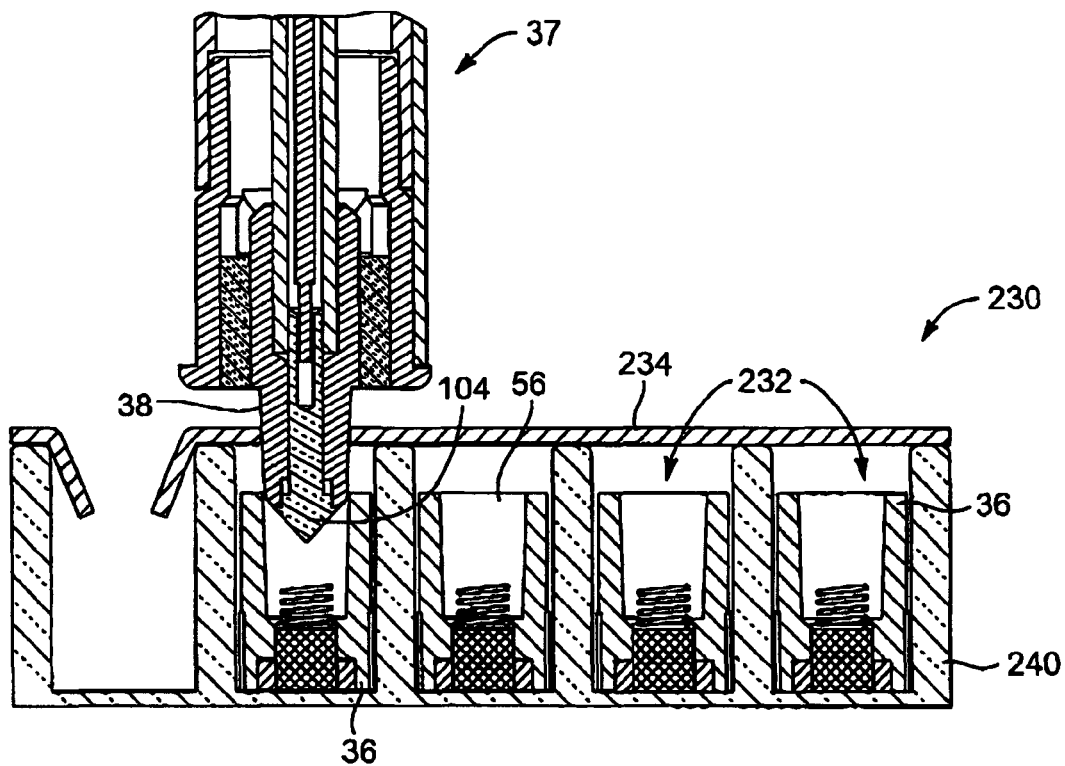
FIG. 27 is a cross-section side view of a sealed packaging assembly in accordance with a representative embodiment of the present invention.

Referring now to FIG. 27, a cross-section view of a sealed package 230 of disposable tips 36 is shown. In some embodiments sealed package 230 comprises a disposable polymer packaging having a plurality of wells 232 for storing disposable WE tips 36 prior to use. A foil lid 234 is applied to base member 240 so as to individually seal each well 232 from the surrounding environment. A tip 36 is removed from a respective well 232 by forcing contact point 104 through foil lid 234 at a position proximate to insertion site 56 of tip 36. In some embodiments, the center of each well 232 is marked on the outer surface of the foil lid 234 to provide a visual indicator of where to insert contact point 104. In some embodiments, the visual indicator includes a circle, a dot, a physical indentation, a texture, a target symbol, a color, a clear window or any combination thereof.

Foil lid 234 may include any suitable material known in the art. In some embodiments, the material and/or thickness of lid 234 is selected so as to provide a desired resistance when forcing contact point 104 though the lid 234. For example, in some embodiments the physical characteristics of lid 234 are selected such that a minimum force required to push contact point 104 though lid 234 is equal to the force needed to accurately and sufficiently seat contact point 104 within insertion sited 56. As such, the mere act of pushing contact point 104 through lid 234 generates a follow-through force sufficient to load tip 36 securely onto luer connector 38.

Figure 28A:
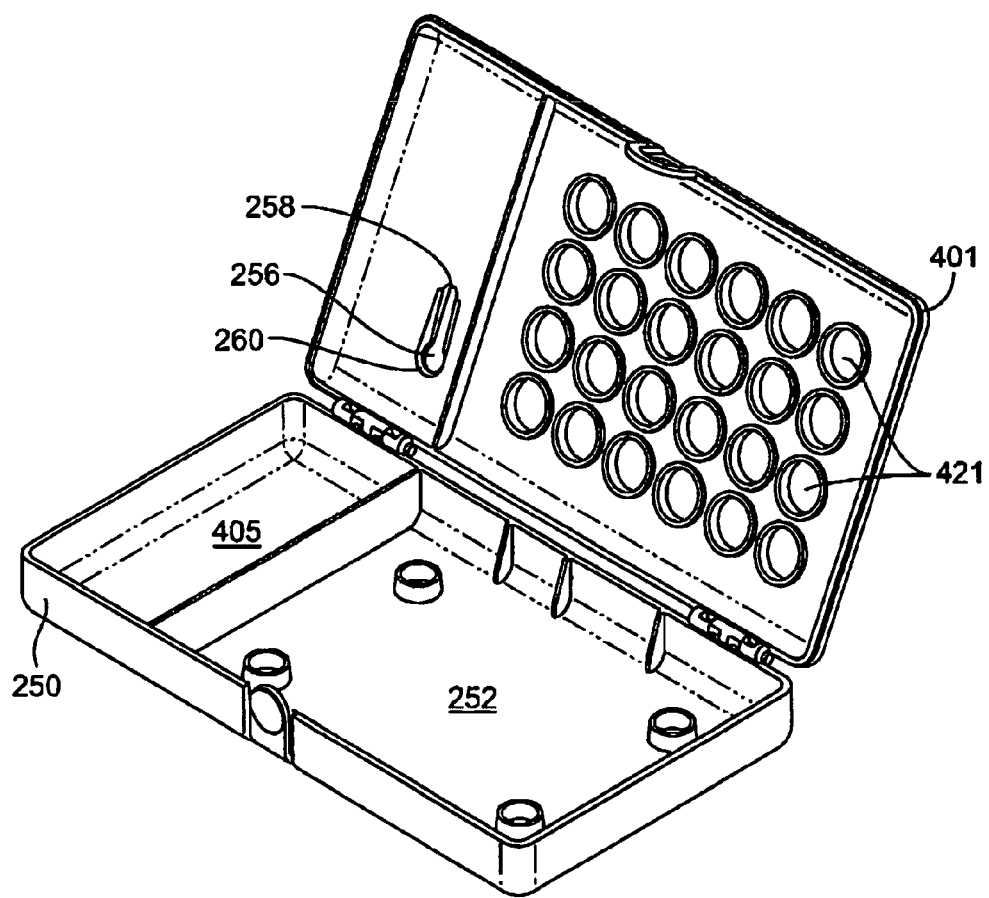
FIG. 28, in parts A to F, provides detailed views of a storage tray in accordance with representative embodiments of the present invention.
Figure 28B:
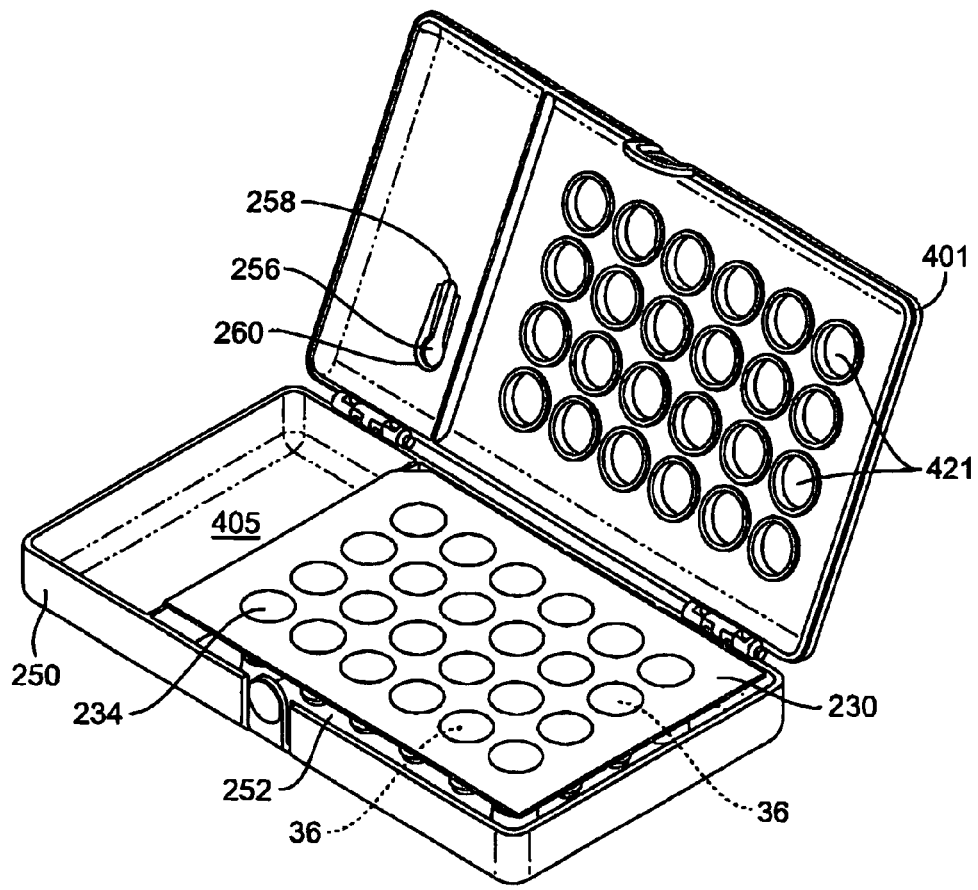
Figure 28C:
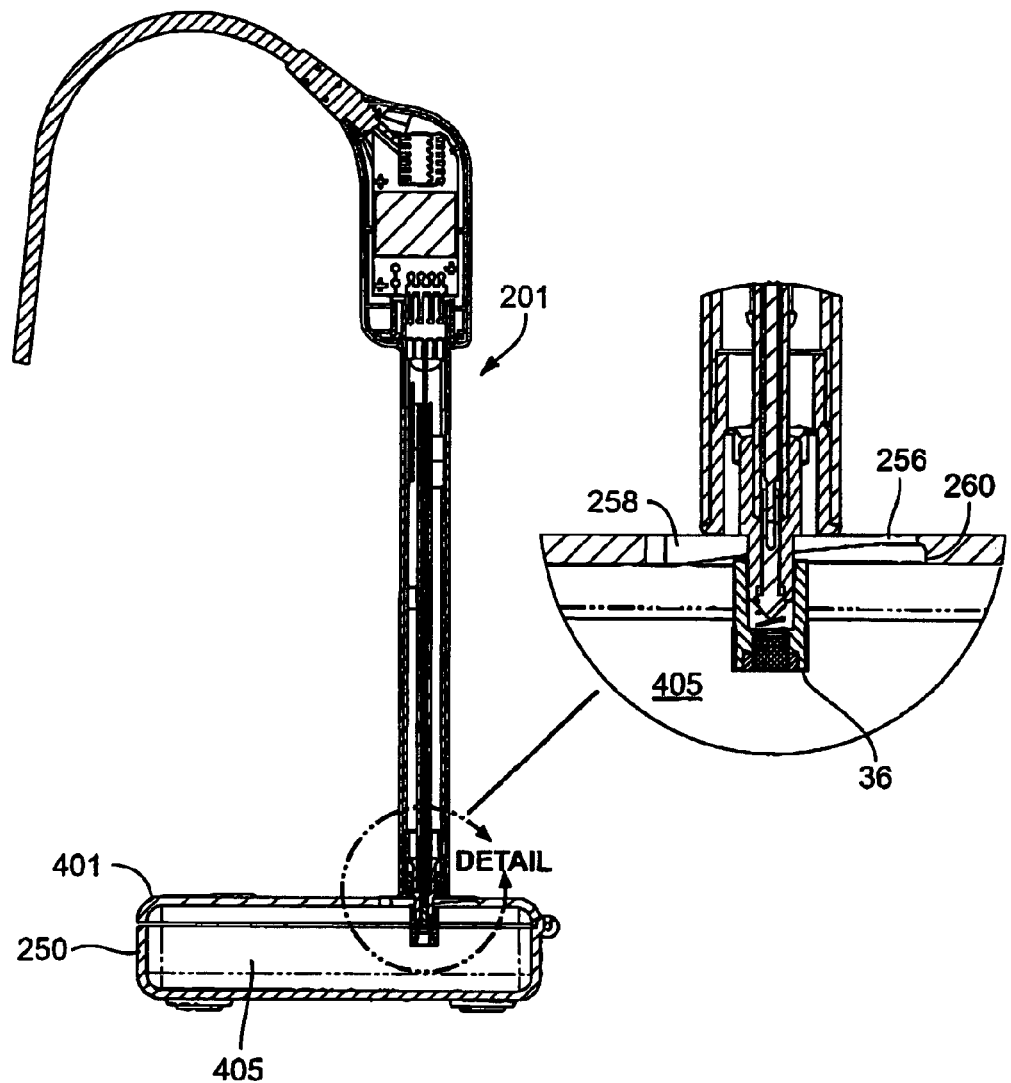
Figure 28D:
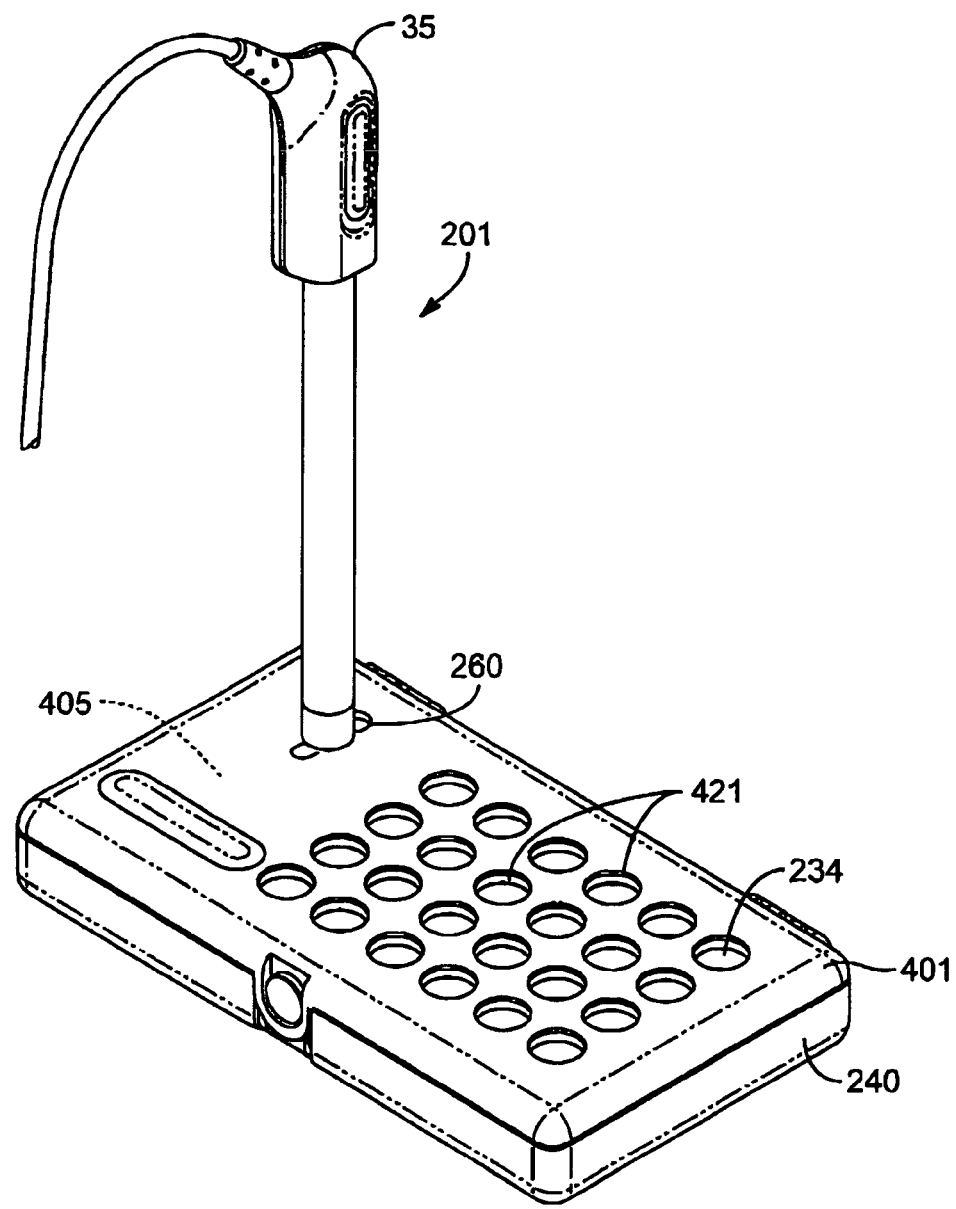
Figure 28E:
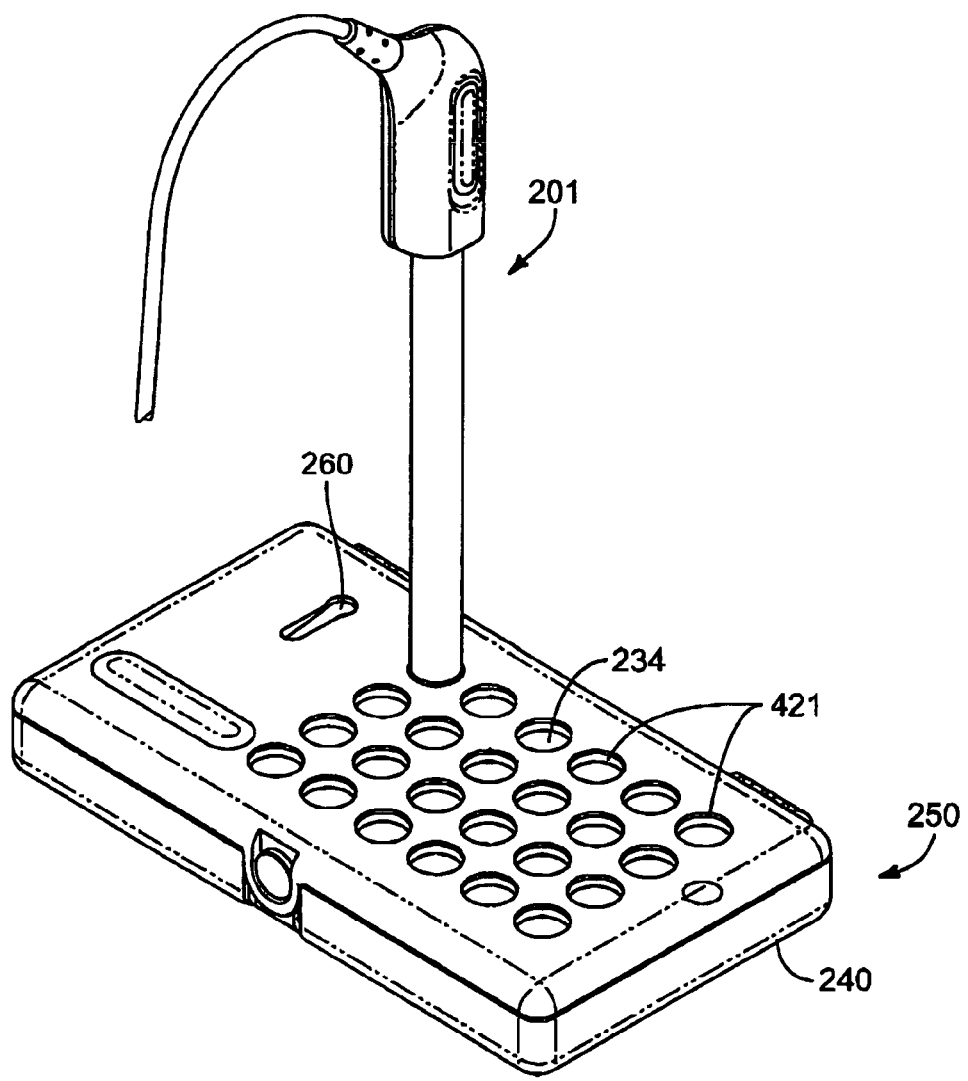
Figure 28F:
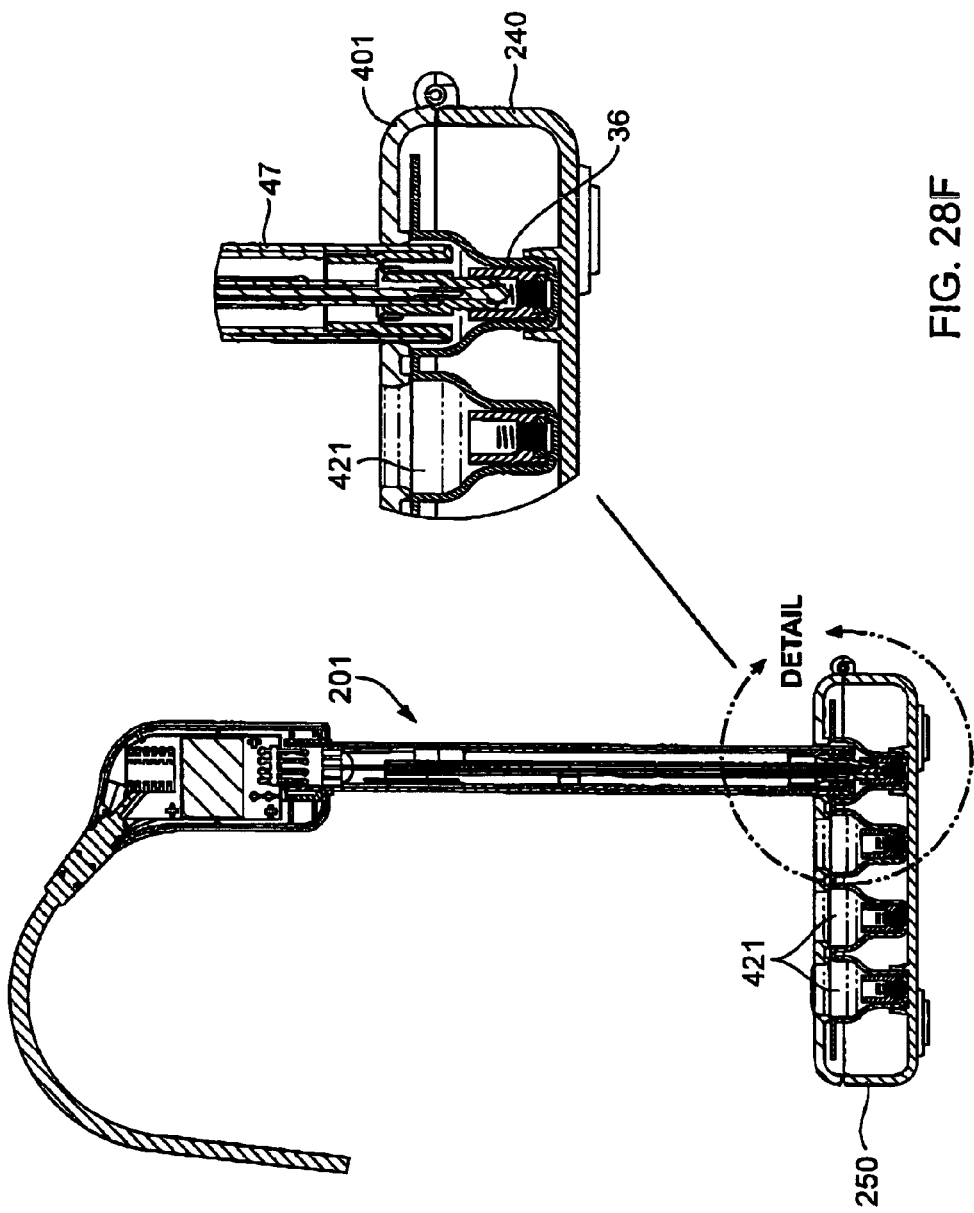

In some embodiments, a storage tray 250 is provided as a means for holding sealed package 230, as shown in FIGS. 28A and 28F. Storage tray 250 generally comprises a rigid or semi-rigid material having a well 252 sized and configured to receive sealed package 230. Some embodiments of storage tray 250 further include a plurality of holes 421 whereby to access sealed tips 36. In some embodiments, storage tray 250 comprises a tip removal slot 260. In other embodiments, storage tray 250 comprises a lid 401 having a plurality of holes to provide access to WE tips 36. Tip removal slot 260 is provided as a means for removing a WE tip 36 from the luer connector 38 of the probe assembly 201. In some embodiments, tip removal slot 260 comprises a tapered opening having a first end 256 for receiving the used tip 36, and a narrowed end 258 positioned opposite therefrom. As the tip 36 is moved from the first end 256 to the second end 258, the tapered opening acts as a wedge between the tip 36 and the cartridge luer assembly to displace the tip 36 from the luer connector 38. In some embodiments, removal slot 260 further comprises ramped walls whereby the wall of the opening gradually increases in thickness from the first end 256 to the second end 258, as shown in FIGS. 28C and 28D. Still further, in some embodiments storage tray 250 includes a collection bin 405 such that the tips 36 are automatically caught and retained in the collection bin following removal from the probe assembly 201.

B: Signal Acquisition and Processing

The pH sensor assembly of the present invention further includes a controller/processor or processor module and preamplifier board or preamp module. The controller/processor and preamplifier board contains electronic hardware and firmware that together implement a potentiostat capable of performing voltammetric experiments. Squarewave voltammetry is advantageous because it results in improved signal-to-noise versus other direct current (DC) techniques and removes signals resulting from irreversible redox processes; however, other methods can be employed. For example, in some embodiments the presence of an analyte is detected via amperometry.

In general, the processor module comprises the following components: a power supply, which may be powered by an external AC power source as in the embodiments described below, or in alternative embodiments, by an internal, battery-power DC source; connectors to interface to the pH sensor electrodes via the pH sensor electrode port; electronic hardware, which includes a microprocessor, signal conditioning amplifiers, and non-volatile memory; and firmware that accepts user inputs for starting and stopping scans, controls the electronic hardware to perform squarewave voltammetry by controlling the potential of the counter-electrode with respect to the reference electrode and measuring and analyzing data, e.g. the current through the working electrode, calculates and displays pH measurements from the data obtained, and stores time-stamped data to non-volatile memory and retrieves data from memory when recalled by the user or service personnel.

In some embodiments, the preamp module imposes the desired cell potential on the RE by receiving one signal from the processor module that represents the desired potential at the RE, receiving a second signal from the RE that represents the actual potential at the RE, and then outputting a third signal via the CE to adjust the electrochemical cell potential such that the desired potential at the RE is achieved. Due to the proximity of the WE to the RE, the difference in potential between the WE and RE is assumed to be negligible. Further, the preamp module electrically scales the signal from the WE such that it is readable by the processor module. The processor module receives the electrically scaled signal from the WE via the preamp and analyzes this signal relative to the desired cell potential as output from the processor module. The result of this analysis is compared with the characteristic analyte response of the WE to allow for the rendering of a value relevant to the analyte.

In some embodiments, the preamp module comprises the following components: a CE/RE feedback circuit, a WE current-to-voltage preamplifier, a digital potentiometer, non-volatile memory, mechanical relays and a solid state relay.

In operation, pH is measured using squarewave voltammetry. The controller/processor delivers a series of square-wave pulses to the sample, and current measurements are made at the end of each square wave pulse just before delivery of the next pulse. For each stair-step potential in the square-wave pulse series, both the forward current and reverse current are measured. The measured results are then subtracted from one another so as to measure reversible electrochemical processes by removing responses from non-reversible processes. Removing irreversible process responses increases the signal-to-noise ratio to enable a more precise pH measurement.

In some embodiments, current measurements are made using a microprocessor-controlled analog-to-digital converter. Digital filtering techniques may also be employed to further reduce signal noise beyond the noise reduction performed by the analog signal conditioning hardware. For example, in some embodiments multiple digital samples are taken at intervals and averaged to constitute one current measurement referred to as the difference current. In some embodiments the interval between digital samples is one millisecond. The results of these current measurements are analyzed by the microprocessor with respect to the potential at which they occurred. In some embodiments, analysis by the microprocessor includes i.) assembly of the difference current measurements into a continuous waveform, ii.) location of the highest amplitude peak in the difference current waveform, and iii.) comparison of the potential at which this peak occurred with pre-set calibration curves, where the input variable is peak potential and the output is the pH of the analyzed solution. In further embodiments, the continuous difference current waveform is digitally filtered by a weighted moving average (WMA) filter to further reduce spurious noise and more accurately locate the peak potential. In further embodiments, the WMA filter is replaced or supplemented by an Infinite Impulse Repose (IIR) digital filter. In other embodiments, the first and second derivatives of the continuous difference current waveform are used to facilitate peak potential location.

The CE/RE feedback circuit is located on the preamp module which is physically near the CE and RE. The electrical connection between the RE and the feedback circuit is high impedance, and therefore susceptible to influence from external noise sources, such as motors or laboratory stir plates. The present design locates the feedback circuit as near as possible to the CE/RE to reduce the influence of external noise sources. In some embodiments, it is further desirable for the signal preamplification circuitry to be physically near the WE for noise immunity. The signal preamplification circuitry converts currents on the order of tens or hundreds of microamps to voltages on the order of volts. After preamplification, it is possible to transmit the WE signal to the processor module via the one meter long probe cable with minimal interference from external noise sources. In other embodiments, the probe cable comprises a length greater than or less than one meter. An alternative embodiment converts the analog signal to a digital signal before transmission to the signal processing module to enable wireless transmission or transmission over longer distances.

In some embodiments, the probe electronics consume power on the order of 0.5 watt. Other embodiments may be powered via battery and transmit the WE signal to the processor module wirelessly. Wireless transmission is applicable for sensor arrangements other than a hand-held probe.

In some embodiments, it is further desirable for the microprocessor and associated circuitry to possess the ability to rapidly change the gain of the signal preamplification circuitry to compensate for variations in WE current intensity. The signal preamplification stage consists of a current-to-voltage converter with an adjustable gain resistor, such as a digital potentiometer. In some embodiments, the microprocessor continually adjusts the digital potentiometer value to achieve the best possible signal-to-noise ratio.

In some embodiments, it is further desirable for the microprocessor to control the square wave period, or the time interval between steps in the square wave pulse stream. The time required for the WE current to reach steady state may vary for each experiment due to many factors including the composition of the solution being analyzed. In traditional squarewave voltammetry the square wave period is pre-set such that the WE current always reaches steady state before the microprocessor measures the current. In an improvement to the art, the microprocessor continually measures the WE current, makes a decision as to when the current has reached steady state, and, thereupon, immediately proceeds to the next square wave step without waiting for a prescribed interval to elapse. It will be appreciated by anyone skilled in the art that this automatically variable square wave period results in a shorter overall scan time and shorter time required to perform a pH measurement.

In some embodiments, it is desirable to further stabilize the pH reading transmitted or displayed to the user by transmitting or displaying a running average of many consecutive scans. Upon detecting a change in calculated pH greater than a pre-set threshold, the processor module resets the running average such that the system responds immediately to gross changes in pH but responds gradually to subtle changes in pH.

Figure 29:
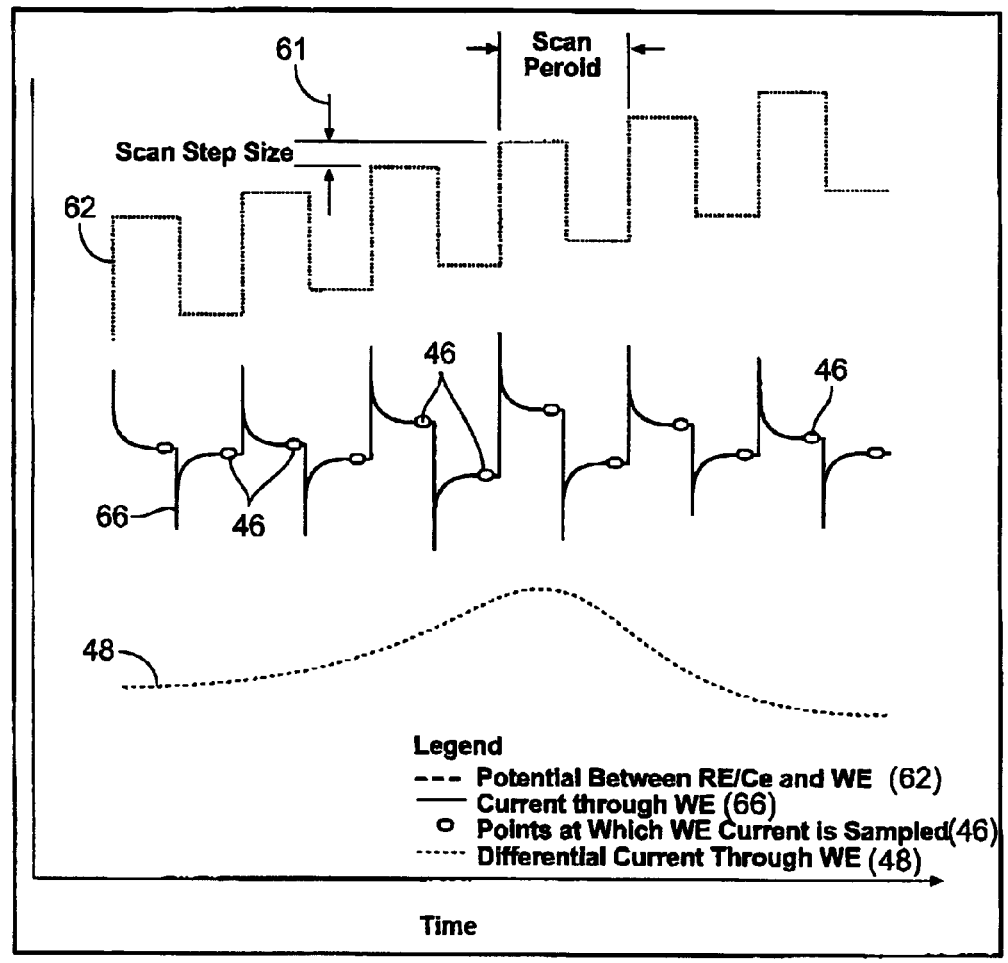
FIG. 29 is a graphical representation of voltammetry procedure as performed by a metering device system in accordance with a representative embodiment of the present invention.

In some embodiments, it is desirable to further reduce the time until a pH reading can be transmitted or displayed by employing a coarse/fine scan mode. Referring to FIG. 29, the Scan Step Size 61 is increased to a value larger than 2 millivolts, resulting in a shorter scan time with more coarse resolution. This coarse scan is used to display a roughly calculated pH value while a fine scan, or scan with smaller Scan Step Size 61, is carried out only on the region in which the voltammetric peak was found to reside via the coarse scan. Upon completing the fine scan a more precise calculated pH value is displayed. The fine scan across a narrow voltage range is continuously carried out until the resulting waveform is not found to contain a voltammetric peak, at which time the coarse scan across the entire pH voltage range is again employed.

In an alternative embodiment one or more coarse scans are interleaved such that the time required to transmit or display the initial pH reading is reduced. Further in some embodiments, one or more interleaved scans are executed to increase the accuracy and/or precision of the pH reading. Referring to FIG. 29, Signal 62, the Scan Step Size is increased such that the first scan drives a potential of 0, 4, 8, etc. . . . millivolts and the second, subsequent scan drives a potential of 2, 6, 10, etc. . . . millivolts to the electrochemical cell. Thus, the initial scan time, and time required to transmit or display the initial pH reading, is reduced by one-half. After the second, subsequent scan, the voltammetric peak positions are averaged and the calculated pH reading is more precisely transmitted or displayed. It will be appreciated by one skilled in the art that the interleaved scan mode may be extended to employ more than two interleaved scans to further reduce the time required to transmit or display the initial pH reading.

In some embodiments, it is further desirable for the probe electronics to possess the ability to be disconnected from the RE, CE, and WE to prevent current from inadvertently flowing through the electrodes and damaging them, particularly when the electronics are not powered but some potential remains in the electrochemical cell. The RE and WE are disconnected from the probe electronics when not in use via mechanical relays that are controlled via the processor module to ensure effectively zero leakage current. The CE is disconnected from the probe electronics when not in use via a solid state relay. The solid state relay has the advantage of being physically smaller than a mechanical relay and is allowable in the case of the CE because the CE is not likely to be damaged by leakage currents.

In some embodiments, the probe electronics further contain non-volatile memory used to store various data, such as a serial number, gain settings, configuration data, or calibration information specific to the probe.

The processor module may also contain non-volatile memory used to record time-stamped data for later download and analysis on a personal computer.

In square-wave voltammetry, the potential or difference in voltage 62 between RE 44 and WE 42 is swept in a stair-step like fashion while measuring the current 66 through the WE 42. In some embodiments RE 44 is connected to a high-impedance JFET op-amp that monitors the voltage of the RE 44. WE 42 is connected to a current-to-voltage amplifier for measuring current through WE 42. Finally, CE 40 is connected to an electronic driver whose purpose is to drive as much current through the cell as is required to give the desired stair-step voltage at RE 44.

Steady-state current 46 through WE 42 is measured after the cell has stabilized and just before the next voltage step 62 is applied. The differential current 48 through WE 42 is calculated by subtracting current 46 in the reverse direction from the current in the forward direction. In some embodiments, a scan step size used in processor module 50 is 2 mV, with a scan period of approximately 40 ms, the scan period being limited by the time constant for reaching steady-state current in the sample solution 120. One complete scan sweeps the potential on RE 44 from approximately 100 mV to approximately −850 mV and takes approximately 25 seconds to complete, including stabilization time before and after the scan.

Figure 30:
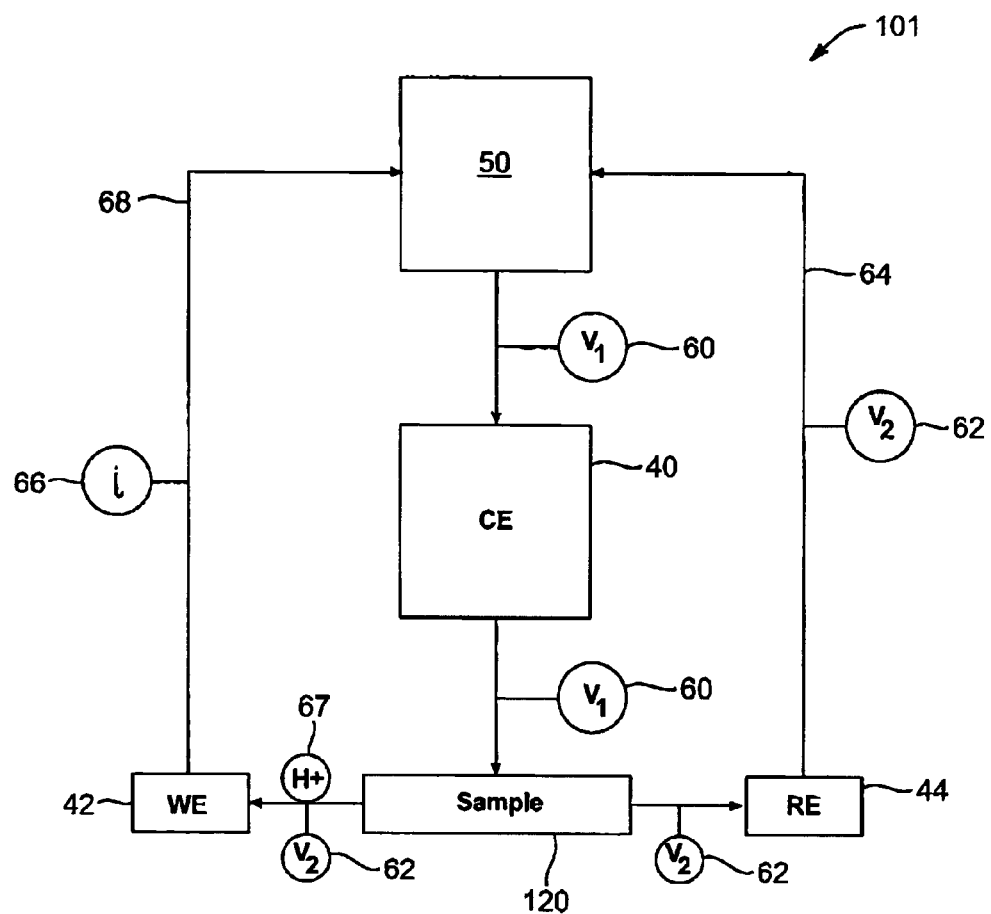
FIG. 30 is a schematic flow chart demonstrating the relationship of the various components of a solid-state pH probe and metering device system in accordance with a representative embodiment of the present invention.

Referring now to FIGS. 29 and 30, a graphical representation of voltage sweep 62 versus current response 66 for sample solution 120 is shown. Metering device 50 receives and plots signals 64 and 68 from probe assembly 201. As voltage 62 increases, the ASM of WE 42 undergoes a reduction causing current to flow with concomitant uptake of protons 67. As the voltage 62 increases beyond the optimal range for the sample solution 120, the ASM of WE 42 is completely reduced and current flow ceases. A center point 122 of the sample solution curve 120 represents maximum current flow of the ASM and is therefore a convenient marker to compare the sample solution 120 to previously measured standardized voltages 126 and 128 for know pH buffers. The voltage at which maximal current is observed is a characteristic of the ASM and the pH of the sample solution 120 being tested, as shown.

Referring now to FIG. 30, a flow diagram of the pH metering system 101 is shown. In some embodiments metering device 50 supplies a voltage sweep 60 to CE 40 of the probe assembly 201. In some embodiments voltage sweep 60 comprises a cyclic voltammetry from approximately 0.2 volts to approximately −1 volt relative to the silver/silver chloride reference electrode. In other embodiments voltage sweep 60 comprises a square-wave voltammetry from approximately 0.2 volts to approximately −1 volt relative to the silver/silver chloride reference electrode, as shown in FIG. 31.

Figure 31:
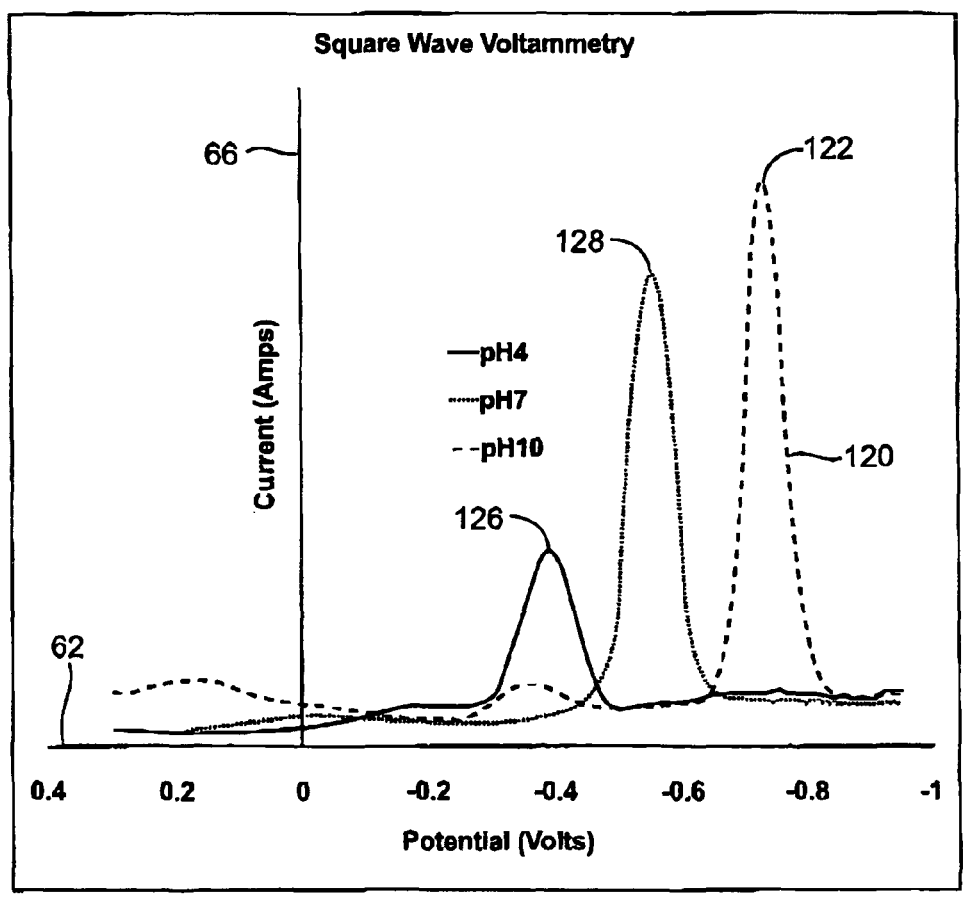
FIG. 31 is a graphical representation of a plotted square-wave voltammetry procedure as performed by a metering device system in accordance with a representative embodiment of the present invention.

FIG. 31 shows a graphical representation of a square-wave voltammetry as applied from the CE 40 to the WE via a sample solution. The resulting current through the WE is then recorded as a function of the potential between the WE and the RE. The voltage at which maximum current is observed is a characteristic of the ASM and the pH of the sample being tested, as described below.

The voltage at which the redox reaction occurs is dependent upon the concentration of protons in the sample solution. For example, where there is a high concentration of protons present (i.e., an acidic solution) the reaction occurs at a more positive voltage. Conversely, where there is a low concentration of protons present (i.e., an alkaline or basic solution) the reaction occurs at a more negative voltage. Therefore, by establishing standardized voltages for known pH buffers, the pH of a sample solution can be determined by comparing the redox voltage of the sample solution to the standardized redox voltages of the known pH buffers.

In some embodiments, the pH sensor comprises on-board circuitry for receiving and amplifying a signal from the WE. Signals from the WE are captured by the circuitry, amplified and then sent to processor module 50 for processing. Once processed, the pH value for the sample solution is displayed on the display 52. Processor module 50 generally comprises a combination of electronic hardware and firmware that together implement a potentiostat capable of performing voltammetric experiments, as described above and disclosed in U.S. Provisional Patent Application No. 61/163,139, filed Mar. 25, 2009 and entitled "INTERNALLY CALIBRATED DEVICE FOR MEASURING PH," incorporated herein by reference, in its entirety.

One of skill in the art will appreciate that various other voltammetries and electrochemical analytical techniques may be successfully used to vary the applied voltage and measure the resultant current supplied from the WE. For example, in some embodiments voltage sweep 60 comprises an AC wave form that is applied to the CE 40 from the metering device 50.

Section II: Related Devices

Figure 12:
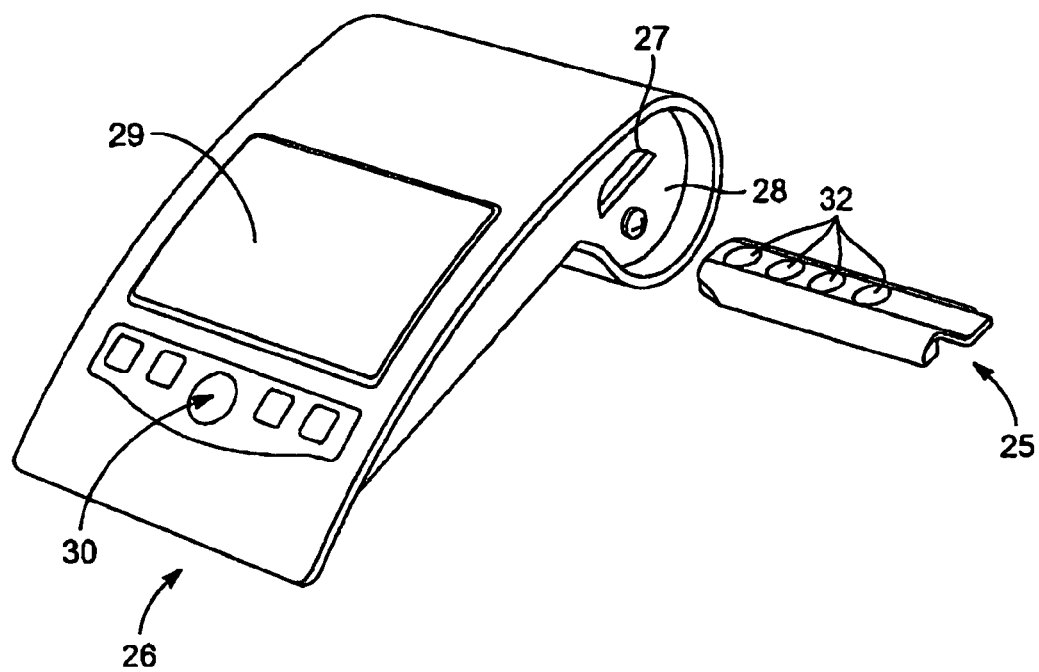
FIG. 12 shows a second exemplary embodiment of the invention.
Figure 13A:
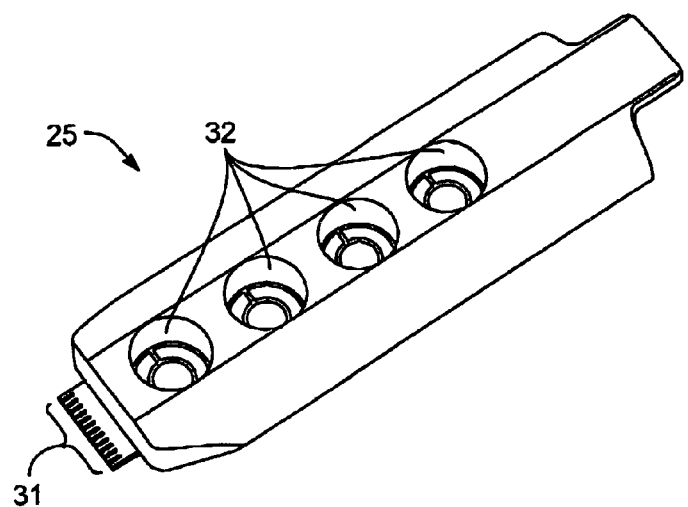
FIG. 13, in parts A and B, provides detailed views of the sensor well tray component of the second exemplary embodiment shown in FIG. 12.
Figure 13B:
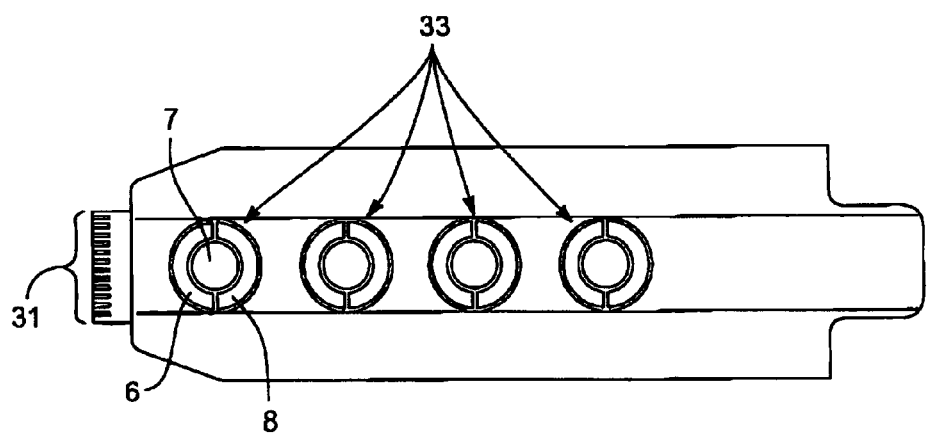

In some embodiments of the present invention, the pH sensor assembly further comprises a sensor well tray assembly, an example of which is shown in FIGS. 12 and 13.

A pH sensor well tray 25 is constructed with multiple sample wells 32 each of which contains a pH sensor 33 comprising a WE, a RE, and a CE. The pH sensor may have any of a number of different configurations. In one embodiment, the sensor additionally includes an AIE. The electrodes of each pH sensor are in electrical connection with an electrical edge connector 31, which electrically connects the sensor electrodes to the controller/processor 26 after the tray is inserted into the sensor well tray port 27 of the controller/processor.

The well sensors may be constructed in a variety of ways, including but not limited to the method for constructing the pH sensor tip described above. A variety of tray configurations are possible. For example, the trays may be configured as multi-well plates amenable to the use of automated sample handling systems for dispensing multiple samples into the sensor wells.

What is claimed is:

1. A pH meter device, comprising:
    a probe assembly having a first end, a second end and a central axis;
    a reference electrode having a frit disposed at the first end of the probe assembly;
    a working electrode comprising an analyte sensitive material coupled to a substrate, the analyte sensitive material and the substrate being disposed at the first end of the probe assembly;
    a counter electrode disposed at the first end of the probe assembly;
    an enclosure disposed at the second end of the probe assembly;
    a pre-amplification circuit disposed within the enclosure and electrically coupled to the reference electrode, the working electrode and the counter electrode; and
    a processor electrically coupled to the pre-amplification circuit for detecting an analyte by voltammetry, wherein the reference electrode, the working electrode and the counter electrode are coaxially positioned relative to the central axis, and wherein the pre-amplification circuit scales a signal received from the working electrode,
    wherein the reference electrode is a cartridge assembly coaxially disposed within the counter electrode, the reference electrode comprising (a) a first electrolyte solution contained by said cartridge assembly that can be placed in electrical contact with an analyte solution via a frit at one end of said cartridge assembly; and (b) a mini reference assembly disposed within the cartridge assembly, the mini reference assembly comprising:
        a casing having a first end and a second end, the first end of the casing having an opening for receiving a frit member and the second end of the casing having an opening for receiving an electrode wire having a first end and a second end, the first end being electrically coupled to the pre-amplification circuit, and the second end being exposed to a second electrolyte solution contained by the casing, wherein said second electrolyte solution is in electrical contact with said first electrolyte solution via said frit member, and at least a portion of the electrode wire is positioned proximate to the working electrode, such that the temperature of the electrode wire is substantially similar to the temperature of the working electrode.

2. The pH meter device of claim 1, wherein the analyte sensitive material is selected from the group consisting of anthraquinone described by the following Formula I:

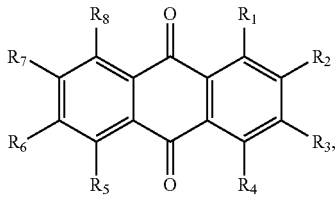

Formula I

Phenanthrenequinone described by the following Formula II:

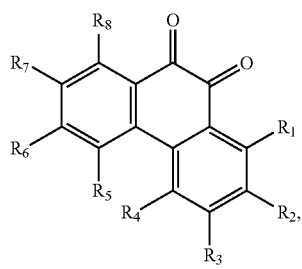

Formula II ortho-benzoquinone described by the following Formula III:

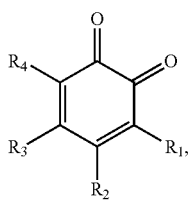

Formula III

N,N'-diphenyl para-phenylenediamine described by the following Formula IV:

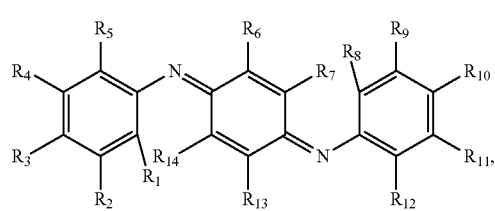

Formula IV

Anthracene described by the following Formula V:

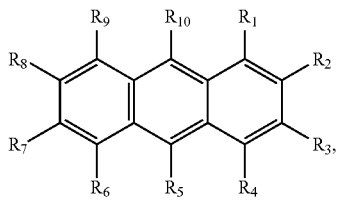

Formula V

Naphthaquinone described by the following Formula VI:

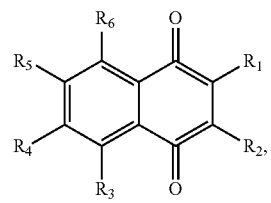

Formula VI para-benzoquinone described by the following Formula VII:

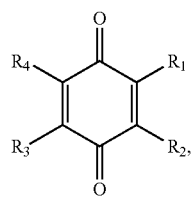

Formula VII and azobenzene described by the following Formula VIII:

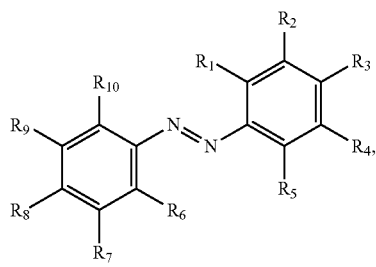

Formula VIII wherein at least one of R1, R2, R3, R4, R5, R6, R7, R8, R9, R10, R11, R12, R13, and R14 are substituted with a chemical moiety selected from the group consisting of a hydrogen moiety, an alkyl moiety, an aryl moiety, a heteroaryl moiety, an amino moiety, an amido moiety, a carboxyl moiety, a hydroxylmethyl moiety, a carbonyl moiety, an ether moiety and an alkoxy ether moiety.

3. The pH meter device of claim 1, wherein the analyte sensitive material is covalently attached to the substrate via a chemical linker.

4. The pH meter device of claim 1, wherein the analyte sensitive material is physisorbed within the substrate.

5. The pH meter device of claim 1, wherein the substrate is selected from the group consisting of a noble metal material, a semiconductive material, a conductive metal alloy material, a conductive polymeric compound, and a carbon-based material.

6. The pH meter device of claim 5, wherein the carbon-based material is selected from the group consisting of a carbon allotrope material, a pyrolytic graphite material, graphite, amorphous carbon, carbon black, single-walled carbon nanotubes, multi-walled carbon nanotubes, glassy carbon, boron-doped diamonds, and pyrolyzed photoresist films.

7. The pH meter device of claim 1 further comprising, a clip device for securing the probe assembly to a vessel, the clip device comprising:
 an aperture for receiving a portion of the probe assembly; and
 a body coupled to the aperture, the body having a first arm for receiving a rim surface of the vessel such that the aperture is located proximate to an interior of the vessel and the first arm is located proximate to an exterior of the vessel.

8. The pH meter device of claim 1 further comprising, a storage device comprising an enclosure having a base portion selectively coupled to a cover portion, the base portion having a well for receiving a wetting solution, the cover portion having an aperture for supporting a shaft portion of the probe assembly, the aperture being in approximate alignment with the well such that upon insertion of the probe assembly into the aperture, a tip portion of the probe assembly is submerged in the wetting solution.

* * * * *